United States Patent
Rutherford et al.

(10) Patent No.: US 7,309,232 B2
(45) Date of Patent: Dec. 18, 2007

(54) METHODS FOR TREATING DENTAL CONDITIONS USING TISSUE SCAFFOLDS

(75) Inventors: Bruce Rutherford, Seattle, WA (US); Christopher Somogyi, Woodinville, WA (US); Clinton White, Raleigh, NC (US); Erick Rabins, Seattle, WA (US)

(73) Assignee: Dentigenix Inc., Seattle, WA (US)

( * ) Notice: Subject to any disclaimer, the term of this patent is extended or adjusted under 35 U.S.C. 154(b) by 0 days.

(21) Appl. No.: 10/684,226

(22) Filed: Oct. 10, 2003

(65) Prior Publication Data
US 2005/0079470 A1 Apr. 14, 2005

(51) Int. Cl.
*A61C 5/04* (2006.01)
*A61B 19/02* (2006.01)

(52) U.S. Cl. .................... 433/226; 206/63.5
(58) Field of Classification Search .......... 433/226, 433/228.1, 141, 163, 91, 92, 93, 94, 95, 96, 433/224; 206/63.5
See application file for complete search history.

(56) References Cited

U.S. PATENT DOCUMENTS

| | | | |
|---|---|---|---|
| 2,885,782 A * | 5/1959 | Groves .................. | 433/95 |
| 4,137,921 A | 2/1979 | Okuzumi et al. | |
| 4,166,800 A | 9/1979 | Fong | |
| 4,181,983 A | 1/1980 | Kulkarni | |
| 4,243,775 A | 1/1981 | Rosensaft et al. | |
| 4,279,249 A | 7/1981 | Vert et al. | |
| 4,300,565 A | 11/1981 | Rosensaft et al. | |
| 4,347,234 A | 8/1982 | Wahlig et al. | |
| 4,384,975 A | 5/1983 | Fong | |
| 4,390,519 A | 6/1983 | Sawyer | |
| 4,394,370 A | 7/1983 | Jefferies | |
| 4,409,332 A | 10/1983 | Jefferies et al. | |
| 4,530,449 A | 7/1985 | Nozawa et al. | |

(Continued)

FOREIGN PATENT DOCUMENTS

WO WO 00/56375 A2 9/2000

(Continued)

OTHER PUBLICATIONS

Giusti et al., "New Biolized Polymers for Cadiovascular Applications," Life Support Syst. 3(Suppl 1):476-80 (1985).

(Continued)

*Primary Examiner*—Cary E. O'Connor
(74) *Attorney, Agent, or Firm*—Nixon Peabody LLP

(57) ABSTRACT

The invention provides methods, apparatus and kits for regenerating dental tissue in vivo that are useful for treating a variety of dental conditions, exemplified by treatment of caries. The invention uses tissue scaffold wafers, preferably made of PGA, PLLA, PDLLA or PLGA dimensioned to fit into a hole of corresponding sized drilled into the tooth of subject to expose dental pulp in vivo. In certain embodiments the tissue scaffold wafer further comprises calcium phosphate and fluoride. The tissue scaffold wafer may be secured into the hole with a hydrogel, a cement or other suitable material. Either the wafer or the hydrogel or both contain a morphogenic agent, such as a member encoded by the TGF-β supergene family, that promotes regeneration and differentiation of healthy dental tissue in vivo, which in turn leads to remineralization of dentin and enamel. The tissue scaffold may further include an antibiotic or anti-inflammatory agent.

62 Claims, 10 Drawing Sheets

U.S. PATENT DOCUMENTS

| | | | |
|---|---|---|---|
| 4,538,603 | A | 9/1985 | Pawelchak et al. |
| 4,539,981 | A | 9/1985 | Tunc |
| 4,563,489 | A | 1/1986 | Urist |
| 4,568,559 | A | 2/1986 | Nuwayser et al. |
| 4,578,384 | A | 3/1986 | Hollinger |
| 4,585,797 | A | 4/1986 | Cioca |
| 4,596,574 | A | 6/1986 | Urist |
| 4,623,588 | A | 11/1986 | Nuwayser et al. |
| 4,703,108 | A | 10/1987 | Silver et al. |
| 4,741,337 | A | 5/1988 | Smith et al. |
| 4,744,365 | A | 5/1988 | Kaplan et al. |
| 4,795,804 | A | 1/1989 | Urist |
| 4,818,542 | A | 4/1989 | DeLuca et al. |
| 4,822,278 | A * | 4/1989 | Oliva et al. .................. 433/91 |
| 4,837,285 | A | 6/1989 | Berg et al. |
| 4,839,130 | A | 6/1989 | Kaplan et al. |
| 4,844,854 | A | 7/1989 | Kaplan et al. |
| 4,877,864 | A | 10/1989 | Wang et al. |
| 4,889,119 | A | 12/1989 | Jamiolkowski et al. |
| 4,898,186 | A | 2/1990 | Ikada et al. |
| 4,898,734 | A | 2/1990 | Mathiowitz et al. |
| 4,916,193 | A | 4/1990 | Tang et al. |
| 4,938,763 | A | 7/1990 | Dunn et al. |
| 4,961,707 | A | 10/1990 | Magnusson et al. |
| 4,968,590 | A | 11/1990 | Kuberasampath et al. |
| 4,975,527 | A | 12/1990 | Koezuka et al. |
| 5,004,602 | A | 4/1991 | Hutchinson |
| 5,007,939 | A | 4/1991 | Delcommune et al. |
| 5,011,691 | A | 4/1991 | Oppermann et al. |
| 5,011,692 | A | 4/1991 | Fujioka et al. |
| 5,013,649 | A | 5/1991 | Wang et al. |
| 5,037,639 | A | 8/1991 | Tung |
| 5,051,272 | A | 9/1991 | Hermes et al. |
| 5,077,049 | A | 12/1991 | Dunn et al. |
| 5,080,665 | A | 1/1992 | Jarrett et al. |
| 5,081,106 | A | 1/1992 | Bentley et al. |
| 5,084,051 | A | 1/1992 | Tormala et al. |
| 5,106,748 | A | 4/1992 | Wozney et al. |
| 5,108,753 | A | 4/1992 | Kuberasampath et al. |
| 5,108,755 | A | 4/1992 | Daniels et al. |
| 5,116,738 | A | 5/1992 | Wang et al. |
| 5,128,136 | A | 7/1992 | Bentley et al. |
| 5,133,755 | A | 7/1992 | Brekke |
| 5,141,905 | A | 8/1992 | Rosen et al. |
| 5,143,730 | A | 9/1992 | Fues et al. |
| 5,149,691 | A | 9/1992 | Rutherford |
| 5,162,430 | A | 11/1992 | Rhee et al. |
| 5,166,058 | A | 11/1992 | Wang et al. |
| 5,171,217 | A | 12/1992 | March et al. |
| 5,185,152 | A | 2/1993 | Peyman |
| 5,187,076 | A | 2/1993 | Wozney et al. |
| 5,192,741 | A | 3/1993 | Orsolini et al. |
| 5,197,977 | A | 3/1993 | Hoffman, Jr. et al. |
| 5,206,028 | A | 4/1993 | Li |
| 5,227,157 | A | 7/1993 | McGinity et al. |
| 5,231,169 | A | 7/1993 | Constantz et al. |
| 5,250,584 | A | 10/1993 | Ikada et al. |
| 5,268,167 | A | 12/1993 | Tung |
| 5,268,178 | A | 12/1993 | Calhoun et al. |
| 5,271,961 | A | 12/1993 | Mathiowitz et al. |
| 5,278,201 | A | 1/1994 | Dunn et al. |
| 5,278,202 | A | 1/1994 | Dunn et al. |
| 5,281,419 | A | 1/1994 | Tuan et al. |
| 5,288,496 | A | 2/1994 | Lewis |
| 5,308,623 | A | 5/1994 | Fues et al. |
| 5,320,624 | A | 6/1994 | Kaplan et al. |
| 5,324,307 | A | 6/1994 | Jarrett et al. |
| 5,324,520 | A | 6/1994 | Dunn et al. |
| 5,350,580 | A | 9/1994 | Muchow et al. |
| 5,360,610 | A | 11/1994 | Tice et al. |
| 5,366,508 | A | 11/1994 | Brekke |
| 5,366,733 | A | 11/1994 | Brizzolara et al. |
| 5,366,734 | A | 11/1994 | Hutchinson |
| 5,376,636 | A | 12/1994 | Rutherford et al. |
| 5,437,857 | A | 8/1995 | Tung |
| 5,460,803 | A | 10/1995 | Tung |
| 5,534,244 | A | 7/1996 | Tung |
| 5,562,895 | A | 10/1996 | Tung |
| 5,833,954 | A | 11/1998 | Chow et al. |
| 5,855,562 | A * | 1/1999 | Moore et al. ................ 604/119 |
| 5,871,360 | A * | 2/1999 | Kato .......................... 433/226 |
| 5,885,829 | A * | 3/1999 | Mooney et al. ............. 435/325 |
| 5,993,786 | A | 11/1999 | Chow et al. |
| 6,000,341 | A | 12/1999 | Tung |
| 6,001,897 | A | 12/1999 | Dickens |
| 6,056,930 | A | 5/2000 | Tung |
| 6,114,408 | A | 9/2000 | Dickens |
| 6,187,838 | B1 | 2/2001 | Dickens |
| 6,206,959 | B1 | 3/2001 | Dickens |
| 6,210,759 | B1 | 4/2001 | Dickens |
| 6,281,256 | B1 | 8/2001 | Harris et al. |
| 6,398,859 | B1 | 6/2002 | Dickens et al. |
| 6,413,498 | B1 | 7/2002 | Malmagro |
| 6,472,210 | B1 | 10/2002 | Holy et al. |
| 6,793,725 | B2 | 9/2004 | Chow et al. |
| 2002/0119180 | A1 | 8/2002 | Yelick et al. |
| 2002/0137812 | A1 | 9/2002 | Chow et al. |
| 2003/0031696 | A1 | 2/2003 | Baum et al. |
| 2004/0058442 | A1* | 3/2004 | Shi et al. .................... 435/366 |

FOREIGN PATENT DOCUMENTS

| | | |
|---|---|---|
| WO | WO 02/07679 | 1/2002 |

OTHER PUBLICATIONS

Merrill, "Poly(Ethylene Oxide) Star Molecules: Synthesis, Characterization, and Applications in Medicine and Biology," *J. Biomater. Sci. Polym. Ed.* 5(1-2):1-11 (1993).

Ricordi et al., "Renal Subcapsular Transplantation of Clusters of Hepatocytes in Conjunction with Pancreatic Islets," *Transplantation* 45(6):1148-51 (1988).

Schmolka, "Artificial Skin. I. Preparation and Properties of Pluronic F-127 Gels for Treatment of Burns," *J. Biomed. Mater. Res.* 6(6):571-82 (1972).

Vacanti et al., "Tissue-engineered Growth of Bone and Cartilage," *Transplantation Proc.* 25(1):1019-21 (1993).

Allcock et al., "Poly[(amino acid ester) phosphazenes] As Substrates for the Controlled Release of Small Molecules," *Biomat.* 15(8):563-9 (1994) (Abstract only).

Alsberg et al., "Engineering Growing Tissues," *Proc. Nat'l Acad. Sci. U.S.A.* 99(19):12025-30 (2002)

Amiji & Park, "Surface modification of polymeric biomaterials with poly(ethylene oxide), albumin, and heparin for reduced thrombogenicity," *J. Biomater. Sci. Polym. Ed.* 4(3):217-34 (1993): (Abstract only).

Anselme et al., Inhibition of calcification in vivo by acyl azide cross-linking of a collagen-glycosaminoglycan sponge. *Matrix* 12(4):264-73 (1992) (Abstract only).

Atala et al., Endoscopic treatment of vesicoureteral reflux with a chondrocyte-alginate suspension. *J. Urol.* 152(2 Pt 2):641-3; (1994) (Abstract only).

Atala et al., "Injectable alginate seeded with chondrocytes as a potential treatment for vesicoureteral reflux," *J. Urol.* 150(2 Pt 2):745-7 (1993) (Abstract only).

Bell et al., "Living tissue formed in vitro and accepted as skin-equivalent tissue of full thickness," *Science* 211(4486):1052-4 (1981) (Abstract only).

Blair et al., "Clinical trial of calcium alginate haemostatic swabs," *Br. J. Surg.* 77(5):568-70 (1990) (Abstract only).

Cavallaro et al., "The nucleotide sequence of a complementary DNA encoding Flaveria bidentis carbonic anhydrase," *FEBS Lett.*, 350(2-3):216-8 (1994) (Abstract only).

Clarkson "Sponge implants for flat breasts," *Proc. R. Soc. Med.,* 53:880-1 (1960).

Compton et al., "Skin regenerated from cultured epithelial autogradts on full-thickness burn wounds from 6 days to 5 years after grafting. A light, electron microscopic and immunohistochemical study," *Lab. Invest.*, 60(5):600-12 (1989) (Abstract only).

Daniels et al., "Evaluation of absorbable poly(ortho esters) for use in surgical implants," *J. Appl. Biomater.*, 5(1):51-64 (19940 (Abstract only).

Delustro et al., "Immune responses to allogeneic and xenogeneic implants of collagen and collagen derivatives," *Clin. Orthop. Relat. Res.*, (260):263-79 (1990) (Abstract only).

Dixit, "Development of a bioartificial liver using isolated hepatocytes," *Artif. Organs*, 18(5):371-84 (1994) (Abstract only).

Ducheyne & Healy, "The effect of plasma-sprayed calcium phosphate ceramic coatings on the metal ion release from porous titanium and cobalt-chromium alloys." *J. Biomed. Mater. Res.*, 22(12):1137-63 (1988) (Abstract only).

Dulcey et al., "Deep UV photochemistry of chemisorbed monolayers: patterned coplanar molecular assemblies," *Science*, 252(5005):551-4 (1991) (Abstract only).

Embleton & Tighe, "Polymers for biodegradable medical devices. X. Microencapsulation studies: control of poly-hydroxybutyrate-hydroxyvalerate microcapsules porosity via polycaprolactone blending," *J. Microvencapsul.*, 10(3):341-52 (1993) (Abstract only).

Emerich et al., "a novel approach to neural transplantation in Parkinson's disease: use of polymer-encapsulated cell therapy," *Neurosci. Biobehav. Rev.*, 16(4):437-47 (1992) (Abstract only).

Engelberg & Kohn, "Physico-mechanical properties of degradable polymers used in medical applications: a comparative study," *Biomaterials*, 12(3):292-304 (1991) (Abstract only).

Frazza & Schmitt, "A new absorbable suture," *J. Biomed. Mater. Res.*, 5(2):43-58 (1971) (Abstract only).

Giunchedi et al., "Cellulose acetate butyrate and polycaprolactone for ketoprofen spray-dried microsphere preparation," *J. Microencapsul.*, 11(4):381-93 (1994) (Abstract only).

Goldberg et al., "Cloning and expression of a collagen-analog-encoding synthetic gene in Escherichia coli, " *Gene*, 80(2):305-14 (1989) (Abstract only).

Gombotz & Pettit, "Biodegradable polymers for protein and peptide drug delivery," *Bioconjug. Chem.*, 6(4):332-51 (1995) (Abstract Only).

Green et al., "Growth of cultured human epidermal cells into multiple epithelia suitable for grafting," *Proc. Natl. Acad. Sci. U S A*, 76(11):5665-8 (1979).

Guénard et al., "Syngeneic Schwann Cells Derived from Adult Nerves Seeded in Semipermeable Guidance Channels Enhance Peripheral Nerve Regeneration," *J. Neurosci.* 12(9):3310-20 (1992).

Hansbrough et al., "Evaluation of a biodegradable matrix containing cultured human fibroblasts as a dermal replacement beneath meshed skin grafts on athymic mice," *Surgery*, 111(4):438-46 (1992) (Abstract only).

Harris et al., Open pore biodegradable matrices formed with gas foaming. *J. Biomed. Mat. Res.* 42(3):396-402 (1998) (Abstract only).

Heimbach et al., "Artificial Dermis for Major Burns," *Ann. Surg.* 208(3):313-19 (1988).

Heller, "Controlled drug release from poly(ortho esters)," *Ann. N Y Acad. Sci.*, 446:51-66 (1985).

Hill-West et al., "Efficacy of a resorbably hydrogel barrier, oxidized regenerated cellulose, and hyaluronic acid in the prevention of ovarian adhesions in a rabbit model," *Fertil. Steril.*, 62(3):630-4 (1994) (Abstract only).

Hynes et al., "Selective Expression of an Endogenous Lactose-Binding Lectin Gene in Subsets of Central and Peripheral Neurons," *J. Neurosci.* 10(3):1004-13 (1990).

Jarcho, "Calcium phosphate ceramics as hard tissue prosthetics," *Clin. Orthop. Relat. Res.*, (157):259-78 (1981).

Kallen et al., "Effect of encephalitogenic protein on migration in agarose of leukocytes from patients with multiple sclerosis. Variable of the antigen in a large dose range, with a literature review," *Acta. Neurol. Scand.*, 55(1):33-46 (1977) (Abstraact only).

Kaplan & Mason, Jr., "Antimicrobial agents: resistance patterns of common pathogens," *Pediatr. Infect. Dis. J.*, 13(11):1050-3 (1994).

Kasai et al., "Is the biological artificial liver clinically applicable? A historic review of biological artificial liver support systems," *Artif. Organs*, 18(5):348-54 (1994) (Abstract only).

Katz & Turner, "Evaluation of tensile and absorption properties of polyglycolic acid sutures," *Surg. Gynecol. Obstet.*, 131(4):701-16 (1970).

Koide et al., "A new type of biomaterial for artificial skin: dehydrothermally cross-linked compsites of fibrillar and denatured collagens," *J. Biomed. Mater. Res.*, 27(1):79-87 (1993) (Abstract only).

Kung et al., "Surface modifications of alginate/poly(L-lysine) microcapsular membranes with poly(ethylene glycol) and poly(vinyl alcohol)," *Biomaterials*, 16(8):649-55 (1995) (Abstract only).

Langer & Vacanti, "Tissue engineering," *Science*, 260(5110):920-6 (1993) (Abstract only).

Laurencin & Langer, "Polymeric controlled release systems: new methods for drug delivery," *Clin. Lab. Med.*, 7(2):301-23 (1987) (Abstract only).

Laurencin et al., "Use polyphosphazenes for skeletal tissue regeneration," *J. Biomed. Mater. Res.*, 27(7):963-73 (1993) (Abstract only).

Leenslag et al., Resorbable materials of poly(L-lactide). VII. In vivo and in vitro degradation. *Biomaterials*, 8(4):311-4 (1987) (Abstract only).

Lemons et al., "Significance of the porosity and physical chemistry of calcium phosphate ceramics/Orthopedic Uses," *Ann. N.Y. Acad. Sci.*, 523:278-82 (1988).

Lentz, "Polymer-induced membrane fusion: potential mechanism and relation to cell fusion events," *Chem. Phys. Lipids*, 73(1-2):91-106 (1994) (Abstract only).

Lévesque et al., "Maintenance of Long-Term Secretory Function by Microencapsulated Islets of Langerhans," *Endocrinol.* 130(2):644-50 (1992).

Lim & Sun, "Microencapsulated islets as bioartificial endocrine pancreas," *Science*, 210(4472):908-10 (1980) (Abstract only).

Lom et al., "A versatile technique for patterning biomolecules onto glass coverslips," *J. Neurosci. Methods*, 50(3):385-97 (1993) (Abstract only).

Lopez et al., "An improved Bradford protein assay for collagen proteins," *Clin. Chim. Acta.*, 220(1):91-100 (1993) (Abstract only).

Lora et al., "Biocompatible polyphosphazenes by radiation-induced graft copolymerization and heparinization," *Biomaterials*, 12(3):275-80 (1991) (Abstract only).

Massia & Hubbell, "Human endothelial cell interactions with surface-coupled adhesion peptides on a nonadhesive glass substrate and two polymeric biomaterials," *J. Biomed. Mater. Res.*, 25(2):223-42 (1991) (Abstract only).

Matsuda & Moghaddam, "Development of thermosensitive peptidyl cell substrate synthesis and artificial fibrin glue," *ASAIO Trans.*, 37(3):M196-7 (1991) (Abstract only).

McGrath & Chua, "The autumn greening of Cold Spring Harbor," *New Biol.*, 1992. 4(2):107-14.

Mikos et al., "Preparation and Characterization of Poly(L-Lactic Acid) Foams," *Polymer* 35(5):1068-77 (1994) (Abstract only).

Mikos et al., "Preperation of poly(glycolic acid) bonded fiber structures for cell attachment and transplantation," *J. Biomed. Mater. Res.*, 37(2):193-9 (1993) (Abstract only).

Mooney et al., "Cytoskeletal Filament Assembly and the Control of Cell Spreading and Function by Extracellular Matrix," *J. Cell Sci.* 108(Pt 6):2311-20 (1995).

Mooney et al., "Extracellular Matrix Controls Tubulin Monomer Levels in Hepatocytes by Regulating Protein Turnover," *Mo. Biol. Cell* 5(12):1281-8 (1994).

Mooney et al., "Switching from differentiation to growth in hepatocytes: control by extracellular matrix," *J. Cell Physiol.*, 141(3):497-505 (1992) (Abstract only).

Mooney et al., "Biodegradable sponges for hepatocyte transplantation," *J. Biomed. Mater. Res.*, 29(8):959-65 (1995) (Abstract only).

Mooney et al., "Design and fabrication of biodegradable polymer devices to engineer tubular tissues," *Cell Transplant*, 3(2):203-10 (1994) (Abstract only).

Mooney et al., "Engineering dental pulp-like tissue in vitro," *Biotechnol. Prog.*, 12(6):865-8 (1996) (Abstract only).

Mooney et al., "Novel approach to fabricate porous sponges of poly(D,L-lactic-co-glycolic acid) without the use of organic solvents," *Biomaterials*, 17(14):1417-22 (1996) (Abstract only).

Morikawa et al., "Enhancement of therapuetic effects of recombinant interleukin 2 on a transplantable rat fibrosarcoma by the use of a sustained release vehicle, pluronic gel," *Cancer Res.*, 47(1):37-41 (1987).

Murphy & Mooney, "Bioinspired growth of crystalline carbonate apatite on biodegradable polymer substrata," *JACS* 124:1910-7 (2002) (Abstract only).

Nakashima, "Induction of Dentine in Amputated Pulp of Dogs by Recombinant Human Bone Morphogenetic Proteins-2 and -4 with Collagen Matrix," *Arch. Or. Biol.* 39(12):1085-89 (1994) (Abstract only).

Nakashima, "Induction of dentin formation on canine amputated pulp by recombinant human bone morphogenetic proteins (BMP)-2 and -4," *J. Dent. Res.* 73:1515-1522 (1994) (Abstract only).

O'Shea et al., "Prolonged survival of transplanted islets of Langerhans encapsulated in a biocompatible membrane," *Biochem. Biophys. Acta.*, 804(1):133-6 (1984) (Abstract only).

Peppas & Langer, "New challenges in biomaterials," *Science*, 263(5154):1715-20 (1994) (Abstract only).

Pierschbacher & Ruoslahti, "Cell attachment activity of fibronectin can be duplicated by small synthetic fragments of the molecule," *Nature*, 309(5963):30-3 (1984) (Abstract only).

Polk et al., "Controlled release of albumin from chitosan-alginate microcapsules," *J. Pharm. Sci.*, 83(2):178-85 (1994) (Abstract only).

Prime & Whitesides, "Self-assembled organic monolayers: model systems for studying adsorption of proteins at surfaces," *Science*, 252(5010):1164-7 (1991) (Abstract only).

Razavi et al., "Clinical applications of a polyphosphazene-based resilient denture liner," *J. Prosthodont.*, 2(4):224-7 (1993) (Abstract only).

Ruoslahti & Pierschbacher, "New perspectives in cell adhesion: RGD and integrins," *Science*, 238(4826):491-7 (1987) (Abstract only).

Rutherford & Gu, "Treatment of inflamed ferret dental pulps with recombinant bone morphogenetic protein-7," *Eu J Or Sci*,108(3):2002-6 (2000) (Abstract only).

Rutherford, "BMP-7 gene transfer to inflamed ferret dental pulps," *Euro. J. Oral Science*, 109(6) 422-444 (2001) (Abstract only).

Rutherford, et al., "Induction of reparative dentine formation in monkeys by recombinant human osteogenic protein-1," *Arch. Oral Biol.*, 38(7):571-6 (1993) (Abstract only).

Rutherford et al., "Platelet-derived growth factor and dexamethasone combined with a collagen matrix induce regeneration of the periodontium in monkeys," *J. Clin. Periodontol.*, 20(7):537-44 (1993) (Abstract only).

Rutherford et al., "Synergistic effects of dexamethasone on platelet-derived growth factor mitogenesis in vitro, " *Arch. Oral Biol.*, 37(2):139-45 (1992) (Abstract only).

Rutherford et al., "The time-course of the induction of reparative dentine formation in monkeys by recombinant human osteogenic protein-1," *Arch. Oral Biol.*, 39(10):833-8 (1994) (Abstract only).

Rutherford et al., "Use of bovine osteogenic protein to promote rapid osseointegration of endosscous dental implants," *Int. J. Oral Maxillofac. Implats*, 7(3):297-301 (1992) (Abstract only).

Rutherford et al., "Transdentinal stimulation of reparative dentine formation by osteogenic protein-1 in monkeys," *Archs. Oral Biol.* 40: 681-683 (1995) (Abstract only).

Sawhney et al., "Interfacial photopolymerization of poly(ethylene glycol)-based hydrogels upon alginate-poly(l-lysine) microcapsules for enhanced biocompatibility," *Biomaterials*, 14(13):1008-16 (1993) (Abstract only).

Sawhney et al., "Optimization of photopolymerized bioerodible hydrogel properties for adhesion prevention," *J. Biomed. Mater. Res.*, 28(7):831-8 (1994) (Abstract only).

Schwartz & Erich, "Experimental study of polyvinyl-formal (ivalon) sponge as a substitute for tissue," *Plast. Reconstr. Surg.*, 25:1-14 (1960).

Serwer, "Agarose gel electrophoresis of bacteriophages and related particles," *J. Chromatogr.*, 418:345-57 (1987) (Abstract only).

Singhvi et al., Engineering cell shape and function. *Science*, 264(5159):696-8 (1994) (Abstract only).

Sloan et al., "Stimulation of the rat dentine-pulp complex by bone morphogenetic protein-7 in vitro," *Arch Or Biol*, 45:173-177 (2000) (Abstract only).

Smidsrod & Skjak-Braek, "Alginate as immobilization matrix for cells," *Trends Biotechnol.*, 8(3):71-8 (1990) (Abstract Only).

Soon-Shiong et al., Insulin independence in a type 1 diabetic patient after encapsulated islet transplantation. *Lancet*, 343(8903):950-1 (1994) (Abstract only).

Stern et al., "Histologic Study of artificial skin used in the treatment of full-thickness thermal injury," *J. Burn Care Rehabil.*, 11(1):7-13 (1990) (Abstract only).

Stoker et al., "Designer microenviorments for the analysis of cell and tissue function," *Curr. Opin. Cell Biol.*, 2(5):864-74 (1990).

Sun et al., "Injectable microencapsulated islet cells as a bioartificial pancreas," *Appl. Biochem. Biotechnol.*, 10:87-99 (1984) (Abstract only).

Urry et al., "Mechanochemical Coupling in Synthetic Polypeptides by Modulation of an Inverse Temperature Transition," *Proc. Nat'l Acad. Sci. U.S.A.* 85(10):3407-11 (1988).

Urry et al., "Molecular biophysics of elastin structure, function and pathology," *Ciba Found. Symp.*, 192:4-22 (1995) (Abstract only).

Urry et al., "A method for fixatiion of elastin demonstrated by stress/strain characterization," *Biochem. Biophys. Res. Commun.*, 151(2):686-92 (1988) (Abstract only).

Vacanti et al., "Selective cell transplantation using bioabsorbably artificial polymers as matrices," *J. Pediatr. Surg.*, 23(1 Pt 2):3-9 (1988).

Vainionpaa et al., "Strength and strength retention in vitro, of absorbable, self-reinforced polyglycolide (PGA) rods for fracture fixation," *Biomaterials*, 8(1):46-8 (1987) (Abstract only).

Wang, "Implantable reservoir for supplemental insulin delivery on demand by external compression," *Biomaterials*, 10(3):197-201 (1989) (Abstract only).

Yannas et al., "Synthesis and Characterization of a Model Extracellular Matrix that Induces Partial Regeneration of Adult Mammalian Skin," *Proc. Nat'l Acad. Sci. U.S.A.* 86(3):933-7 (1989).

Yannas et al., "Prompt, long-term functional replacement of skin," *Trans. Am. Soc. Artif. Intern. Organs*, 27:19-23 (1981).

Young et al., "Tissue Engineering of Complex Tooth Structures on Biodegradable Polymer Scaffolds," *J. Dent. Res.* 81(10):695-700 (2002).

\* cited by examiner

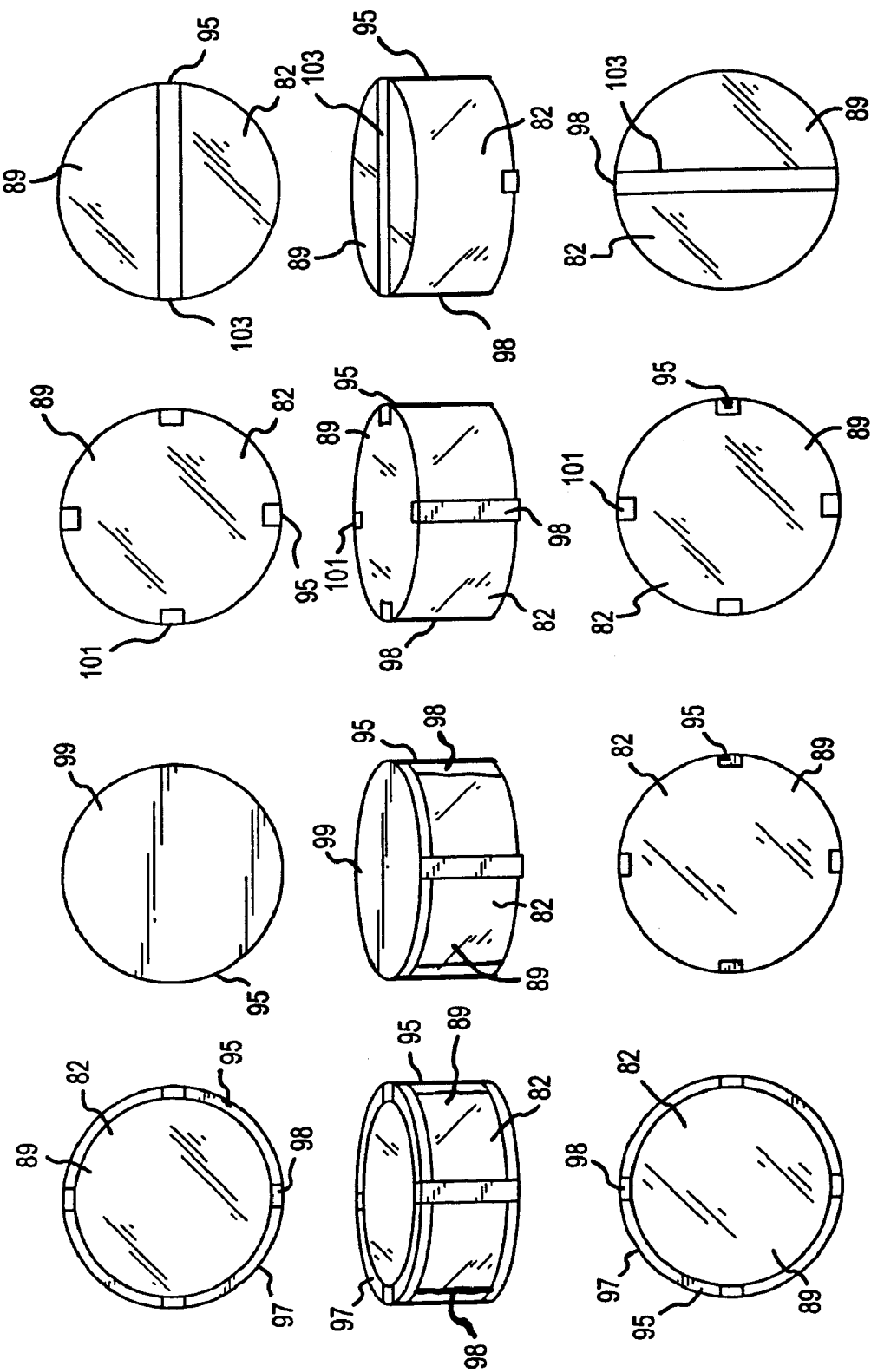

METHODS FOR TREATING DENTAL CONDITIONS USING TISSUE SCAFFOLDS

TECHNICAL FIELD

This invention relates generally to the field of treating dental conditions, particularly caries, and more particularly to methods, compositions and devices that promote in vivo regeneration and remineralization of dentin and enamel by inserting tissue scaffold materials in vivo, into holes drilled into a tooth having need of dentin regeneration.

BACKGROUND OF THE INVENTION

The development of issue scaffold materials for regenerating tissue ex vivo and for uses of such ex vivo regenerated tissue/scaffold combinations to treat patients in vivo has been a growing subject of interest in the prior art. Of relevance to the invention described hereinafter are prior art uses of tissue scaffolds for ex vivo culture of oral tissues.

U.S. Pat. No. 5,885,829 discloses use of tissue scaffolds made of a porous matrix for the ex vivo culturing and regeneration of oral tissues from isolated dental cells. Numerous polymers, both biodegradable and non-biodegradable, synthetic or natural scaffold materials were described as suitable for culturing oral tissues ex vivo. In particular, homopolymers of poly lactic acid (PLLA), poly [D,L-lactic acid] (PDLLA), poly-glycolic acid (PGA) and heteropolymers of lactic acid and glycolic acid, i.e, poly [lactic-co-glycolic acid] (PLGA), alone or in combination with polyvinyl alcohol (PVA), were shown to be effective for culturing fibroblasts isolated from dental pulp. Cells from dental pulp were first explanted, separated and propagated in a monolayer culture using ordinarily tissue culture techniques. In one exemplified method, the cultured cells were removed and then seeded onto a matrix of about 3 mm thickness made of a mat of PGA fibers. The seeded matrix was then incubated in growth medium and it was shown that the cultured fibroblasts were able to adhere to the PGA fibers and ultimately occupy the spaces between fibers. Tubular matrix scaffolds were made from porous PLLA, PDLLA and PLGA two dimensional films using a particulate leaching technique. A three dimensional tubular matrix device was constructed by stacking the films on one another and chemically sealing the edges. The tubular matrix device was shown to allow growth of vascular tissue when implanted into the mesentery and omentum of rats. Of the combinations tested, PLLA and PDLLA were shown to maintain their structure in vivo, while PLGA based devices did not. PGLA devices were determined to have less resistance against compressional forces than PLLA or PDLLA. Other techniques for forming tubular matrices were also described, including bonding of PLLA, PGA, and PLGA tubes using a chloroform spray. In another example, a three dimensional "sponge matrix" was described for a tissue scaffold formed of PLA infiltrated with PVA or of PLGA at a ratio of 85:15 D,L lactic acid:glycolic acid. These sponge devices were shown to support growth of seeded liver cells ex vivo. The devices were also implanted into the mesentery of rats with and without seeded cells and shown to support in growth of vascular tissue in vivo.

Human dental pulp cells were shown to propagate ex vivo better on a PGA matrix than on collagen or alginate based hydrogel matrices. Seeded cells grown in this manner ex vivo filled the spaces within the PGA matrix, which was eventually replaced by new tissue including tissue containing collagen indicating formation of an extracellular matrix. In another experiment, human gingival cells and pulp derived fibroblasts were shown to infiltrate a PGA matrix when seeded and cultured ex vivo, and to express human gene products when the seeded and cultured matrix was implanted subcutaneous in mice in vivo, even though the majority of cells in the implant were mouse fibroblasts. In addition it was disclosed that tissue scaffold materials could be used to deliver drugs by demonstrating that epidermal growth factor (EGF) could be entrapped in microspheres made of a 75:25 PLGA copolymer and slowly released into a buffer in vitro over 30 days. Further, hepatocyte cells seeded into cylindrical microspheres containing EGF and implanted into the mesentery of rats were shown to exhibit the biological effects of EGF on hepatocyte cellular activity over a 4 day period when implanted in vivo. Although this patent discloses a utility for using scaffold material for ex vivo propagation of oral tissues, it fails to disclose any therapeutic methods for the use of such ex vivo cultured cells for treating teeth in vivo, and fails to disclose the use of tissue scaffolds in the absence of ex vivo culturing.

U.S. Pat. No. 6,281,256 discloses a process of preparing open pore matrices of a biodegradable polymer made of PLLA, PGA or PGLA polymers by using gas forming and particulate leaching steps to form pores in the matrices of the polymers. In a typical example of the disclosed process, a PLGA copolymer is formed in a mixture that includes a leachable particulate material. The mixture is molded, optionally under compression, to a desired size and shape and is subject to a high pressure gas atmosphere to dissolve gas in the copolymer. Then a thermodynamic instability is created by reduction of the pressure so that the dissolved gas nucleates and forms gas pores within the copolymer, causing expansion and fusion of the copolymer particles, creating continuous polymeric matrix still containing the particulate material. The particulate materiel is then leached from the polymeric matrix with a leaching agent creating a porous matrix. The amount and size of the particulate material used in the mixture determines the level of interconnectivity between open pores, the size of the pores and the amount of pores in the final matrix (porosity). The interconnected matrices formed by this method have a porosity of between about 25% to 95-97% and exhibit high tensile strength with a tensile modulus of about 850 to 1100 kPa and a compression modulus of about 250 kPa or larger. Such matrices were disclosed as being useful for bone formation and guided tissue regeneration (GTR) where tissues could be grown within the matrix pores guided by the scaffolding material, which provides a surface for cellular attachment. The porous matrices could also be made to have a non-porous barrier one on end by forming an impermeable skin, or could be made of different levels of porosity throughout by altering the amount of leachable particulate material in different sections so that one section forms open pores and another does not. Such matrices where also shown to be capable of releasing a growth factor VEGF in vitro, over a period of 20 to 21 days. Use of such matrices was generally mentioned as having utility in regenerating oral tissues. The use of such matrices configured with an impermeable side was particularly suggested for treating periodontal disease by using the pores in one section of the matrix to grow periodontal ligament cells and providing a barrier in another surface of the matrix to prevent down growth of epithelial cells. However, no actual method was described for the use of such matrices in vivo without previously seeding the matrix and culturing the cells ex-vivo.

U.S. provisional patent application No. 60/166,191 describes methods for producing tissue scaffolds of PGLA using fused salt crystals of selected sizes to control the porosity, interconnectivity and ease of manufacture of the scaffolds.

U.S. Pat. No. 6,472,210 discloses a method of making a polymer scaffold having an interconnected passage-way of strutted pores with diameters in the range of about 0.5 to 3.5 mm. The polymer may be PLGA. The polymer is prepared by mixing a liquid polymer in a solution with an organic solvent such as DMSO, methylene chloride, ethyl acetated chloroform, acetone, benzene butanone, carbon tetrachloride, heptane, hexane or pentane. The liquid polymer solution is mixed with particles of 0.5 to about 3.5 mm in diameter. The particle/polymer mixture is then treated with a "non solvent" for the polymer, such as water, alcohol, dioxane or aniline, in a phase inversion step that precipitates the polymer/particle. The particle is then leached from the precipitate by treatment with a solvent that dissolves the particle material but not the polymer. The method and composition are said to be suitable for forming tissue scaffolds for use in regenerating tabecular bone, which has a high porosity and large strutted trabeculae widths on the order of about 0.14 mm to about 0.3 mm. Such large macrospores would not be suitable for regenerating dentin or other oral tissues in the teeth.

WO 00/56375 and Murphy and Mooney, (2002) J. American Chemical Society 124(9) 1910-1917, disclose methods for patterning (mineralizing) tissue scaffold material formed into three dimensional wafers for bioimplants. In one aspect, the surface of tissue scaffolds such as PGA, PLA and PLGA are coated with minerals such as calcium chloride, and phosphate useful for orthopedic tissue mineralization. The scaffold material is treated by electromagnetic radiation or by an electron beam to cause surface degradation via photolysis or electrolysis. Lithographic techniques are disclosed for forming patterns on the surface to create the desired sites of degradation. Alternatively, chemical hydrolysis of the surface or direct soaking of the scaffold material in an appropriate mineral solution may be used to pattern the wafer. In any case, the modified surface of the scaffold contains functional groups, such as polar oxygen groups (carboxylates in particular) that promote calcium phosphate formation on the surfaces of the materials used to form the scaffold materials when the treated scaffold is immersed in an appropriate solution. Osteogenic cell precursors may be seeded onto the mineralized biomaterial ex vivo. Alternatively, bone cells were said to attach to the mineralized scaffold material in vivo. The growth factor VEGF was shown to be released from such mineralized tissue scaffold materials over time. While numerous utilities of this patterning technique are disclosed, the patent fails to teach any therapeutic method that uses the patterned tissue scaffolds for a therapeutic treatment of dental conditions in vivo.

Other publications describe use of tissue scaffold material or hydrogels to deliver morphogenic agents (or genes encoding the same) that promote growth or development of various tissues in vivo after ex vivo culture. Rutherford, R. B., (2001) Euro. J. Oral Science 109(6) 422-444 disclosed that ex vivo grown dermal fibroblasts transduced with an adenovirus expression vector expressing a cDNA encoding bone morphogenic protein 7 (BMP-7) were effective at inducing reparative dentinogenesis with apparent regeneration of the dentin-pulp complex when transplanted in vivo in ferrets having pulpitis. However, no effect was seen when a 10 fold range (2.5 µg to 25 µg recombinant protein) was delivered directly to the pulp tissue. Rutherford R. B., et al (2000) Eur. J. of Oral Science 108(3) 202-206.

Sloan et. al. (2000) Archives of Oral Biology 45(2) 173-177 used a hydrogel of agarose beads soaked in BMP-7 to deliver the protein to tooth slices cultured ex vivo in a semi solid agar and disclosed a localized increase in extracellular matrix secretion by odontoblasts at the site of application. Nakashima, M., (1994) Archives of Oral Biology (12) 1085-89 demonstrated that recombinant BMP-2 and BMP-4 induced dentin formation in amputated pulp of dogs in vivo when condensed on a powdered carrier comprised of dried type 1 collagen and proteoglycans. In a prior publication, BMP-2 and BMP-4 were shown to induce dentin formation in amputated pulp when condensed on the same the same type of delivery material. Nakashima, M., (1994) J. Dental Research 73(9) 1515-1522.

Other types of materials such as various modified hydrogels also provide tissue scaffold-like functions for propagating various tissue. Anderson et al, (2002) PNAS 17; 99(19), 12025-30, disclosed that an alginate based hydrogel modified with the tripeptide sequence RGD promoted cell multiplication and bone tissue-like growth plates when chondrocytes were transplanted ex vivo.

U.S. Pat. No. 6,413,498 discloses a mixture of cationic and anionic ion exchange resins charged with $Ca^{2+}$, $F^-$ and $PO_4^{3-}$ in molar ration of 2:1:1 for use in a filler for the treatment of caries. These resins, typically made of polystyrene, promote remineralization of dentin to form tissue having a composition and hardness close to that of original dentin. Such resins are disclosed to also be useful as components of dentifrice products are not suitable as a tissue scaffold to promote regeneration of the cell types that are required for healthy dentin. Moreover, such resins are believed to leave organic residue upon contact with teeth.

U.S. Pat. Publication No. 2002/0119180 A1 and Young et al., (2002) J. Dent. Res. 81[10] p 695-700 each describe regenerating multiple dental tissues in organized tooth structures in situ by ex vivo seeding of enamel and pulp organ tissues on a PGA/PLLA or PLGA scaffold formed in the shape of a human teeth. The ex vivo cultured tissue/scaffold combinations were collagen coated and then implanted in the omentum of rats were they were cultured in situ. The in situ cultured tissue were shown to develop mineralized structures indicative of enamel surrounding dentin, and to develop into odontogenic cell types, including, ameloblasts, odontoblast-like cells, putative cemetoblasts and cementum. While the experiment demonstrated the potential feasibility of regenerating whole teeth by ex vivo seeding and in vivo culturing of isolated dental tissue, Young et al, however, did not disclose any method of treating dental tissue in vivo.

While the prior art recognizes the utility of using tissue scaffolds for growing tissue in vitro or for treating bone lesions in vivo, there remains a need in the art for methods and devices for treating dental conditions in vivo using such tissue scaffold. The present invention provides for such methods and devices.

SUMMARY OF THE INVENTION

The present invention provides methods, compositions and devices based on the discovery that tissue scaffolding materials can be directly used to facilitate regeneration of dentin in a tooth of subject in vivo, without need of seeding of the scaffold material by ex vivo culture of cells prior to implanting the scaffold material into dental tissue. In the methods of the invention, the scaffolding material is used as a substitute or as an enhancement of prior art methods for treating various stages of dental caries or pulpitis. The methods are suitable for treating conditions ranging from asymptomatic caries where only a small portion of dentin below the crown of the tooth is degenerated, to treating deep caries where dentin is degenerated down to the root ordinarily requiring a root canal treatment by the methods of the prior art. The methods apply the scaffolding material directly into appropriately sized holes drilled into a subjects teeth so that at least a portion of the pulp is exposed. The scaffolding material is implanted into the hole so that a portion of the scaffold material is in contact with the exposed portion of the pulp. Pulp cells are stimulated to grow into the matrix of the scaffolding material causing remineralization and formation of new dentin.

More particularly, one aspect of the invention is a method for treating a subject's tooth in need of regeneration of dentin that includes the acts of forming a hole in the tooth of the subject in vivo, the hole being of a depth sufficient to expose at least a portion of pulp, inserting a tissue scaffold into the hole so that a portion of the tissue scaffold contacts at least a portion of the exposed pulp; and regenerating dentin by allowing sufficient time for tissue to grow in vivo, from the pulp into the tissue scaffold and to regenerate the dentin. In certain embodiments, the invention the tissue scaffold inserted into the hole does not include an ex vivo cultured tissue within the scaffold. In other embodiments, dental pulp stem cells are seeded into the tissue scaffold and cultured therein prior to insertion of the tissue scaffold into the hole. In still other embodiments, dental pulp stem cells are added directly to the region of the exposed pulp prior to inserting the tissue scaffold into the hole.

In certain embodiments, the tissue scaffold is formed into a shape dimensioned to fit snuggly into the hole that is formed so that the tissue scaffold does not move more than 0.1 mm in a lateral direction in the hole. The tissue scaffold is typically formed into a cylindrical wafer having a diameter of about 2 to about 5 mm and a height of about 0.5 to about 2 mm.

In various embodiments, the tissue scaffold also contains calcium phosphate associated therewith. In particular embodiments the tissue scaffold also contains fluoride associated therewith.

In certain embodiments, the tissue scaffold is comprised of scaffolding material selected from the group consisting of PLA, PGA, PDLLA PLLA and PLGA. In a particular embodiment, the tissue scaffold is comprised of scaffolding material is comprised of PLGA.

In certain embodiments, the tissue scaffold may further include a physiologically effective amount of a morphogenic agent that promotes growth of dentin tissue or the mineralization thereof. In particular embodiments, the morphogenic agent is selected from a protein encoded by a TGF-β supergene family. In more particular embodiments, the protein is selected from the group consisting of BMP-2, BMP 4, BMP-7, VEGF, FGF-1, FGF-2, IGF-1, IGF-2, PDGF, GDF-1, GDF-2, GDF-2, GDF-3, GDF-4, GDF-5, or combinations of the same. In still more particular embodiments the protein is selected from the group consisting of BMP-2, BMP 4, BMP-7, and GDF-5. In yet another more particular embodiment, the morphogenic agents includes at least one of PDGF VEGF, and a protein selected from the group consisting of BMP-2, BMP 4, BMP-7, and GDF-5.

In certain embodiments, the tissue scaffold further includes an active agent selected from the group consisting of an anti-bacterial agent, an anti-inflammatory agent, and an analgesic agent. Example antibiotics include antibacterial agents such as tetracycline. Example anti-inflammatory agents include COX I and II inhibitors. Example analgesic agents include anti-inflammatory and anaesthetic agents.

In certain embodiments, the methods of the invention may include covering the hole with a cement. In particular embodiments the cement may be comprised of a combination of di-calcium and tetra-calcium phosphate. In certain other embodiments, the cement or amalgam is comprised of calcium phosphate and fluoride.

In one embodiment of the methods of the invention, the subject has asymptomatic caries and the act of forming the hole exposes a portion of the pulp located in a coronal cap region of the tooth and the tissue scaffold is inserted to contact the exposed pulp. In another embodiment, the subject has need of a pulpotomy and the act of forming the hole exposes a portion of the pulp located in a coronal region of the tooth and the tissue scaffold is inserted into the coronal region to contact the exposed pulp. In another embodiment, the subject has need of a root canal and the act forming the holes exposes a portion of the pulp in at least one of the root canal, and a coronal region of the tooth and the tissue scaffold is inserted into the hole to contact the exposed pulp.

In another aspect, the invention includes devices for treating a tooth that include a tissue scaffold comprised of a scaffolding polymer configured as a wafer that fits snuggly into a corresponding hole that is formed in a tooth of the subject so that the tissue scaffold does not move more than 0.1 mm in a lateral direction in the hole. In certain embodiments, the hole of corresponding size is formed by an act of drilling the tooth. In some embodiments the wafer is cylindrical and has a diameter of about 2 to about 5 mm and a has height of about 0.1 to about 0.5 mm.

In yet another aspect, the invention provides compositions for treating dental tissue that include: a tissue scaffold comprising a scaffolding material associated with calcium phosphate and fluoride. The composition may further comprise a physiologically effective amount of a morphogenic agent that promotes growth of dentin tissue. In particular embodiments, the morphogenic agent is selected from a protein encoded by a TGF-beta supergene family. In more particular embodiments, the protein is selected from the group consisting of BMP-2, BMP 4, BMP-7, VEGF, FGF-1, FGF-2, IGF-1, IGF-2, PDGF, GDF-1, GDF-2, GDF-2, GDF-3, GDF-4, GDF-5, or combinations of the same. In still more particular embodiments the protein is selected from the group consisting of BMP-2, BMP 4, BMP-7, and GDF-5. In yet another more particular embodiment, the morphogenic agents includes at least one of PDGF VEGF, and a protein selected from the group consisting of BMP-2, BMP 4, BMP-7, and GDF-5. The composition may further comprise an active agent selected from the group consisting of an anti-bacterial agent, an anti-inflammatory agent, and an analgesic agent. The composition may include an active agent selected from the group consisting of an anti-bacterial agent, an anti-inflammatory agent, and an analgesic agent. In typical embodiments, the composition is comprised of scaffolding polymer selected from the group consisting of PLA, PGA, PDLLA PLLA and PLGA. In preferred embodiments the scaffolding polymer is PLGA.

In some embodiments the device is made of a scaffolding material selected from the group consisting of PLA, PGA, PDLLA PLLA and PLGA. In some embodiments the scaffolding material is associated with calcium phosphate. In some embodiments the wafer is associated with calcium phosphate and fluoride. The device may further include a pharmaceutically acceptable carrier, buffer, excipient or diluent.

In some embodiments, the device has a top surface, a bottom surface and a side perimeter surface between the top and bottom surfaces, and at least one of the top and bottom surfaces are marked with a pattern that alters appearance when the wafer is crushed. In one embodiment the pattern is comprised of set of concentric circles. In another embodiment, the pattern is comprised of a dye that alters color when the wafer is compressed.

In another aspect, the invention provides a kit containing a plurality of the forgoing wafers wherein the plurality of wafers are of a plurality of sizes selected to correspond with a plurality of hole sizes. The plurality of hole sizes correspond to a plurality of holes made by drilling a tooth with any one of a plurality of dental drill bit sizes. In one embodiment, the kit includes, a dry tissue scaffold wafer dimensioned to be received into a hole of corresponding size formed in a tooth of a subject and a well configured to hold the tissue scaffold wafer in a dry state. Also included is a second well adjacent to the first well, the second well holding a hydrating liquid comprising a pharmaceutically acceptable liquid. A breakable partition separates the first and second wells, the breakable partition being structured to break by a force applied by a human hand causing the tissue scaffold wafer to contact hydrating liquid when the breakable partition is broken.

In yet another aspect, the invention provides a support casing to protect tissue scaffold from crushing. The casing a least partially surrounds the tissue scaffold wafer. The tissue scaffold wafer is made of a porous scaffolding material having a first crushing resistance and the support casing is made of a material having a second crushing resistance greater than the first crushing resistance. In a typical embodiment, the support casing includes at least one horizontally disposed member that contacts at least one of an upper and lower surface of the tissue scaffold wafer and includes at least one columnar extension extending from the horizontally disposed member along a side perimeter of the tissue scaffold wafer.

Yet another aspect of the invention provides a vacuum manipulator for manipulating a tissue scaffold wafer. The vacuum manipulator includes a vacuum tube having a proximal end, a distal end, and walls between the proximal and distal ends enclosing the vacuum tube. The manipulator includes an attachment for a vacuum source in fluid communication with the vacuum tube; and a suction cup attached to the proximal end of the vacuum tube in fluid communication with the vacuum tube. The suction cup is sized to fit onto a surface of a wafer comprised of dental scaffolding material. The manipulator also includes a valve assembly at the distal end of the vacuum tube, the which is operable to close and open fluid access between the vacuum tube and a vacuum source and to open and close fluid access between the vacuum tube and a pressure source.

BRIEF DESCRIPTION OF THE DRAWINGS

FIG. 3A shows concentric markings. FIG. 3B shows perpendicular hatch markings. FIG. 3C shows parallel line markings. FIG. 3D shows dot markings.

FIGS. 4A-4D illustrate various tissue scaffold wafer casing supports according to another aspect of the invention. FIG. 4A shows a ring support. FIG. 4B shows a pad support. FIG. 4C shows a bracket support. FIG. 4D shows a brace support.

DETAILED DESCRIPTION OF THE INVENTION

Figure 1:
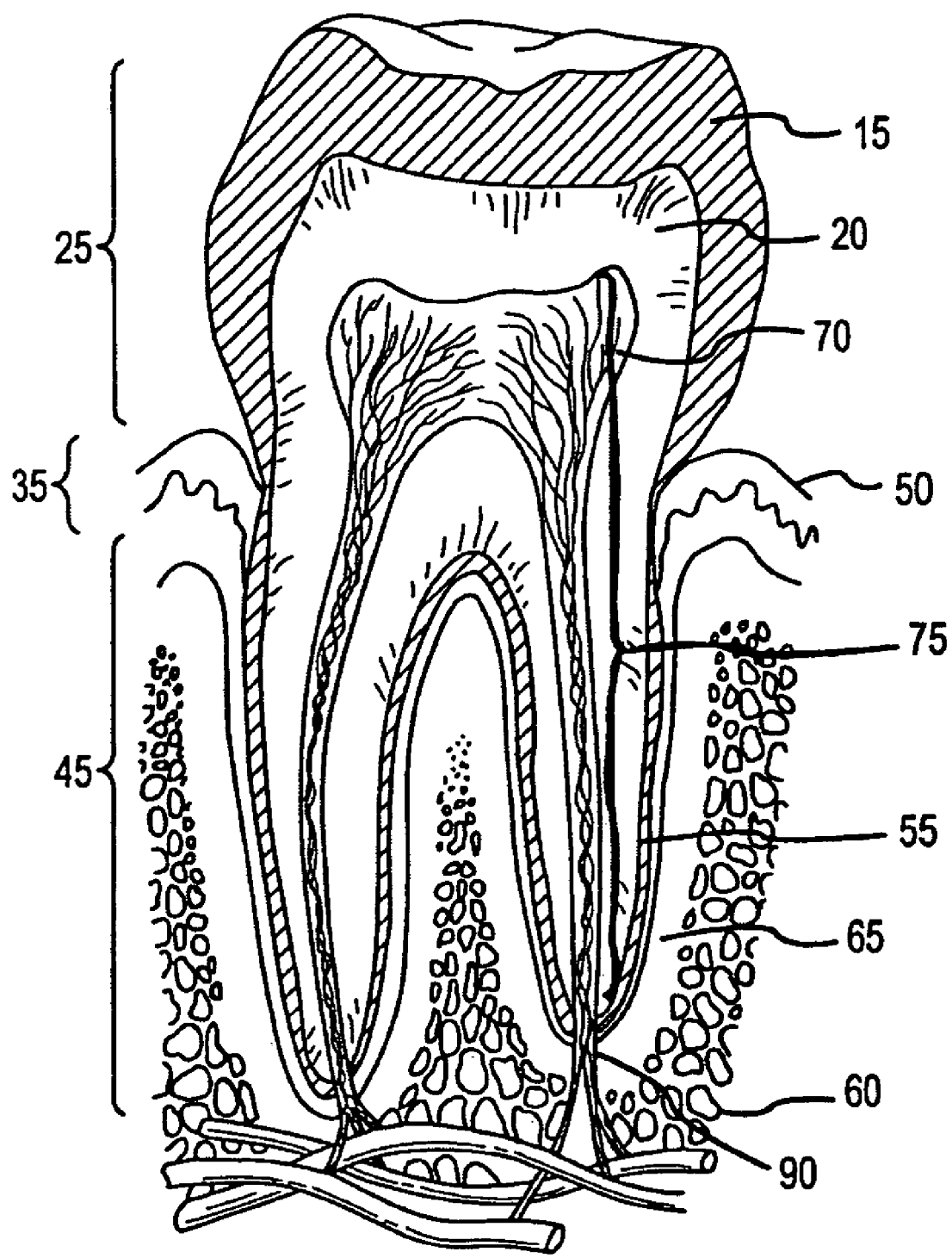
FIG. 1 illustrates tooth anatomy for reference to various aspects of the invention.

In the description that follows, citation is made to numerous references that may aid one of ordinary skill in the art to understand or practice of the invention in its fullest scope. Each such reference, as well as the references cited therein, is incorporated herein by reference to the extent needed to practice the methods or make the materials of the present invention, and to the extent such references do not conflict with the teachings of this invention, in which case the teachings of this invention are to be used to substitute or supplement such conflicting teachings in the incorporated references.

Abbreviations and Definitions

Prior to setting forth the invention in detail, certain terms are defined herein below as better aid in an understanding thereof. The definitions below are not intended to limit the ordinarily meaning of the terms as they would be understood by one of ordinary skill in the art, except if the ordinary meanings would conflict with the meanings set forth below. Otherwise, the definitions are intended to illustrate various aspects of the ordinarily understood meanings:

"Biodegradable" with respect to a composition or device means the composition or device may be eroded, absorbed, digested, destroyed, reconfigured, removed or otherwise degraded from its original form when placed into contact with a selected animal tissue or fluid in vivo for a period of 30 days or less. The animal tissue or fluid may or may not include flora such as bacteria, fungi or other microbe that facilitates the degradation. The typical tissue or fluid involved in biodegradation includes any oral or dental tissue or part thereof. If the composition or device remains substantially in its original form after 30 days of in vivo contact with animal tissue, it is herein considered "non-biodegradable".

A "tissue scaffold" is any composition formed into a porous matrix into which tissue can grow in three dimensions. Tissue scaffolds of the present invention are at least 60% porous, at least 70% porous, at least 80% porous, at least 90% porous, or at least 97% porous, where porosity is a measure of the volume of liquid, gas or void per volume of solid material in the matrix. The pore size of suitable tissue scaffolds should be at least about 50 microns, at least about 100 microns and preferably at least about 150 microns, where pore size is roughly the average size of the largest dimension of the pores in the matrix.

A "hydrogel" is any porous matrix, including tissue scaffolds, where the pores are filled with a liquid. A hydrogel differs from a tissue scaffold in that a hydrogel may have a porosity of less than 60% and/or a pore size of less than 50 microns and cells typically do not grow within such hydrogels of low porosity, although they may grow on the surface of the same. While tissue scaffolds may be used as hydrogels in certain embodiments of the invention, in the typical embodiments, the hydrogel has a lower porosity and/or pore size as mentioned. Hydrogels may be made of the same scaffolding materials as tissue scaffolds, or other materials including but not limited to agars, agaroses, alginates, collagens, acrylamides, celluloses, starches, methacrylates and the like.

"Scaffolding polymers" or "scaffolding materials" are the materials used to make tissue scaffolds. The terms refer to both monomeric units of the materials and the polymers made therefrom. Scaffolding polymers may be biodegradable or non biodegradable. Suitable examples of biodegradable and non-biodegradable scaffolding polymers useful in the practice of the invention are found in the description that follows, in the references incorporated herein, and in the references cited in the incorporated references.

A "wafer" is a tissue scaffold formed into any suitable shape for implantation into the tooth of a subject. Suitable wafer shapes include, but are not limited to microspheres, tubular barrels, concentric tubes, spiral tubes, cylindrical sponges, overlaying mats and the like.

A "hole of corresponding size" and "wafer of corresponding size" refer to an indentation (hole) and a tissue scaffold wafer respectively, each of a selected size, where the hole is formed in a tooth by a hole-forming process such as drilling, and the size of the hole is such that the scaffold wafer of selected size, when properly oriented, will fit into the hole with a movement tolerance in a lateral direction of about 0.01 to 0.5 mm and more preferably about 0.01 to about 0.1 mm.

Tooth Anatomy

A better understanding of the invention may be had with reference to basic tooth anatomy as illustrated in FIG. 1. The tooth includes a crown region 25 located above the gum 50, a neck region 35 in the vicinity of the gum 50, and a root region 45 located beneath the gum 50. Enamel 15 covers the crown 25 of the tooth. Cementum 55 anchors the tooth in the bone 60 through the periodontal ligament 65. Dentin 20 is the microscopically porous hard tissue under the enamel 15 and the cementum 55 and is comprised of a combination of a porous mineral matrix and living cells. Pulp tissue 70 is located beneath the dentin 20 in a pulp chamber that has a coronal region and a radicular (root canal) region 75 ending at the foramen (hole) 90 at the end of the root where the pulp tissue 70 becomes continuous with the periodontal ligament.

The dental pulp 70 consists of loose connective tissue derived from ectomesenchymal cells and is confined within the coronal region and root canals 75 of the tooth. The pulp 70 contains cells that provide odontogenic, nutritive, sensory, and defensive functions to the mature pulp 70 and allows for preservation of vitality during normal homeostatic maintenance and during wound repair after injury.

The mature dental pulp 70 can be divided into two compartments: The odontogenic zone and the pulp proper. The odontogenic zone includes the odontoblasts, which are the cells responsible for the production of predentin and dentin, the cell-free zone, the cell-rich zone, and the parietal plexus of nerves. The pulp 70 proper includes the majority of the remaining area of the pulp and consists primarily of fibroblasts and extracellular matrix, blood vessels, and nerves. As the pulp 70 ages, its volume decreases with a corresponding increase in dentin thickness. Numerous studies have demonstrated that the dental pulp 70 has an inherent capacity to respond to wounding in the absence of other inflammatory insults.

The most predominant cell type in the dental pulp 70 is the fibroblast, but the pulp also contains odontoblasts, blood cells, Schwann cells, endothelial cells, pericytes and undifferentiated mesenchymal cells. Cells involved in the immune response, such as macrophages, mast cells, antigen processing cells (dendritic cells), and plasma cells can also be found in the pulp during periods of inflammation.

Odontoblasts are terminally differentiated, polarized pulpal cells derived from the cranial neural crest, which are found in a peripheral layer closely associated with the predentin. The major function of odontoblasts is production of unmineralized [predentin] and mineralized dentin matrices.

The cell bodies form an irregularly columnar, epithelial-like layer on the inner aspect of the dentin. The proximal surface of the cell body is adjacent to pulp cells, and the distal extremity is tapered and embedded in predentin, an unmineralized layer of dentin-like material as well as within tubules in the mineralized dentin.

The major protein produced by the odontoblast is type I collagen and is secreted into the extracellular space at the predentin interface. Non-collagenous components of the extracellular matrix of predentin and dentin, including proteoglycans, glycosaminoglycans, phosphoproteins, and γ-carboxyglutamate-containing proteins, are also synthesized and secreted by odontoblasts.

Functioning odontoblasts continue to produce predentin throughout the life of the tooth. Odontoblasts retain the ability to upregulate protein synthetic activity in response to trauma after aging.

The remainder of the pulp 70 consists of a "stromal" tissue containing nerves, blood vessels, and lymphatics. The stromal tissue is composed of cells and extracellular material. There appears to be only one type of cell, resembling mesenchyme but capable of producing extracellular material, including collagen. Thus, the cell can equally be termed a fibroblast, or simply a pulpal cell.

Fibroblasts are the most numerous cells found in the dental pulp 70. They are stellate-shaped cells with long cytoplasmic extensions that contact adjacent fibroblasts or odontoblasts through gap-junctional processes. Fibroblasts synthesize and secrete type I and type III collagen, and other ECM components of the pulp, including proteoglycans and glycosaminoglycans. Collagen is the most abundant connective tissue protein and occurs in several specific isotypes, types I through XII. Each is recognized as a specific genetic product differing in amino acid and polypeptide composition. In the pulp 70, type I and type III are the most abundant, with other types, such as IV and V being minor constituents.

Fibroblasts or undifferentiated mesenchymal cells also have an important role in wound healing mechanisms in the pulp 70. The fibroblasts of the cell-rich zone are thought to differentiate into odontoblasts after the right stimulus—for example, growth factor, a bone morphogenic protein (BMP), a cytokine, or an inflammatory mediator, typically released during wounding from the exposed predentin or dentin, or from inflammatory cells that have migrated to the wound site.

There are many other cells found in a vital dental pulp 70. Perivascular (a.k.a pericytes) cells are found in the dental pulp closely associated with the vasculature. These cells have been reported to be important in wound-healing mechanisms associated with pulpal repair mechanisms. Perivascular cells have also been shown to proliferate in response to an iatrogenic exposure of the dental pulp, and are thought to possibly provide replacement cells for the odontoblast layer in wounds where the cell-rich layer has been destroyed.

Endothelial cells line the lumen of the pulpal blood vessels and contribute to the basal lamina by producing type IV collagen, an afibrillar collagen. They have been shown to proliferate after a pulp exposure in an attempt to neovascularize the wounded area during the process of wound healing.

Class II antigen processing cells have been demonstrated by immunohistochemical methods in both the normal and inflamed pulp. Other vascular-derived cells found in the pulp during an inflammatory condition include mast cells, B- and T-lymphocytes, polymorphonuclear neutrophils, and macrophages. These blood cells are of paramount importance in fighting infection in the pulp because of the substances they contain: histamine, serotonin, cytokines, growth factors, and other cellular mediators. Schwann cells can also be found, which cells envelope nerve processes with a myelin sheath.

Dentin 20 forms the bulk of the tooth. It is lined on its outer aspect by enamel 15 on the crown 25 and by cementum 55 on the root 90. The youngest layer of dentin 20 formed at any particular time is adjacent to the junction between the odontoblast cell body and its major process. This layer of young dentin 20 is essentially unmineralized, and ends abruptly in contact with the mature dentin. Mature dentin 20 is associated with glycoproteins, an increased diameter of the collagenous fibrils, and a sudden and dramatic mineralization related to these fibrils.

The outer surface of the root canal 75 is covered by a relatively thin layer of the bone-like mineralized cementum 55. The cementum 55 is made of a matrix of calcified collagenous fibrile, glycoproteins, and mucopolysaccharides. The outermost layer of cementum 55 is an uncalcified precementum produced by the discontinuous layer of irregularly shaped cementoblasts.

The present invention is based on recognizing that one or more of the above tissue types are involved in regenerating dentin 20 and that contacting viable pulp tissue 70 with a tissue scaffold in vivo, especially in combination with a morphogenic agent such as BMP-2, BMP-4 or BMP-7, will initiate appropriate cell infusion into the tissue scaffold and ultimately result in cell proliferation as well as remineralization and regeneration of the dentin 20 and pulp 70.

Tissue Scaffolds Generally

The tissue scaffolds used in the present invention provide a matrix for the cells to guide the process of tissue formation in vivo in three dimensions. Although the majority of mammalian cell types are anchorage dependent and will die if not provided an adhesion substrate, the tissue scaffolds of the present invention are not simply an adhesion substrate. Petri dishes and other non-tissue scaffold structures are generally used in cell culture, whereby cell monolayers result, however, this does not lead to tissue regeneration. It will be understood that simple dishes, vials and other receptacles are not "tissue scaffolds" in the context of the present invention, although it is possible that the materials from which they are formed may be adapted for this purpose by design and/or by combination with other tissue scaffold elements.

The materials utilized to fabricate a tissue scaffold for use in the present invention can generally be categorized into three types: (1) naturally derived materials, including ECM molecules, such as collagens and hyaluronic acid, (2) polysaccharides, such as alginate, agars, agaroses and the like that can be formed into hydrogels of sufficient porosity to serve as tissue scaffolds, and (3) bio compatible synthetic materials including any of a variety of polymers or co-polymers, whether biodegradable or non-biodegradable, that do not elicit adverse affects when implanted into tissue.

(1) Naturally-Derived Tissue Scaffolds

Any one of a variety of naturally-derived tissue scaffold-like materials may be used to provide a framework for tissue growth in accordance with the present invention. Because the tissue scaffold, or substantial portions thereof, are applied to a hole drilled in a subjects tooth, one will generally prefer to use a tissue scaffold that is derived from a biological tissue that is compatible with the tooth. Such biocompatibility requires that the tissue scaffold does not cause any significant adverse or untoward reactions when administered to the subject. By using a biocompatible tissue scaffold significant immune responses and inflammatory reactions will be avoided.

A large number of naturally-derived tissue scaffold-like materials are available that may be used as tissue scaffolds in accordance with this invention, including those tissue scaffolds fabricated from human, animal or plant tissue. Potential advantages of these types of materials are their biocompatibility and their biological activity. As many of these molecules are found within tissues, they may not induce any foreign body reactions and are presumably receptive to the cell-mediated remodeling that occurs during tissue repair and regeneration (Murphy et al., 1990; Yannas et al., 1989).

ECM molecules, such as collagen may be used as tissue scaffold materials in certain practices of the invenit. Type I collagen, the most prevalent ECM molecule in the body, is readily isolated from animal tissues and has been extensively utilized to fabricate cell delivery devices (Green et al., 1979; Yannas et al., 1981; Bell et al., 1981; Stern et al., 1990; Cavallaro et al., 1994). This material can be processed into a wide variety of structures for use in the invention, e.g., films, sponges and fibers (Green et al., 1979; Yannas et al., 1981; Bell et al., 1981; Stern et al., 1990; Cavallaro et al., 1994). The structure and resultant mechanical properties of collagen-based scaffolds can be regulated by the process utilized to extract the collagen from tissues (Cavallaro et al., 1994), and by various crosslinking processes. Collagen molecules may be crosslinked physically by dehydrothermal (Koide et al., 1993) or UV radiation treatments, or chemically by using various chemical agents (Cavallaro et al., 1994; Koide et al., 1993; DeLustro et al., 1990). However, the inflammatory response to these materials and their erosion rate are dependent on the specific cross-linking agent that is utilized (Cavallaro et al., 1994; Anselme, 1992; Koide et al., 1993).

Suitable collagen tissue scaffolds are described, for example, in U.S. Pat. Nos. 4,347,234; 4,390,519; 4,394,370; 4,409,332; 4,538,603; 4,585,797; 4,703,108; 4,837,285; 4,975,527; 5,081,106; 5,128,136; 5,162,430; 5,197,977 and 5,206,028. Mineralized collagen, as disclosed in U.S. Pat. No. 5,231,169 may also be used in the present invention.

Type I collagen may also be combined with glycosaminoglycans to form gels which mimic native dermal tissue (Yannas et al., 1981; Stern et al., 1990; Heimbach et al., 1988). A variety of other ECM molecules, including laminin (Dixit, 1994; Guenard et al., 1992), have been utilized as cell delivery tissue scaffolds, and any such tissue scaffold may be used in the context of the present invention.

(2) Polysaccharides

Polysaccharides may also be used as tissue scaffolds in accordance with this invention. Alginate, a polysaccharide isolated from seaweed, has previously been used as a cell delivery vehicle. Water soluble sodium alginate readily binds calcium, forming an insoluble calcium alginate hydrocolloid (Sutherland, 1991). These gentle gelling conditions have made alginate a popular material to encapsulate cells for transplantation (Lim and Sun, 1980; O'Shea et al., 1984; Ricordi et al., 1988; Sullivan et al., 1991; Lacy et al., 1991; Levesque et al., 1992; Soon-Shiong et al., 1994; Dixit, 1994; Kasai et al., 1994), and as an injectable cell delivery vehicle (Atala et al., 1994).

The potential advantages of these natural materials have made them popular for fabricating tissue engineering tissue scaffolds, and they may certainly be used in the context of the present invention. However, these materials also have a number of disadvantages. Many of these materials are isolated from human or animal tissue, and are not available in large quantities. They suffer from large batch-to-batch variations, and are typically expensive. Additionally, these materials exhibit a limited range of physical properties (e.g., mechanical strength, erosion times). These drawbacks led the present inventors to contemplate using synthetic materials to fabricate tissue scaffolds for use in many aspects of this invention.

(3) Synthetic Tissue Scaffolds

Synthetic polymers are attractive scaffold materials as they can be readily produced with a wide range of reproducible properties and structures. Polymer tissue scaffolds also provide mechanical support against compressive and tensile forces, thus maintaining the shape and integrity of the scaffold in the environment of the tooth.

The morphology of the tissue scaffold can guide the structure of an engineered tissue (Vacanti et al., 1988), including the size, shape and vascularization of the tissue (Mooney et al., 1994a, 1994b, 1995b, 1996a). The proper design of these tissue scaffolds allows them to exhibit the required range of mechanical and biological functions. Synthetic polymeric materials can be precisely controlled in material properties and quality. Moreover, synthetic polymers can be processed with various techniques and supplied consistently in large quantities. The mechanical and physical properties of synthetic polymers can be readily adjusted through variation of molecular structures so as to fulfill their functions without the use of either fillers or additives. Table 1 outlines different structural factors of polymers that can be used to adjust a variety of critical properties.

A variety of synthetic biodegradable polymers can be utilized to fabricate tissue scaffolds. In general, these materials are utilized as structural elements in the scaffold. Poly(glycolic acid) (PGA), poly(lactic acid) (PLA), Poly lactic co-lactic acid (PLLA) and poly(lactic acid)-poly(glycolic acid) (PLGA) polymers are commonly used synthetic polymers in tissue engineering. These polymers are also extensively utilized in other biomedical applications such as drug delivery and are FDA approved for a variety of applications (Huang, 1989).

A number of PGA, PLA, PLLA and PLGA and other synthetic polymer tissue scaffolds are known in the art, and are further described herein, any one or more of which may be used in the context of the present invention. By way of example only, one may mention the PGA, PLA and PLGA formulations disclosed in any of: U.S. published applications No. 2002/0119180A1, 2003/0031696 or U.S. Pat. Nos. 6,281,256, 6,472,210, 5,885,829, 5,366,734; 5,366,733; 5,366,508; 5,360,610; 5,350,580; 5,324,520; 5,324,519; 5,324,307; 5,320,624; 5,308,623; 5,288,496; 5,281,419; 5,278,202; 5,278,201; 5,271,961; 5,268,178; 5,250,584; 5,227,157; 5,192,741; 5,185,152; 5,171,217; 5,143,730; 5,133,755; 5,108,755; 5,084,051; 5,080,665; 5,077,049; 5,051,272; 5,011,692; 5,007,939; 5,004,602; 4,961,707; 4,938,763; 4,916,193; 4,898,734; 4,898,186; 4,889,119; 4,844,854; 4,839,130; 4,818,542; 4,744,365; 4,741,337; 4,623,588; 4,578,384; 4,568,559; 4,563,489; 4,539,981; 4,530,449; 4,384,975; 4,300,565; 4,279,249; 4,243,775; 4,181,983; 4,166,800; 4,137,921.

Where a tissue scaffold is to be administered to an oral tissue site, another reason for preferring a synthetic material is that the surface properties of synthetic materials can be easily and reproducibly altered, as necessary. Plasma modification and grafting of relatively inert substances, such as polyethylene oxide or polyvinyl alcohol, can mask the chemistry of the bulk tissue scaffold (Peppas and Langer, 1994). The specific structure of adsorbed polymer coatings can be controlled by varying the chemical structure and molecular weight polydispersity of the coating polymer (Dan and Tirrell, 1993). Molecular self-assembly strategies can also be used to define the protein and cellular interactions with material surfaces (Prime and Whitesides, 1991; Singhvi et al., 1994).

TABLE 1

Structural Variables used to Control Properties of Synthetic Biodegradable Polymers

| Variables | Effects | Examples |
|---|---|---|
| Incorporation of both natural and/or non-natural monomers | May reduce/eliminate immunologic response often found in naturally-derived polymers | Non-immunologic PGA and PLA (vs. collagens) |
| Incorporation of labile groups in polymer chain | Control kinetics of biodegradation | Hydrolyzable ester bond in PGA |
| Incorporation of functional groups in side chains | Control chemical and physical properties of polymers | Hydrophilic, hydrophobic and amphiphilic polyphosphazenes |
| Incorporation of chiral centers in polymer chains | Control physical and mechanical properties of polymer | Semi-crystalline L-PLA and amorphous D,L-PLA |
| Possibility of utilizing multiple monomers | Control properties of polymers | Glycolic and lactic acids PLGA |
| Use of natural compounds as monomers | Biocompatible break-down products | Lactic acid in PLA |
| Use of different polymer architectures | Control physical and mechanical properties of polymers | Branched polymers exhibit lower viscosity than-linear ones |

Adapted from Wong and Mooney, 1997.

3a Biodegradable Tissue Scaffolds

Tissue scaffolds fabricated from biodegradable materials will erode over time in the body to yield a completely natural tissue. These tissue scaffolds will not induce any chronic inflammatory responses, and cannot serve as a long-term site for infection. Biodegradable polymers have been utilized to engineer tissues ex vivo that will be structurally integrated with the host tissue (Langer and Vacanti, 1993; Heimbach et al., 1988; Hansbrough et al., 1992; Mooney et al., 1994a; 1994b; 1995a; 1995b; 1996a; Johnson et al., 1994; Dixit, 1994; Kasai et al., 1994; Mooney and Vacanti, 1993). In addition, the use of synthetic, biodegradable tissue scaffolds will often be advantageous as the degradation time of such synthetic tissue scaffolds can be designed to coincide with the formation of a new tissue from the cultured cells.

While there are a variety of biodegradable polymers (Gilding, 1981; Peppas and Langer, 1994), polymers composed of monomers naturally present in the body (e.g., lactic acid, alpha.-amino acids) are preferred for use in certain aspects of the invention. These form aliphatic polyesters of the poly($\alpha$-hydroxy acids) with the general formula—>— O—CH(R)—CO—!—which derive from corresponding HO—CH(R)—COOH where R=H in the case of glycolic acid (GA) and R=CH3 in the case of lactic acid (LA), the latter being chiral, i.e., D- or L-isomer is possible. These polymers have been used in bone osteosynthesis and reconstruction (Vert et al., 1984) and in drug delivery (Gombotz and Pettit, 1995).

Polymers of lactic acid, glycolic acid, and copolymers of the two have been utilized to fabricate tissue engineering tissue scaffolds (Heimbach et al., 1988; Hansbrough et al., 1992; Mooney et al., 1994a; 1994b; 1995a; 1995b; 1996a; Johnson et al., 1994; Mooney and Vacanti, 1993). These polymers are readily processed into a variety of configurations, including fibers (Frazza and Schmitt, 1971), porous sponges (Mooney et al., 1995a; Mooney and Vacanti, 1993) and tubular structures (Mooney et al., 1995b).

The regular structure of homopolymers of lactic and glycolic acid results in a crystalline structure (Gilding, 1981). Copolymers containing significant quantities of both monomers are amorphous (Gilding, 1981). This polymer family's widely varying mechanical and erosion properties (Table 2) results both from the varying crystallinity, and the differing hydrophobicity of lactic and glycolic acid (Gilding, 1981). Example tissue scaffolds with a variety of degradation times and mechanical properties suitable for the present invention are listed in Table 2

TABLE 2

Typical Yield Stress Values and Erosion Times for Polymers of Lactic and Glycolic Acid

| POLYMER | YIELD STRESS (Kpsi)* | TIME FOR 50% EROSION (weeks) |
|---|---|---|
| polyglycolic acid | 11.2 | 4 |
| 50/50 poly (D,L-lactic-co-glycolic acid) | 7.7 | 6 |
| 85/15 poly (D,L-lactic-co-glycolic acid) | 6.3 | 20 |
| poly (D,L-lactic acid) | 6.6 | 35 |
| poly (L-lactic acid) | 8.5 | 56 |

Adapted from Wong and Mooney, 1997.
*Values represent the mean of 5 measurements obtained using Instron. Data is adapted from Medisorb (Cincinnati, OH).product data.
**The time at which ½ of the polymer has eroded(Polymer mass = ½ initial mass) following immersion in a buffered saline solution maintained at 37.degree. C.

PGA and PLA can be prepared by two different routes, namely, polycondensation and ring opening polymerization (ROP). Generally, the simple polycondensation is less expensive, but the resulting polymers have low and uncontrolled molecular weight and it is difficult to prepare copolymers (Gilding and Reed, 1979, Kricheldorf and Kreiser-Saunders, 1996). It is believed that the antimony trioxide catalyst typically used to effect polycondensation acts as both polymerizing and depolymerizing agent. Moreover, glycolic and lactic acids have a great tendency to cyclodimerize under these conditions and this renders simple polycondensation an unsuitable method.

The preferred method for producing high molecular weight polymers is ROP of the cyclic dimer, glycolide (and/or lactide). Depending on the catalyst involved, three different mechanisms have been reported: cationic, anionic and insertion. Among these, the insertion mechanism using metal alkoxides or carboxylates is the most desirable pathway and is the choice in commercial production (Frazza and Schmitt, 1971). Typical examples of catalysts of this class are aluminum, zinc, titanium, zirconium, antimony, tin(IV) and tin(II) alkoxides or carboxylates.

The insertion mechanism allows the preparation of high molecular weight polylactides without racemization up to temperatures above 150° C. (Kricheldorf and Kreiser-Saunders, 1996). The mechanism of ROP of lactones has been reviewed by Penczek and Slomkowski (1989). The tin catalyst, tin(II) octoate, was used extensively because of its acceptance by the FDA as a food stabilizer.

The polymerization of glycolide can be carried out in bulk at 220° C. for 4 h, at which time a 96% conversion and molecular weights from $10^4$ to $10^6$ have been reported. Copolymerization of glycolide with lactide has also been investigated. The reactivity ratios at 200° C. have been found to be 2.8 for glycolide and 0.2 for lactide. This indicates that copolymers of glycolic and lactic acids will have broad compositional ranges, with glycolide always being preferentially polymerized at low conversions and lactide being incorporated to ever-increasing extents as the glycolide is depleted (Gilding and Reed, 1979).

During the advanced stages of most ROPs, additional reactions such as ester-ester interchange and chain unzipping may take place. The extents of these reactions are affected by the reactivity of the ester moieties. These events can have a significant effect on the composition of the final product. Due to the ester exchange, cyclic dimer, trimer and, to a less extent, cyclic oligomers could be found along with the reformed monomer. In the case of copolymerization, additional randomization of the polymer chain would occur as a consequence of the ester-ester exchange of different ester moieties (Shalaby and Johnson, 1994). The microstructures of PLGA copolymers can be determined by both proton and carbon NMR spectroscopy (Ksaperczyk, 1996). It has been reported that the block lengths increase and, at the same time, the extent of transesterification decreases with decreasing polymerization temperature.

PGA was first developed as the synthetic absorbable suture, Dexon (Frazza and Schmitt, 1971). PGA has high crystallinilty, a high melting point and low solubility in organic solvents (Table 3). The polymer (fiber grade, inherent viscosity=1.2-1.6 dL/g in hexafluoro-isopropanol) can be spun into multifilament or monofilament yarns for the production of braided and monofilament sutures, respectively (Frazza and Schmitt, 1971; Chujo et al., 1967). A typical suture braid has a tensile strength of 80-100 Kpsi (Table 4). Owing to the hydrophilic nature of PGA, Dexon sutures tend to lose their mechanical strength rapidly (50%) over a period of 2 weeks and are absorbed in about 4 weeks after implantation (Frazza and Schmitt, 1971; Reed and Gilding, 1981; Katz and Turner, 1970).

TABLE 3

Crystallinity and Thermal Properties of PGA, PLA and Copolymers

| Polymer | % Crystallinity | Tm | Tg |
|---|---|---|---|
| PGA | 46-52 | 225 | 36 |
| 90:10 PGLA | 40 | 210 | 37 |
| 50:50 PGLA | 0 | None | 55 |
| PLA | 37 | 185 | 57 |
| dl-PLA | 0 | None | N/A |

Adapted from Wong and Mooney, 1997.

TABLE 4

Mechanical Properties of PGA and 90:10 PGLA

|  | PGA (Dexon) | 90:10 PGLA (Vicryl) |
|---|---|---|
| Tensile strength (Kpsi) | 106 | 95 |
| Knot strength (Kpsi) | 65 | 63 |
| Elongation (%) | 24 | 25 |

Adapted from Wong and Mooney, 1997.

The presence of an extra methyl group poly(L-lactic acid) (PLA) or poly(D-lactic acid) (d-PLA) makes them more hydrophobic than PGA. For instance, films of PLA only take up approximately 2% water (Gilding and Reed, 1979). In addition, the ester bond in PLA is less labile to hydrolysis due to steric hindrance of the methyl group. Therefore, PLA degrades much slower than PGA (Reed and Gilding, 1981) and has higher solubility in organic solvents.

PLA is employed much more often than d-PLA, since the hydrolysis of PLA yields L-lactic acid which is the naturally occurring stereoisomer of lactic acid. Whereas PLA possesses about 37% crystallinity, the optically inactive poly (DL-lactic acid) (dl-PLA) is amorphous. The difference in the crystallinity of dl-PLA and PLA has important practical outgrowths. For instance, the amorphous dl-PLA is usually considered in drug delivery application where a homogeneous dispersion of the active species within a monophasic matrix is desired (Engelberg and Kohn, 1991). However, the semicrystalline PLA is preferred in cases where high mechanical strength and toughness are required, for example, in orthopedic devices (Leenslag et al., 1987; Vainionpaa et al., 1987; Hay et al., 1988). It is pertinent to note that γ-irradiation of PLA causes chain scission, crosslinking and a decrease in crystallinity (Gupta and Deshmuth, 1983). Therefore, caution should be taken when sterilizing the polymer matrices by γ-irradiation.

To widen the range of materials properties exhibited by PGA, copolymers of GA and LA (PLGA) have been studied. Whereas PGA is highly crystalline, PLGA usually exhibit lower crystallinity and Tm (Gilding and Reed, 1979). For example, while PGA and PLA are partially crystalline, 50:50 PLGA is entirely amorphous. These morphological changes result in an increase in the rates of hydration and hydrolysis. Thus, copolymers tend to degrade more rapidly than PGA and PLA (Mooney et al., 1995b).

The degradation mechanism of PGA and copolymers in vitro is usually regarded as bulk erosion (Gombotz and Pettit, 1995). This is evident from the fact that a significant molecular weight decrease usually precedes monomer release from the polymer samples. This mechanism of degradation may be undesirable in certain applications. The relatively rapid release of large quantities of acid (glycolic and/or lactic acids) may lead to a local acidosis if a large mass of these polymers is present in a concentrated form (e.g., a solid pin). However, highly porous scaffolds are utilized in the present invention are highly porous and therefore contain a relatively low mass of polymer per unit volume. The highly porous structure of the scaffolds assists cell penetration as well as polymer degradation (Mooney et al., 1994b; 1995a; 1995b). The rate of degradation will be affected by the morphology of the scaffold and the large surface areas speed up the diffusion of water molecules into the bulk of the polymers when they are placed in an aqueous environment (e.g., in vivo).

The polymers undergo random chain scission by simple hydrolysis of the ester bond linkage and the monomer diffuses out of the polymer bulk into water (Reed and Gilding, 1981). It is important to note that loss of mechanical strength of PGA is faster when the polymer is incubated at a temperature higher than its Tg. This indicates that the glassy state protects PGA from hydrolysis since all short term chain motions are frozen. Water diffusion, and therefore hydrolysis, is more facile at temperatures above Tg. It is also relevant to mention that the Tg's of PGA and some copolymers are very close to the physiological temperature. Polymeric materials may undergo significant structural change after implantation due to water penetration and loss of mechanical strength. It is also speculated that enzymatic action may partially contribute to biodegradation of PGA in vivo.

The chemical compositions and the ratio of monomers used in the polymerization reaction strongly influence the degradation characteristics of the copolymer. The degradation rates for copolymers of GA and LA have been shown to be influenced by factors that affect polymer chain packing, i.e., crystallinity, and hydrophobicity. Since degradation is induced by hydrolysis, a crystalline structure or hydrophobic polymer composition disfavors dissolution and degradation.

Gombotz and Pettit (1995) summarized the specific factors affecting copolymer crystallinity and hydrophobicity: (i) the ratio of lactide to glycolide monomer in the copolymer, (ii) the stereoregularity of the monomer units in the polymer affects polymer chain packing, (iii) randomness of lactide and glycolide decrease the ability of chains to crystallize, and (iv) low molecular weight polymers degrade faster than high molecular weight polymers, especially when the end groups are free acid rather than capped with ester or other groups. Mass loss from polymer samples comprised of PLA is insignificant in the experimental time period (about 50 weeks). However, those comprised of copolymers of GA and LA or dl-PLA degrade much faster (the higher the glycolic acid content, the higher the degradation rate) (Mooney et al., 1995b).

The presence of monomers and low molecular weight cyclic oligomers in absorbable polymers should be avoided, for they degrade much more rapidly than the polymers and can lead to undesirable chemical and biological effects. (Shalaby and Johnson, 1994) It has been shown that polylactide with increased monomer content exhibits a higher rate of bioabsorption and a more drastic decrease of molecular weight. (Nakamura et al., 1989).

Those of skill in the art will understand that the PLA, PGA and PLGA polymers are just one example of biodegradable polymer tissue scaffolds that may be used in this invention. Further biodegradable tissue scaffolds include polyanhydrides, polyorthoesters, and poly(amino acids) (Peppas and Langer, 1994). Any such polymer materials may be utilized to fabricate a biodegradable polymer tissue scaffold with controlled properties for use in this invention. Further biodegradable polymers that produce non-toxic degradation products are listed in Table 5.

TABLE 5

Example Polymers Recognized as Biodegradable

Synthetic

Polypeptides
Polydepsipeptides
Nylon-2/nylon-6 copolyamides
Aliphatic polyesters Poly(glycolic acid) (PGA) and copolymers
Poly(lactic acid) (PLA) and copolymer
Poly(alkylene succinates)
Poly(hydroxy butyrate) (PHB)
Poly(butylene diglycolate)
Poly(.epsilon.-caprolactone) and copolymers
Polydihydropyrans
Polyphosphazenes
Poly(ortho ester)
Poly(cyano acrylates)

Natural

Modified polysaccharides
cellulose, starch, chitin
Modified proteins
collagen, fibrin Adapted from Wong and Mooney, 1997.

Little modification of these polymers is possible because there are no other functional groups on the side chain, except the methyl of the lactic acid residue. One possibility to modify the properties of these polymers is to form copolymers with residues having more diverse side chain structures, e.g., lysine.

A new monomer, 3-(Ne-benzoxycarbonyl-L-lysyl)-6-L-methyl-2,5-morpholinedione, was bulk copolymerized with L,L-lactide in the presence of stannous octoate as catalyst using the same ROP techniques utilized for lactide and glycolide (Barrera et al., 1993). The lysine content was determined by NMR technique to be approximately 1.3 mole %.

A poly(lactide-co-lysine) functionalized with peptide containing the arginine-glycine-aspartate (RGD) sequence was prepared by removal of the benzyoxycarbonyl protecting group on the lysyl residue and peptide coupling. The peptide concentration was found to be approximately 3.1 mmol/g which could be translated into a peptide surface density of 310 fmol/cm$^2$. A surface density of as low as 1 fmol/cm$^2$ of an RGD peptide has been previously determined to promote cell adhesion to an otherwise nonadherent surface (Massia and Hubbell, 1991). Therefore, by carefully processing the copolymer, biodegradable films with cell adhering properties can be prepared from the copolymer of lactide and lysine.

Other strategies have also been employed to widen the properties of polylactides. For example, PLA has also been synthesized as an acrylic macromonomer and subsequently copolymerized with polar acrylic monomers (e.g., 2-hydroxyethylmethacrylate) (Barakat et al., 1996). These polymers were studied as amphiphilic graft copolymers for drug delivery purposes. The surface properties of these polymers may be controlled by the ratio of the PLA graft length and copolymer content, and can be potentially used to control the drug release profile and biodistribution. Other examples of this approach include grafting PLA blocks to geraniol and pregnenolone (Kricheldorf and Kreiser-Saunders, 1996).

Other Polyesters

Properties of polyesters can also be varied by changing the structures of the polymer backbones. Polycaprolactone (PCL), having two more carbon atoms than PGA on the polymer backbone, has been studied as a substrate for biodegradation and as a matrix for drug release systems (Huang, 1989). Its degradation in vivo is much slower than PGA, therefore, it is suitable for controlled release devices with long in vivo life times (1-2 years). PCL can be prepared by anionic ring opening polymerization of E-caprolactone using metal hydroxide initiators (Jerome and Teyssie, 1989).

Poly-β-hydroxy acid can be prepared by both cationic and anionic ring opening polymerizations (Penczek and Slomkowski, 1989; Jerome and Teyssie, 1989). For example, 100% syndiotactic poly(β-DL-hydroxybutyrate) has been prepared by treating the corresponding lactone with cyclic dibutyltin initiators to yield high molecular weight polymers (Kricheldorf and Lee, 1995). Bacteria also produce the chiral, isotactic poly(β-D-hydroxybutyrate) as a highly crystalline biopolymer (Holmes, 1988).

Numerous analogs of poly(β-hydroxy acid) have been synthesized either chemically by the ring opening polymerization or biologically by feeding unusual carbon sources to bacteria (Timmins and Lenz, 1994). The microbial synthesis of polyesters has been reviewed by Gross (1994). Due to their biocompatibility and biodegradability, different blends of polycaprolactone, poly β-hydroxybutyrate) and other polymers have been fabricated for medical devices (Yasin and Tighe 1992), drug delivery applications (Wang, 1989) and cell microencapsulation (Giunchedi et al., 1994; Embleton and Tighe, 1993).

Surface-eroding polymer matrices are attractive for a variety of tissue engineering applications. The monomer release would be steady over the lifetime of the matrices in contrast to PLA and PGA. In addition, the gradual loss of polymer from the surface of the scaffold may allow the surrounding tissue to serially fill the space vacated by the polymer.

Polyorthoesters are an example of surface-eroding polymers. The hydrophobic character of the polymer limits water penetration and hydrolysis to only the exterior surface of the polymer matrix (Heller, 1985). Thus the surface erosion is much faster than that of the bulk. The chemical and physical properties of polyorthoesters have been reviewed (Heller and Daniels, 1994) and depend on the chemical structures of the constituent monomers. For example, reaction of bis (ketene acetal) with rigid trans-cyclohexane dimethanol produce a rigid polymer with a Tg of 110° C., whereas that of the flexible diol 1,6-hexanediol produces a soft material having a Tg of 20° C. Mixture of the two diol results in polymers having intermediate Tg.

Degradation of the polymers is acid-induced, and degradation rates can be increased by adding acidic excipients or by increasing the hydrophilicity of the polymer matrix. Conversely, degradation can be retarded by using basic excipients such as Mg(OH)$_2$ (Gombotz and Pettit, 1995). Current applications of these polymers include sustained drug delivery as well as hard and soft tissue fixation (Heller and Daniels, 1994).

Polyorthoformate, polycarbonate, poly(oxyethylene glycolate), poly(1,4-butylene diglycolate) and polyurethane are other biodegradable polymers that may have applications in tissue engineering. Many of these polymers have been previously been utilized as drug delivery matrices (Huang, 1989).

There are therefore a large number of polyesters and analogs that are biodegradable. Their mechanical properties can be controlled largely by the chemical structures of the constituent building blocks and can be varied from tough to elastic. The biocompatibility of these polymers is presumed to result from non-toxic degradation products. Bioactive elements can be attached to this class of materials in order to mimic natural extracellular matrix molecules.

Polypeptides

Proteins, one of the most important biomolecules in nature, belong to this class of biopolymers. However, polypeptides of a single amino acid or copolymers of were generally regarded as impractical industrial materials (Nathan and Kohn, 1994). Amino acid N-carboxyanhydrides were prepared as the monomeric starting materials, and this added considerably to the cost of all polypeptides. These polymers were thus expensive even if they were derived from cheap amino acids. In addition, it was almost impossible to control the sequence of the protein polymers using random copolymerization techniques. Most polypeptides are insoluble in common organic solvents. The need for exotic solvent systems to process these materials combined with their thermal instability made them poor engineering materials.

A number of recent approaches may, however, bypass these difficulties. Advances in genetic engineering have enabled investigators to obtain protein polymers by inserting DNA templates of predetermined sequences into the genome of bacteria. Collagen-like, silk-like, and silk-elastin-like proteins have been synthesized by this technique (Goldberg et al., 1989; Cappello et al., 1990; McGrath et al., 1992).

The general concept (O'Brien, 1993) involves the incorporation of amino acid sequences with desired properties, e.g., cell adhesion or elasticity, into the protein polymers to produce materials of predetermined structure and controlled properties. For example, a cell adhering sequence of RGD has been incorporated into silk-like protein polymers in a manner such that the tripeptide sequence is exposed for cell attachment (Tirrell et al., 1994).

Investigators have also developed chemical synthetic techniques that are complementary to the genetic approach to prepare such materials. For instance, different rigid non-peptide, organic segments have been combined with leucine-glutamine-proline, a sequence of the calcium binding domain of bovine amelogenins, using a completely synthetic approach (Sogah et al., 1994). The advantage of this class of protein-based hybrid polymers is the virtually unlimited choice of building blocks for the polymers. In contrast, genetically engineered proteins can only make use of the 20 natural and a limited number of unnatural amino acids for the construction of polymers.

Rigid organic segments have been used to reduce the conformational flexibility of the peptide chain through the formation of peptide secondary structures (e.g., β-sheet or α-turns). Controlled folding of the polymer backbone has been reported using such ordered building blocks (Wong, 1996). The potential application of these materials to tissue engineering is significant. These synthetic techniques allow precise control of material properties, while maintaining the freedom and flexibility to design protein-like materials with desirable biological and chemical properties. These properties may make this class of materials desirable matrices for tissue engineering applications.

Urry and coworkers have also studied elastin protein-based polymers as biocompatible materials. These polymers, also known as bioelastic materials, are elastomeric polypeptides comprised of the general repeating sequences glycine-any amino acid-glycine-valine-proline (GXGVP). The polymers were synthesized by the self condensation of the activated p-nitrophenol ester of the pentapeptide building blocks (Prasad et al., 1985). The molecular weight of these polymers are considered to be higher than 50,000. The polymers can be cross-linked by γ-irradiation to form an insoluble matrix without detectable residue destruction. Cell adhesion sequences (e.g., RGD) and enzymatic sites have been incorporated into the polymers for cell attachment and catalytic activity studies, respectively. Synthesis utilizing genetic engineering approach has also been reported. These class of polymers have been reported to exhibit excellent biocompatibility (Urry et al., 1995; Urry, 1993).

One specific polypeptide $(GVGVP)_n$ has been shown to undergo an inverse temperature transition in water (Urry, 1988a; Urry, 1988b). The mechanism of such elasticity has been demonstrated to be entropic in nature and is apparently due to the internal chain dynamics of the ordered polypeptide structure. This is contrary to the common belief that the elasticity of elastin, similar to synthetic polymers, is due to random chain network and random end-to-end distances (Alberts et al., 1983). The transition temperature can be controlled by the amino acid composition, pH and phosphorylation, electrochemical, photochemical and chemical reactions of prosthetic groups. Therefore, a device that converts chemical energy into mechanical work can be constructed.

Non-Biodegradable Tissue Scaffolds

Although biodegradable tissue scaffolds will have advantages in certain embodiments, they are by no means required for use in practicing the present invention. Non biodegradable tissue scaffolds are suitable if they are biocompatible and can promote deposition of ECM molecules and be mineralized in vivo.

Calcium phosphate ceramics are non-biodegradable tissue scaffolds that are extensively used in engineering bone tissue (Ducheyne, 1988) and may be used in the present invention. A suitable ceramic that may be used is described, for example, in U.S. Pat. No. 4,596,574.

Both hydroxyapatite and tricalcium phosphate, and mixtures of the two, may be utilized. These materials only release calcium and phosphate as breakdown products. They display no local or systemic toxicity, and become directly bonded to adjacent bone tissue with no intervening fibrous capsule (Ducheyne, 1988). The erosion and mechanical properties of these materials are controlled by the specific chemical composition and processing conditions (Lemons, 1988).

Applications of hydroxyapatite, tricalcium phosphate, and mixtures thereof are currently limited by their brittle nature and generally poor mechanical properties (Jarcho, 1981). However, this is not a drawback in the context of the present invention. In various aspects, calcium phosphate and other minerals such as fluoride, are intentionally associated with the tissue scaffolds Such pre-mineralization promotes proper regeneration and remineralization of dentin.

Other non-biodegradable polymers include semipermeable polymers such as poly(acrylonitrile-co-vinyl chloride) (Emerich et al., 1992; Sagan et al., 1993; Guenard et al., 1992), polylysine (Lim and Sun, 1980; O'Shea et al., 1984; Ricordi et al., 1988; Sullivan et al., 1991; Lacy et al., 1991; Levesque et al., 1992; Soon-Shiong et al., 1994), cellulose acetate (Yang et al., 1994) and polysulfone (Yang et al., 1994). Although generally intended for use in immobilized cells, the use of such polymers in the context of the present invention is certainly not excluded. These polymers may also be used with a variety of gels, including alginate and polyphosphazenes.

Hydrogels

As noted in foregoing definitions above, a hydrogel and a tissue scaffold have interchangeable meanings if the hydrogel is formed with sufficient porosity and pore size to allow three dimensional cell growth within the matrix of the hydrogel. Accordingly, the hydrogels described herein are also suitable for making tissue scaffolds when the hydrogels are formed with sufficient porosity and pore size to permit growth of tissue within the hydrogel matrix. However, some hydrogels have less porosity than required of a tissue scaffold and are used as a sealing barrier to cover implanted tissue scaffolds in certain aspects of the invention.

Blends, Interpenetrating Networks (IPN) and Composites

The use of polymer blends or composites (polymeric composite materials) as biomaterials is a concept that nature exploits in assembling the ECM in tissue. The ECM of tissues typically contains a composite of different macromolecules and non-macromolecular materials. For example, glycoaminoglycans, which are usually covalently linked to proteins to form proteoglycans, constitutes a gel-like, highly hydrated structure substance in the which the collagen fibers are embedded (Wight et al., 1991; Giusti et al., 1993).

Blends of fibrin and polyurethane have previously been formed by a combined phase-inversion and spray process to produce highly porous small-diameter vascular prostheses. (Giusti et al., 1985, Soldani et al., 1992). These materials exhibit high thermal stability, and their tensile behavior ranged from that of an elastic polyurethane tube to that of a natural blood vessel. Hydrogels of fibrin and poly(vinyl alcohol), blends or IPNs of collagen and poly(vinyl alcohol), blends of hyaluronic acid with poly(vinyl alcohol) or poly(acrylic acid), and blends based on esters of hyaluronic acid have been reported (Giusti et al., 1993). These materials may be suitable for a variety of applications including soft tissue replacement, drug delivery, nerve-guide growth and cardiovascular devices. This class of materials has great potential owing to the large number of readily available synthetic polymers that can be mixed with biopolymers.

Polysaccharides

Polysaccharides are carbohydrates characterized by the presence of a repeating structure in which the interunit linkages are of the O-glycoside type. The hydrophilicity of polysaccharides, along with the ease in which they can be formed into hydrogels, makes these materials ideal for many tissue engineering applications in which one desires to immobilize cells within a matrix. The variety of saccharides monomers (about 200) and the variety of possible O-glycoside linkages result in a diversity of polysaccharide structures and conformations. Polysaccharides may be derived from different sources including plants (starch, cellulose), animal (glycogen), algae and seaweeds (alginate and agarose) and microorganisms. These materials are usually considered as naturally-derived products. However, since polysaccharides are widely utilized as immobilization materials, they are used here as standards to which other synthetic materials are compared.

a. Algal Polysaccharides: Alginate and Agarose

Algal polysaccharides have been the most commonly utilized hydrogel materials. This is due to their gentle gelling conditions, widespread availability, and relative biocompatibility. The main starting sources of alginate are species of brown algae (Phaeophyceae). The algae are typically subjected to a number of processing steps to produce pure alginate which is the major polysaccharide present and may comprise up to 40% of the dry weight. It is part of the intracellular matrix and exists, in the native state, as a mixed salt of the various cations found in sea water (e.g., $Mg^{2+}$, $Ca^{2+}$, $Sr^{2+}$, $Ba^{2+}$ and $Na^+$). Due to selectivity of cation binding, the native alginate is mainly found in the insoluble gel form, which results from cross-linking of alginate chains by $Ca^{2+}$.

All alginates are copolymers of D-mannuronate (M) and L-guluronate (G). However, alginates from different algal sources have different compositions, and thus, different physical and mechanical properties. The block length of monomer units, and overall composition of the alginate and molecular weight, determine the properties of alginates. For example, calcium alginates rich in G are stiff materials (Sutherland, 1991).

Alginate selectively binds divalent metal ions such as $Ba^{2+}$, $Sr^{2+}$ and $Ca^{2+}$. The binding selectivity increases with G content, and polymannuronate is essentially non-selective. The calcium ions are, therefore, selectively bound between sequences of polyguluronate residue, and are held between diaxially linked L-guluronate residues which are in the $^1C_4$ chair conformation. The calcium ions are thus packed into the interstices between polyguluronate chains associated pairwise and this structure is named the "egg-box" sequence. The ability to form a junction zone depends on the length of the G-blocks in different alginates. Since the mechanical strength of alginate gels depend on the block lengths and M/G content, there have been efforts to modify the M/G ratio by alginase to increase the G content (Skjak-Braek et al., 1986). It is expected that chemically modified alginate would also produce materials of desirable properties. For example, bacterial alginates that contains acetyl groups generally exhibit different physical and mechanical properties from those of algal sources (Ott and Day, 1995).

Alginate can be gelled under mild conditions, allowing cell immobilization with little damage. Binding of $Mg^{2+}$ and monovalent ions to alginate does not induce gelation of alginate in aqueous solution (Sutherland, 1991). However, exposure of alginate to soluble calcium leads to a preferential binding of calcium and subsequent gelling. These gentle gelling conditions are in contrast to the large temperature or solvent changes typically required to induce similar phase changes in most materials.

Alginates have been utilized as immobilization matrices for cell (Smidsrod and Skjak-Braek, 1990), as an injectable matrix for engineering cartilaginous tissue to treat vesicoureteral reflux in various animal models (Atala et al., 1993 and Atala et al., 1994), and as injectable microcapsules containing islet cells to treat animal models of diabetes (Sun et al., 1984).

The open lattice structure and wide distribution of pore sizes in calcium alginate preclude the controlled release of large molecules (e.g., proteins) from these materials and limits the use of pure alginate for entrapment of whole cells or cell organelles (Smidsrod and Skjak-Braek, 1990). However, alginate membrane can be modified by incorporating other polymeric elements (e.g., lysine, poly(ethylene glycol), poly(vinyl alcohol) or chitosan) (Polk et al., 1994, Kung et al., 1995). These modified systems have been used to control the release of proteins from alginate beads. Haemostatic swabs made of calcium alginate have also been clinically utilized to reduce blood loss during surgical procedures. The calcium ions in alginate may assist the blood clotting process by activating platelets and clotting factor VII (Blair et al., 1990).

Agarose is another type of marine algal polysaccharide. In contrast to alginate, agarose forms thermally reversible gels. Agarose will set at concentrations in excess of 0.1%, depending on the sulfate content, and at temperatures considerably below (about 40° C.) the gel-melting temperature (about 90° C.). The latter parameter is correlated to the methoxy content. The proposed gel structure is bundles of associated double helices and the junction zones consist of multiple chain aggregations (Yalpani, 1988). Agarose has been used largely in gels for electrophoresis of proteins and nucleic acids. However, agarose gels have also been used as supporting materials for electrophoresis of bacteriophages (Serwer, 1987) and migration studies of leukocytes (Kallen et al., 1977). Although applications in tissue engineering have not been reported, its adjustable gelling behaviour may render low temperature melting agarose a suitable injectable and immobilization matrix material.

b. Other Polysaccharides

Microbial polysaccharides are ubiquitous in nature and very abundant biopolymers. They are of interest because of their unusual and useful functional properties. Some of these properties are summarized by Kaplan et al. (1994) as: (i) film-forming and gel-forming capabilities, (ii) stability over broad temperature ranges, (iii) biocompatibility (natural products avoid the release/leaching of toxic metals, residual chemicals, catalyst, or additives), (iv) unusual rheological properties, (v) biodegradability, (vi) water solubility in the native state or reduced solubility if chemically modified, and (vii) thermal processability for some of these polymers. Some examples of microbial polysaccharides suitable for forming hydrogels for use in this invention are listed in Table 6. It is worthy to note that gellan, one of the microbial polysaccharides, has been investigated as immobilization materials for enzymes and cells (Doner and Douds, 1995).

TABLE 6

Some Polysaccharides Synthesized by Microorganisms

| Polymer | Structure |
|---|---|
| Fungal | |
| Pullulan (N) | 1,4-1,6-α-D-Glucan |
| Scleroglucan (N) | 1,3-1,6-αD-Glucan |
| Chitin (N) | 1,4-β-D-Acetyl glucosamine |
| Chitosan (C) | 1,4-β-D-N-Glucosamine |
| Elsinan (N) | 1,4-1,3-α-D-Glucan |
| Bacterial | |
| Xanthan gum (A) | 1,4-β-D-Glucan with D-mannose; D-glucuronic acid as side groups |
| Curdlan (N) | 1,3-β-D-Glucan (with branching) |
| Dextran (N) | 1,6-α-D-Glucan with some 1,2-1,3-1,4-α-linkages |
| Gellan (A) | 1,4-β-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan | a N = neutral,
A = anionic and
C = cationic.
Adapted from Wong and Mooney, 1997.

Non-Natural Hydrogels a. Polyphosphazenes

Polyphosphazenes contain inorganic backbones comprised of alternating single and double bonds between nitrogen and phosphorus atoms, in contrast to the carbon-carbon backbone in most other polymers. The uniqueness of polyphosphazenes stems from the combination of this inorganic backbone with versatile side chain functionalities that can be tailored for different applications. The degradation of polyphosphazenes results in the release of phosphate and ammonium ions along with the side groups (Allcock, 1989; Scopelianos, 1994).

Linear, uncross-linked polymers can be prepared by thermal ring opening polymerization of $(NPCl_2)_3$ and the chloro group replaced by amines, alkoxides or organometallic reagents to form hydrolytically stable, high molecular weight poly(organophosphazenes). Depending on the properties of the side groups, the polyphosphazenes can be hydrophobic, hydrophilic or amphiphilic. The polymers can be fabricated into films, membranes and hydrogels for biomedical applications by cross-linking or grafting (Lora et al., 1991; Allcock et al., 1988; Allcock, 1989). Bioerodible polymers for drug delivery devices have been prepared by incorporating hydrolytic side chains of imidazole (Laurencin et al., 1987) for skeletal tissue regeneration (Laurencin et al., 1993). Non-degradable phosphazenes have been used as denture liner (Razavi et al., 1993). Their use in the present invention is thus particularly contemplated.

b. Poly(Vinyl Alcohol) (PVA)

PVA is not synthesized directly but is the deacetylated product of poly(vinyl acetate). Polyvinyl acetate is usually prepared by radical polymerization of vinyl acetate (bulk, solution or emulsion polymerizations) (Finch, 1973). PVA is formed by either alcoholysis, hydrolysis or aminolysis processes of poly(vinyl acetate). The hydrophilicity and water solubility of PVA can be readily controlled by the extent of hydrolysis and molecular weight. PVA has been widely used as thickening and wetting agent.

PVA gels can be prepared by cross-linking with formaldehyde in the presence of sulfuric acid (Schwartz et al., 1960). These formaldehyde-cross-linked PVA materials have been used as prosthesis for a variety of plastic surgery applications including breast augmentation (Clarkson, 1960 and Peters and Smith, 1981), diaphragm replacement (Haupt and Myers, 1960) and bone replacement (Camerson and Lawson, 1960). However, a variety of complications were found after long term implantation, including calcification of the PVA (Peters and Smith, 1981). In the present invention, calcification is a desired feature because when a tissue scaffold is implanted in the tooth of a subject, regeneration of the dentin or enamel involves remineralization of tissue scaffold with calcium phosphate.

More recently, PVA was made into an insoluble gel using a physical cross-linking process. These gels were prepared with a repeated freezing-thawing process. This causes structural densification of the hydrogel due to the formation of semicrystalline structures. The use of this gel in drug delivery applications has been reported (Peppas and Scott, 1992; Ficek and Peppas, 1993). However, PVA is not truly biodegradable due to the lack of labile bonds within the polymer bond. Only low molecular weight materials are advisable to be used as implant materials.

c. Poly(Ethylene Oxide) (PEO)

PEO or polyethylene glycol can be produced by the anionic or cationic polymerization of ethylene oxide using a variety of initiators (Boileau, 1989; Penczek and Kubisa, 1989). PEO is highly hydrophilic and biocompatible, and has been utilized in a variety of biomedical applications including preparation of biologically relevant conjugates (Zalipsky, 1995), induction of cell membrane fusion (Lentz, 1994) and surface modification of biomaterials (Amiji and Park, 1993). Different polymer architectures have been synthesized and some of their applications in medicine have been recently reviewed (Merrill, 1993). For example, PEO can be made into hydrogels by γ-ray or electron beam irradiation and chemical crosslinking (Cima et al., 1995; Belcheva et al., 1996). These hydrogels have been used as matrices for drug delivery and cell adhesion studies.

d. Pluronics

Pluronic polyols or polyoxamers are block copolymers of PEO and poly(propylene oxide and are usually synthesized by anionic polymerization in the form of a ABA triblock using a difunctional initiator (Schmolka, 1972). Pluronics F 127, which contains 70% ethylene oxide and 30% propylene oxide by weight with an average molecular weight of 11,500, is the most commonly used gel-forming polymer matrix to deliver proteins (Gombotz and Pettit, 1995).

This polymer exhibits a reversible thermal gelation in aqueous solutions at a concentration of 20% or more (Schmolka, 1972). Thus, the polymer solution is a liquid at room temperature but gels rapidly in the body. Although the polymer is not degraded by the body, the gels dissolve slowly and the polymer is eventually cleared. This polymer has been utilized in protein delivery (Morikawa et al., 1987; Jushasz et al., 1989) and skin burn treatments (Pautian et al., 1993).

e. PGA-PEO Hydrogels

Although PGA is not water soluble, bioerodible hydrogels based on photopolymerized PGA-PEO copolymers have been synthesized and their biological activities investigated. (Sawhney et al., 1993; Sawhney et al., 1994; Hill-West et al., 1994). Macromonomers having a poly(ethylene glycol) central block, extended with oligomers of α-hydroxy acids (e.g., oligo(dl-lactic acid) or oligo(glycolic acid)) and terminated with acrylate groups were synthesized. These hydrogels were designed to form direct contacts with tissues or proteins following photopolymerization, and act as a barrier.

These gels degrade upon hydrolysis of the oligo(α-hydroxy acid) regions into poly(ethylene glycol), the α-hydroxy acid, and oligo(acrylic acid). The degradation rate of these gels could be tailored from less than 1 day to 4 months by appropriate choice of the oligo(α-hydroxy acid). The macromonomer could be polymerized using non-toxic photoinitiators with visible light without excess heating or local toxicity. The hydrogels polymerized in contact with tissue adhere tightly to the underlying tissue. In contrast, the gels were nonadhesive if they were polymerized prior to contact with tissue. These hydrogels have been utilized in animal models to prevent post-surgical adhesion and thrombosis of blood vessels and initimal thickening following balloon catheterization.

Exogenous Factors Added to Tissue Scaffolds or Hydrogels

One aspect of the invention incorporates bioactive exogenous factors into the tissue scaffolds or hydrogels to stimulate tissue growth, relieve pain, fight infection, reduce inflammation or otherwise facilitate the process of tooth repair in the methods of the invention.

a. ECM Components

In certain practices of the invention, growth factors that affect the proliferation of cells and tissues may be used in conjunction with the tissue scaffolds or hydrogels. It is preferable that the tissue-specific function of the proliferating cells that infiltrate the tissue scaffold be maintained. The function of the proliferating cells is strongly dependent on the presence of specific growth factors and ECM molecules (Stoker et al., 1990). For example, in vitro, it is know that cells can be switched from a phase of tissue-specific gene expression to one of proliferation simply by altering the ECM presentation to the cell (Mooney et al., 1992). Accordingly ECM proteins, hyaluronic acid or other components of the ECM may be incorporated into the tissue scaffolds used in the invention. If desired, any one of a variety of tissue scaffolds that incorporate specific ECM molecules may be used to supplement the correct signalling to the host's proliferating cells (Green et al., 1979; Yannas et al., 1981; Bell et al., 1981; Stern et al., 1990; Compton et al., 1989; Dixit, 1994; Kasai et al., 1994; Cavallaro et al., 1994; Anselme, 1992; Koide et al., 1993; Guenard et al., 1992).

Synthetic materials that incorporate specific peptides to enhance cell adhesion (McGrath et al., 1992; Barrera et al., 1993; Hubbell, 1993) may be used, including those that incorporate a variety of different peptides in order to mimic the multi-functional nature of ECM molecules (Hynes, 1990). Growth factors promoting tissue development may be lacking or deficient in the host tissue site that the engineered tissue is applied to.

b. Growth Factors

The use of growth factors in the context of cell proliferation and culture is generally well known in the art, although growth factors, other than those naturally present in the serum at low levels, have not been used in conjunction with oral tissue regeneration on a structural matrix in vivo. However, in that growth factors are routinely used in other contexts, one of skill in the art will readily understand how to apply growth factors in the context of the present invention based on of instant disclosure.

In general terms, it will be understood that a growth factor that has already been established to have a beneficial physiological effect on a particular cell type should be chosen for use in regenerating tissue containing such cells. Certain growth factors may be used to stimulate the proliferation of a wide number of cell types, whereas other growth factors may have a more limited or defined cell-specificity.

Platelet-derived growth factor, (PDGF, e.g., PDGF-BB), which is one member of the TGF supergene family of growth factors, may be used either alone or in combination with dexamethasone; or other growth factors. Particular examples of suitable growth factors include other members of the TGF supergene family, such as, BMP-2, BMP 4, BMP-7, VEGF, FGF-1, FGF-2, IGF-1, IGF-2, GDF-1, GDF-2, GDF-2, GDF-3, GDF-4, GDF-5, or combinations of the same. PDGF-BB and dexamethasone are effective for the growth of pulp, periodontal ligament and gingival fibroblasts (Rutherford et al., 1992a, 1992b; 1993a), and are particularly proposed for use in connection with these aspects of the invention. U.S. Pat. No. 5,149,691, incorporated herein by reference, describes the use of combinations of PDGF and dexamethasone for the repair and regeneration of tissues in vivo. U.S. Pat. Nos. 5,376,636 and 5,149,691, each incorporated herein by reference, also describe the use of PDGF and glucocorticoids in tissue regeneration. Any such teachings may be used in connection with the present invention. It is also known that this combination and PDGF/ IGF-1 induce regeneration of the periodontium in an animal model of periodontitis (Rutherford et al., 1992b; 1993a).

Bone Morphogenic proteins (BMP) such as those described in U.S. Pat. Nos. 4,795,804; 4,877,864; 4,968, 590; 5,011,691; 5,013,649; 5,106,748; 5,108,753; 5,116, 738; 5,141,905; 5,166,058 and 5,187,076 are employed in certain aspects of the present invention. It has been demonstrated that a single application of BMP-7 to a freshly and partially amputated dental pulp induced reparative dentinogenesis in ferrets, monkeys and humans (Rutherford et al., 1993b, 1994, 1995). Additionally, it has been demonstrated that BMP-7 induced bone when implanted in gingiva, indicating that gingiva possess cells that are capable of forming mineralized tissue such as bone.

Direct local application of recombinant growth factors (e.g., BMP-2) has been shown to induce reparative dentinogenesis in dogs and primates when placed on partially amputated dental pulps (Rutherford et. al., 1993b; Nakashima, 1994; Rutherford et. al., 1994), or on a freshly cut dental surface ("transdentinal" application; Rutherford et. al., 1995). However, in many clinical situations no pulp remains to stimulate. Moreover, direct application of the growth factors was not effective when the pulp was inflamed. The present invention provides methods of treatment where some pulp remains, whether or not it is inflamed, based on recognizing that BMP-7 (alone or in combination with other growth factors, such as BMP-2, BMP-4, BMP-7 or GDF-5) can be delivered from the implanted tissue scaffold, or from a hydrogel in contact with the same, over time as the tissue scaffold or hydrogel is degraded in vivo. Thus, the problem of inflammation, which is commonly associated with most dental conditions where the pulp is exposed, is not a barrier to stimulating growth of cells from the remaining pulp in the present invention, because the tissue scaffold is placed in contact with the pulp for a sufficient time for the inflammation to recede and/or optionally, antiinflammatory agents are combined with the tissue scaffold to facilitate the process.

The growth factors or stimulatory agents that are useful in the context of the present invention may be purified from natural sources or may be recombinantly prepared proteins. They may be obtained from commercial sources, if desired. Those of skill in the art will know how to obtain and use such growth factors in the context of tissue regeneration in light of the present disclosure.

c Antiinflammatory Agents

As previously mentioned, in certain practices an anti-inflammatory agent is combined with the tissue scaffold or hydrogel inserted into the tooth of a subject. In one embodiment, the tissue scaffold or hydrogel may include the anti-inflammatory agent alone, while in other embodiments it may include the anti-inflammatory agent in combination with a morphogenic factor, antibiotic or other biologically active agent. Suitable anti-inflammatory agents include, amongst others, those in the class of Cox-I and Cox II inhibitors. Examples of such agents include acetyl-salicylic acid, acetaminophens, naproxen, ibuprofen and the like. Another example of a suitable class of anti-inflammatory agents includes soluble cytokine receptors such as Embrel™ or IL-1b binding receptors. The amount of anti-inflammatory agent used is adjusted so as to be released from the tissue scaffold or hydrogel over a period of about 2 days or more.

d Analgesic Agents or Anesthetics.

In some embodiments, the tissue scaffold or hydrogels used in the present invention may include analgesic agents or anesthetics. The anti-inflammatory agents mentioned above also serve as analgesic agents, thus analgesic agents include anti-inflammatories. In addition, the analgesic agent may include local pain deadening agents (anesthetics) such as lidocaine, that provide local pain relief for a period of about 30 minutes or more.

e Antibiotic Agents

In various embodiments, the tissue scaffold or hydrogels used in the invention may include an antibiotic agent. There are numerous classes of antibiotic agents suitable for the invention including, but not limited to: tetracyclines, chemically modified tetracyclines, cyclosporins, those in the penicillin family, amoxcillan, gentamicin, erythromycin, chloramphenicol, florfenicol, vancomycin, everninomicin, cefotaxime, streptomycin, ciprofloxacin, nalidixic acid, bacitracin, enrofloxacin, and flavomycin.

In various embodiments, the tissue scaffold or hydrogels of the invention may also include compositions for diffusing calcium phosphate ions to assist in remineralization and repair of caries lesions. Suitable examples of such compositions are described, for example, in U.S. Pat. Nos. 5,833,954 and 5,993,786.

Amalgams, Cements and Fillers

The invention also includes sealing the hole in the tooth of the subject with a dental cement, filler or amalgam after placement of the dental scaffold material and/or optional hydrogel. Suitable cements include for example, any cement formulated for use as a base or liner, such as zinc phosphate, glass ionomers or calcium phosphate. The cements may include a polymeribizable monomer, such as a carboxylated monomer. One particular cement preferred for the invention also contains a polymeribizable monomer and di-calcium/tetra-calcium oxide as described, for example, in U.S. Pat. No. 6,398,859 and U.S. Pat. Pub. No. 2002/0137812. The cement may also include flouride. One suitable example of a cement that contains flouride is described in U.S. Pat. No. 6,056,930. Conventional metal based amalgams, although suitable in some practices of the invention, should be avoided where possible.

Wafers

Figure 2:
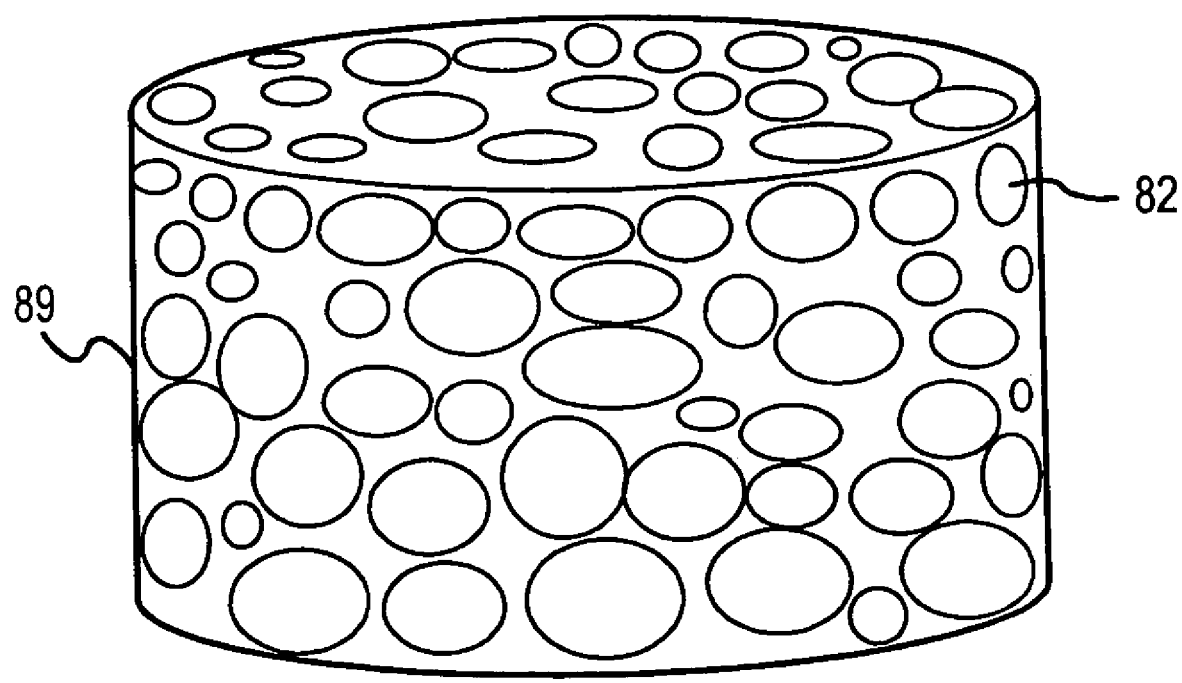
FIG. 2 illustrates an example of a tissue scaffold wafer suitable for use in one aspect of the invention.
Figure 3A:
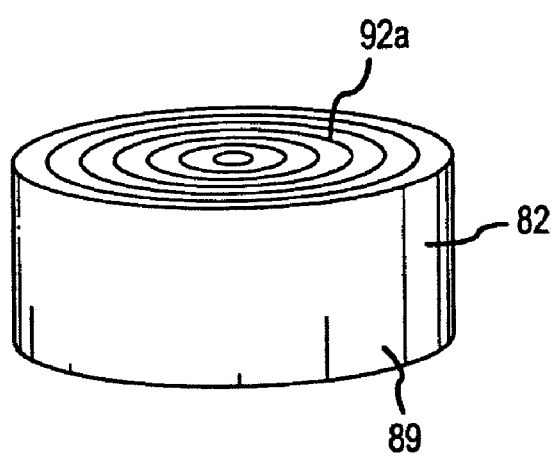
FIGS. 3A-3D illustrate various markings on the top surface of wafers according to another aspect of the invention.
Figure 3B:
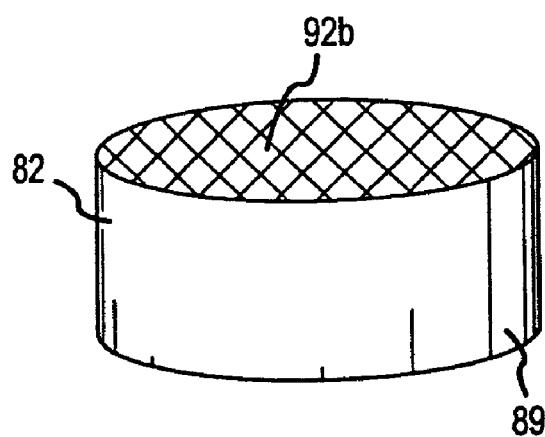
Figure 3C:
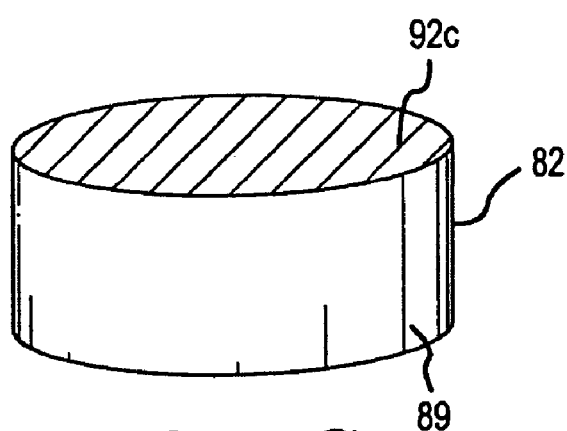
Figure 3D:
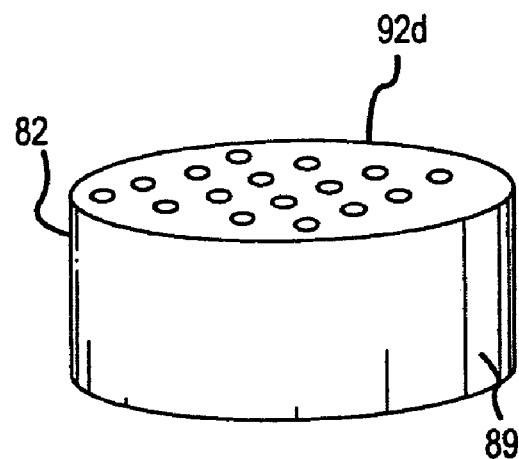

As mentioned in the definitions section, the tissue scaffolds used in the present invention are shaped into wafers of predetermined size to correspond to the size of a hole drilled into the tooth of a subject. The wafers may be fabricated by any number of techniques and have a variety types of pore structures. FIG. 2 illustrates an exemplary embodiment of a molded wafer 89, suitable for use in the invention. In the embodiment depicted in FIG. 2, the wafer 89 is formed into a sponge where the interior is filled with the tissue scaffold material 82 of suitable porosity and pore size to permit the tissue to grow into and through out the matrix of the scaffold material 82.

The wafer 89 depicted in FIG. 2 is for example purposes only. The tissue scaffold material 82 wafers can be made into other forms suitable for the purposes of the invention, including, but not limited to, open barrel structures with an open lumenal space, concentric barrel structures with concentric rings of the scaffold material 82 forming concentric lumenal spaces, spiral barrel structures with a spiral lumenal space, three dimensional interlinking sheets of the scaffold material 82, mats, spheres, cones and a variety of other geometric forms shaped to fit into a hole of corresponding size drilled into the tooth of a subject.

Another aspect of the invention is wafers having particular markings thereon to detect crushing. The highly porous tissue scaffolds used in the invention are typically fragile structures that are subject to accidental crushing when being manipulated or inserted into the hole of corresponding size drilled in the subject's tooth. As illustrated by the examples in FIGS. 3A-3D, to readily detect crushing, the upper surface (or lower surface) of the wafers 89 of the invention may be marked with a pharmaceutically acceptable dye arranged in a pattern that that alters appearance when the wafer is crushed. In typical embodiments, the pattern includes regularly spaced markings 92a-92d so that crushing is detected when an irregularity in appearance is exhibited. In the embodiment depicted in FIG. 3A, the markings 92a are in concentric circles. In the embodiment depicted in FIG. 3B the markings are regularly spaced hatch markings 92b. In the embodiment depicted in FIG. 3c the markings are parallel lines 92c. In the embodiment depicted in FIG. 3D the markings are regularly spaced dots or other geometric forms. The embodiments depicted in FIGS. 3A-3D are for example purposes only. Other markings or other means for detecting a crushed wafer can readily be envisioned based on the present disclosure.

Tissue Scaffold Wafer Supports

Another aspect of the invention related to the prevention of crushing is a tissue scaffold support casing for supporting the tissue scaffold wafers 89. Several embodiments of such support casings are depicted in FIGS. 4A-4D. The tissue scaffold wafers 89 made of the porous tissue scaffolding material 82 are supported by a casing comprised of support elements 95, 97, 98, 99 101 and/or 103 made of a higher strength polymer. The higher strength polymer may be biodegradable or non-bio degradable. In one embodiment, the higher strength polymer is comprised of PGA, PLA, PLLA, PLDLA, or PLGA having a porosity of less than 50% or less than 40% or less than 30% or less than 20%, or less than 10%. The higher strength polymer may also be non-porous (solid) in certain embodiments. Alternatively, the support material for the casing may be made of a dental cement, amalgam, a fiber reinforced resin or another polymeric material.

As illustrated in FIGS. 4A-4D, the casing support material is configured to partially surround a portion the tissue scaffolding wafer 89. Generally, the tissue scaffolding wafer 89 is made of a material that has a first crushing resistance and the casing support material is selected to have a second crushing resistance greater than the first crushing resistance. In the embodiment illustrated in FIG. 4A, the support casing material includes a horizontally disposed ring 97 configured to contact the top and bottom of the tissue scaffold wafer 89. In other embodiments, the ring 97 contacts one or the other of the top and bottom surfaces of the tissue scaffold wafer 89. In all of the embodiments depicted in FIGS. 4A to 4D, the casing material includes at least one columnar extension 95 extending from the an upper part of the casing material downwardly along the sides of the wafer 89 between the top bottom surfaces. However, other configurations of the support casing material that contact the sides of the wafers, including for example, spirals, crosses, meshes and the like, may also be used in lieu of the columnar extensions.

Figure 5:
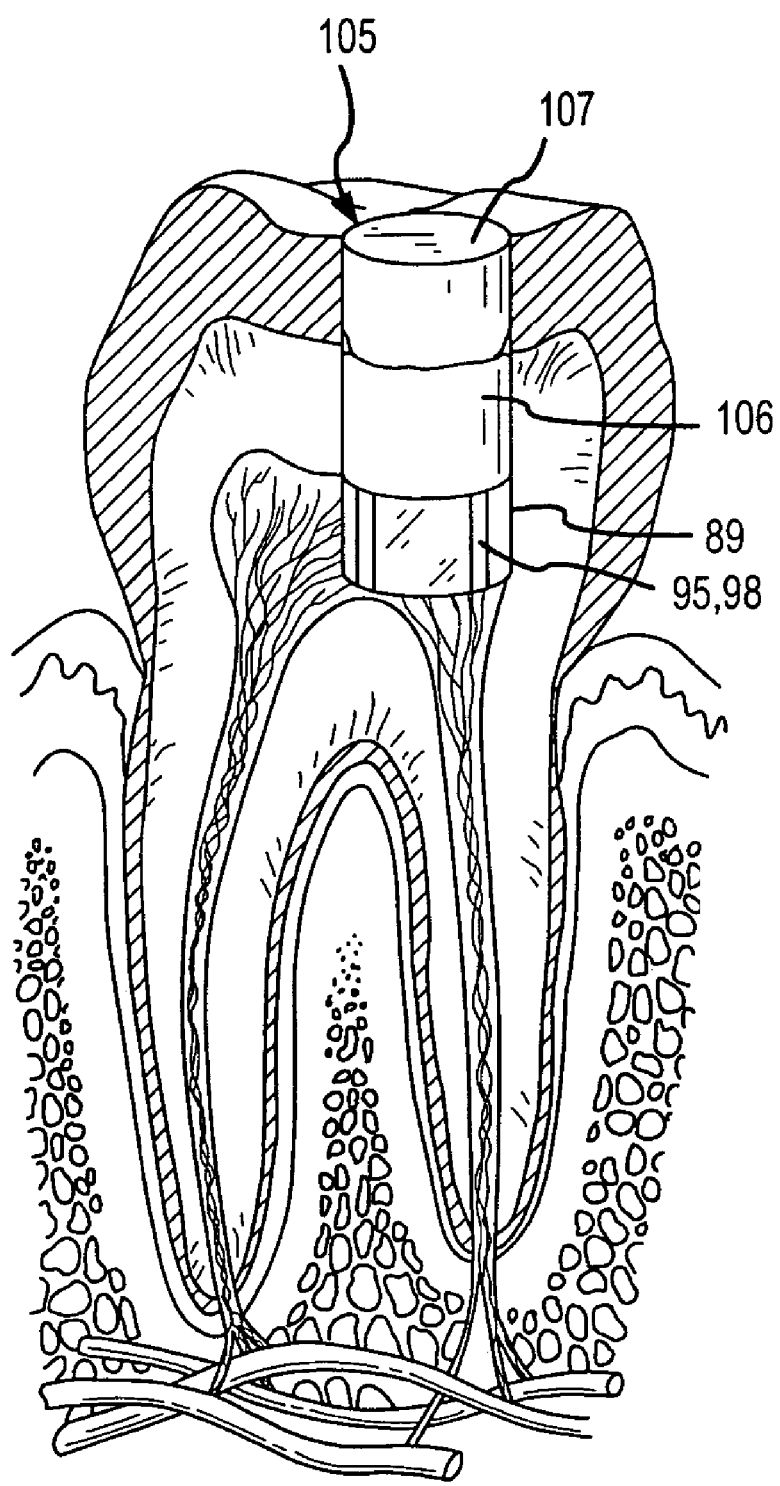
FIG. 5 illustrates a tissue scaffold wafer with casing supports and a hydrogel seal implanted in a tooth according to another aspect of the invention.

In the embodiment depicted in FIG. 4B, instead of using the support casing ring 95, a circular pad 99 of the casing material is used on the top surface. In this embodiments, the pad 99 provides an orientation for the wafer, typically with the pad being on the top surface that will face the crown. The bottom surface will face the pulp 70 when positioned in a hole in subject's tooth. In the embodiment depicted in FIG. 4C, the columnar extensions are configured as brackets that include a laterally extended portion 101 roughly perpendicular to the columnar extension 95 so that at least one of the top or bottom of the wafer is positioned beneath or above, respectively, the laterally extended portions 101. In the embodiment depicted in FIG. 4D, the laterally extended portion is formed as a brace 103 connecting at least two columnar extensions. The brace 103 extends across at least one of the top and bottom surfaces of the tissue scaffold wafer 89. Placement of the tissue scaffold wafer 89 with the casing support elements 95, 97, 98, 99, 101, 103 in the tooth of a subject is illustrated in FIG. 5. In a typical practice, the wafer 89 with support casing elements 95, 97, 98, 99, 101, 103 is first positioned into the hole of corresponding size 105 drilled in the tooth of a subject. The wafer 89 is secured into the hole with a base material 106, which may for example be a hydrogel. The top of the tooth is finally sealed with an appropriate amalgam, cement or other filling material 107.

Kits

Figure 6:
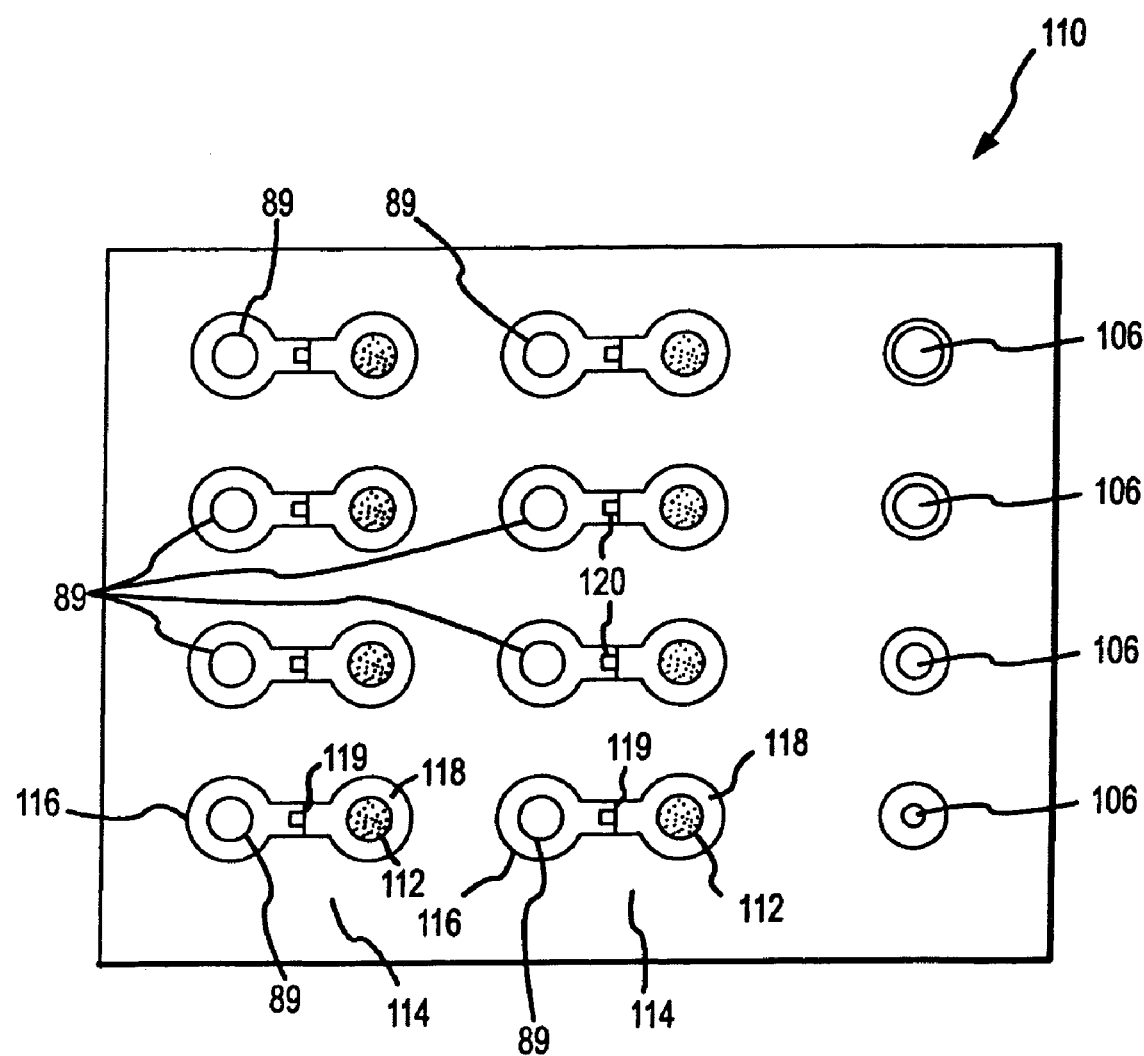
FIG. 6 illustrates a tissue scaffold wafer kit according to another aspect of the invention.

FIG. 6 illustrates another aspect of the invention, which is a kit 110 specifically designed to store a set of dry tissue scaffold wafers 89 of a predetermined size to correspond with dental drilling bits, in conjunction with set of wetting solutions 112 to hydrate the tissue scaffold material 82. The kit includes a blister pack 114 carrying a set of individual dry wafers 89 arranged in an array of heights from about 0.1 to about 0.8 mm, most typically about 0.5 mm in height, and in diameters of about 0.5 to about 5 mm, most typically about 2 to 5 mm in diameter. Each of the individual dry wafers 89 is positioned in a first chamber 116 of the blister pack 114 that is positioned adjacent to second chamber 118 holding the wetting solution 112. The two chambers are separated by a thin wall 119 that is broken upon snapping a blister snap 120 which causes the wetting solution 112 to flow into the first chamber 116 and hydrate the wafer. The dry wafers 89 may include lyophilized or otherwise dried exogenous factors, morphogenic agents, analgesic agents, antibodies and the like. Alternatively, such exogenous factors may be contained in hydrated form along with the wetting solution 112.

In one embodiment, the kit 110 may also include a plurality of pre-hydrated hydrogel plugs 106 of corresponding size arranged below the tissue scaffolds. The hydrogel plugs 106 may contain exogenous factors, morphogenic agents, analgesic agents, antibodies and the like already loaded into the hydrogel 106. Alternatively, the kit may include components for mixing the hydrogel 106 in batch for loading into a syringe or other suitable delivery device. The hydrogel components may be mixed alone or in combination with the exogenous factors. In certain embodiments the exogenous factors may be included in a separate chamber for mixing with the hydrogel components or the tissue scaffold wafers 89.

The kits of the present invention thus typically include a means for containing the necessary components for use in close confinement for commercial distribution. The kit may also include a variety of vials or other containers for holding the necessary components. Irrespective of the number or type of containers, the kits of the invention are typically packaged with instructions for use of the kit components.

Vacuum Manipulator

Figure 7:
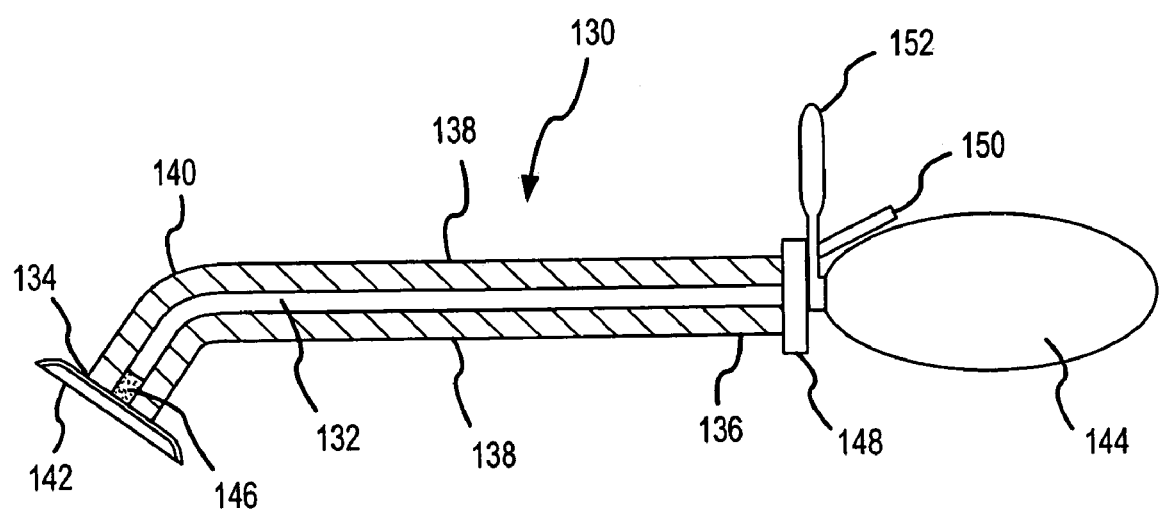
FIG. 7 illustrates a vacuum manipulator according to another aspect of the invention.

FIG. 7 illustrates another aspect of the invention, which is a vacuum manipulator 130 configured for manipulating and placing the fragile tissue scaffolding materials in the hole of corresponding size drilled into the tooth of a subject. The vaccuum manipulator 130 includes an elongated vacuum tube 132 having a proximal end 134, a distal end 136, and walls 138 between the proximal and distal ends defining the vacuum tube 132. In certain embodiments, the vacuum tube 132 may have a bend 140 along the length thereof to orient the proximal end 134 for insertion into a mouth of subject along a plane defined by adjacent tooth crowns. The vacuum manipulator 130 further includes a suction cup 142 attached to the proximal end 134. The suction cup 142 is configured to be in fluid communication with the vacuum tube 132 and a vacuum source 144. The suction cup 142 is sized to fit onto a surface of a wafer 89 comprised of tissue scaffolding material 82. In certain embodiments particularly useful for wafers protected with a support casing, the outer perimeter of the suction cup 142 is configured to fit around the ring 97 of support material so that the tissue scaffold material 82 is not contacted by the device.

The vacuum manipulator 130 may also include an in-line filter 146 disposed in the vacuum tube 132 between the suction cup 142 and the distal end 136. The in-line filter 146 has sufficient pore size to allow passage of the gas fluid between the suction cup and the vacuum chamber while preventing the passage of bacteria or other pathogens. The vacuum manipulator 130 further includes a vacuum valve assembly 148 located at the distal end 136 of the vacuum tube 132. The valve assembly 148 is operable to close and open fluid access between the vacuum tube 132 and the vacuum source 144 and, optionally, to open and close fluid access between the vacuum tube 132 and a positive pressure source 150. The positive pressure source 150 provides a source of pressure that is greater than the pressure of the vacuum drawn in the vacuum tube 132. The positive pressure source 150 may be coupled to the same vacuum source 144, so that when the vacuum source is operated in an opposite direction as used to draw the vacuum, a positive pressure flows into the vacuum tube. In alternative embodiments, the source of positive pressure 150 may be an opening to ambient air pressure, or a second bulb, plunger or diaphragm. In yet another embodiment the source positive pressure 150 may be an external compressor or in-house air source.

The valve assembly 148 is operated by manipulation of a control switch 152, which is mechanically or electro-mechanically coupled to the valve assembly 148. The control switch 152 optionally has dial settings for a closed position, a vacuum drawing position, and a vacuum release (or positive pressure) position. In certain embodiments, the valve assembly 148 or control switch 152 is adjustable to allow a controlled amount of at least one of positive or negative pressure to be drawn or applied within the vacuum tube 132.

In one embodiment, the vacuum source 144 may be a bulb, plunger or a compressible diaphragm. In another embodiment, the vacuum source 144 may be an external aspirator or vacuum pump separate from the vacuum manipulator 130. In such embodiments, the vaccuum manipulator 130 may include a connector assembly for connecting the vacuum tube to the external vacuum source. In certain embodiments, the vacuum manipulator 130 may optionally include a safety release configured with the valve assembly 148 to release any excessive vacuum drawn in the vacuum tube 132.

In use, the operator positions the suction cup 142 over the top end of the wafer and manipulates the control switch 152 to draw a vacuum in the vacuum tube 132 thereby grabbing the top end of the wafer. The bottom end of the wafer is then positioned in place in the hole made in the subject's tooth in contact with the pulp tissue 70. When properly positioned, the operator releases the vacuum by operation of the control switch 152 thereby dislodging the wafer from the suction cup 142. In embodiments configured with the positive pressure source 150, the control switch is manipulated to a release position that applies positive pressure into the vacuum tube 132 to assure the wafer is dislodged. The control switch 152, valve assembly 148, and positive pressure source 150 may be electromechanically configured to cooperatively operate to accomplish vacuum release and positive pressure simultaneously or sequentially upon release of the vacuum.

Methods for Treating Dental Conditions

A. Treating Asymptomatic ("Nonsymptomatic") Caries

Figure 8:
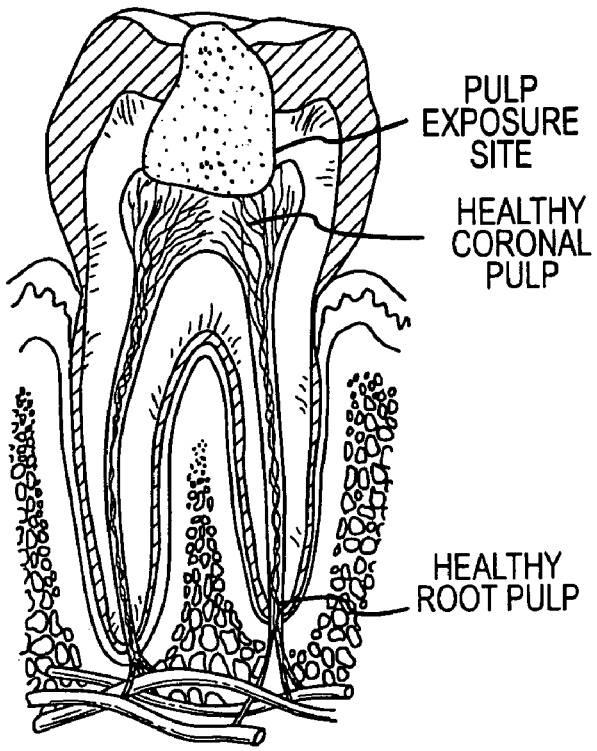
FIG. 8 illustrates treating asymptomatic caries according to another aspect of the invention.
Figure 9:
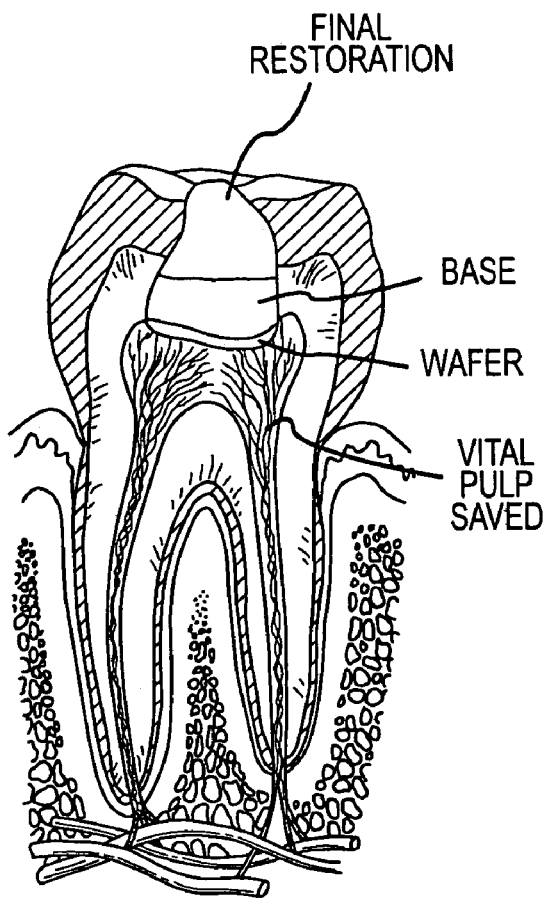
FIG. 9 further illustrates asymptomatic treating caries according to the invention.

Another aspect of the invention includes methods of treating dental conditions using the wafers and devices of the present invention. One example of such a condition treatable by the methods of the invention is asymptomatic caries. FIG. 8 illustrates the anatomy of a tooth afflicted with asymptomatic caries that minimally invades the healthy coronal pulp. To treat asymptomatic caries, the decay/demineralized enamel and dentin is removed and the pulp exposure enlarged to a diameter of 0.5 to 1.0 mm. A tissue scaffold material comprised of PLLA, PDLLA, PGA or PLGA, co-polymer, optionally patterned with calcium phosphate or calcium phosphate plus fluoride and shaped into a cylindrical wafer having a diameter to correspond with the diameter of the hole exposing the pulp as illustrated in FIG. 9. The wafer is hydrated in a physiologically acceptable fluid comprised, for example, of phosphate buffered saline, and is inserted into the hole so that the bottom end of the wafer is in contact with the pulp tissue in the coronal pulp.

A cement base or liner, for example, one comprised of a mixture of 60 to 80% tetra-calcium phosphate and 20 to 40% di-calcium phosphate is applied to cover the wafer and the upper recesses of the fill hole. Examples of suitable cement bases or liners include those described, for example, in U.S. Pat. Nos. 6,398,859, 6,210,759, 6,206,959, 6,1877,838, 6,114,408, 6,001,897, or U.S. published application No. 2002/0137812. Alternatively, or in addition, a composition that promotes remineralization of the dentin that contains calcium phosphate with or without flouride, as described for example, in U.S. Pat. Nos. 5,037,639, 5,268,167, 5,437,857, 5,460,803, 5,534,244, 5,562,895, 6,000,341, or 6,056,930 may be added in the region of the dentin. The cement and/or remineralization composition is then covered with a standard permanent dental restorative material such as a composite resin or dental amalgam. After a sufficient period of time, typically about 1 week, cells from the exposed portion of the coronal pulp proliferate and infiltrate the tissue scaffold wafer and produce the components necessary to regenerate the dentin. After a period of about 45-60 days, the tissue scaffold wafer degrades leaving intact healthy dental tissue.

B. Replacing Root Canal Therapy

Figure 10:
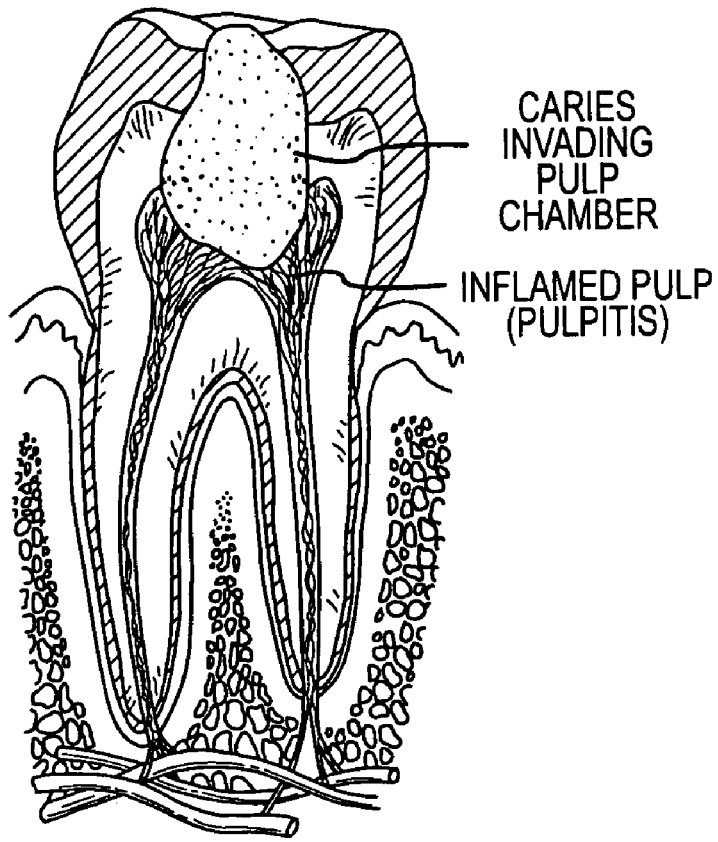
FIG. 10 illustrates treating coronal pulp carries according to another aspect of the invention.

Still other conditions treatable by the methods of the invention are those that typically require root canal therapy. Injury or infection of adult dental pulp often necessitates such therapy. Root canal therapy is commonly used in the case of severe caries where a substantial portion of the dentin and pulp tissue has been degraded, often into the vicinity of the root canal (FIG. 10).

Figure 11:
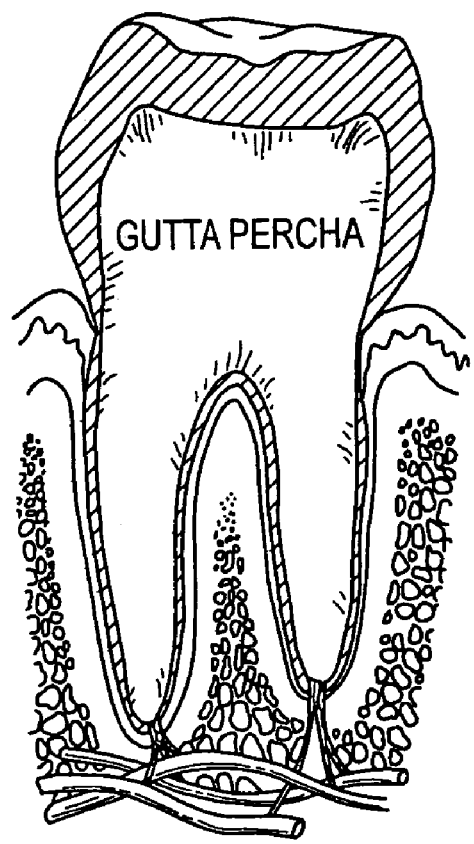
FIG. 11 illustrates a tooth treated with a root canal procedure according to the prior art.

Root canal therapy completely devitalizes a tooth and hence terminates dentin formation and subsequent maturation. Unfortunately, the synthetic materials typically utilized to replace lost tooth structure are not capable of completely replacing the function of the lost tissue, and often fail over time. In a root canal procedure according to the prior art (FIG. 11), the entire pulp tissue and some of the dentin is removed. Gutta-percha is used to fill the void formed in the root canal and coronal regions of the tooth, a resin or amalgam filling is the used to replace the pulp, and often a metal or porcelain crown is cemented into place. Typically a root canal procedure leaves a devitalized tooth that is prone to fracture and subsequent loss.

Rather than destroy all remaining pulp leaving a devitalized tooth, the present invention eliminates the need for root canal therapy while preserving the remaining pulp and regenerating new dentin.

Figure 12:
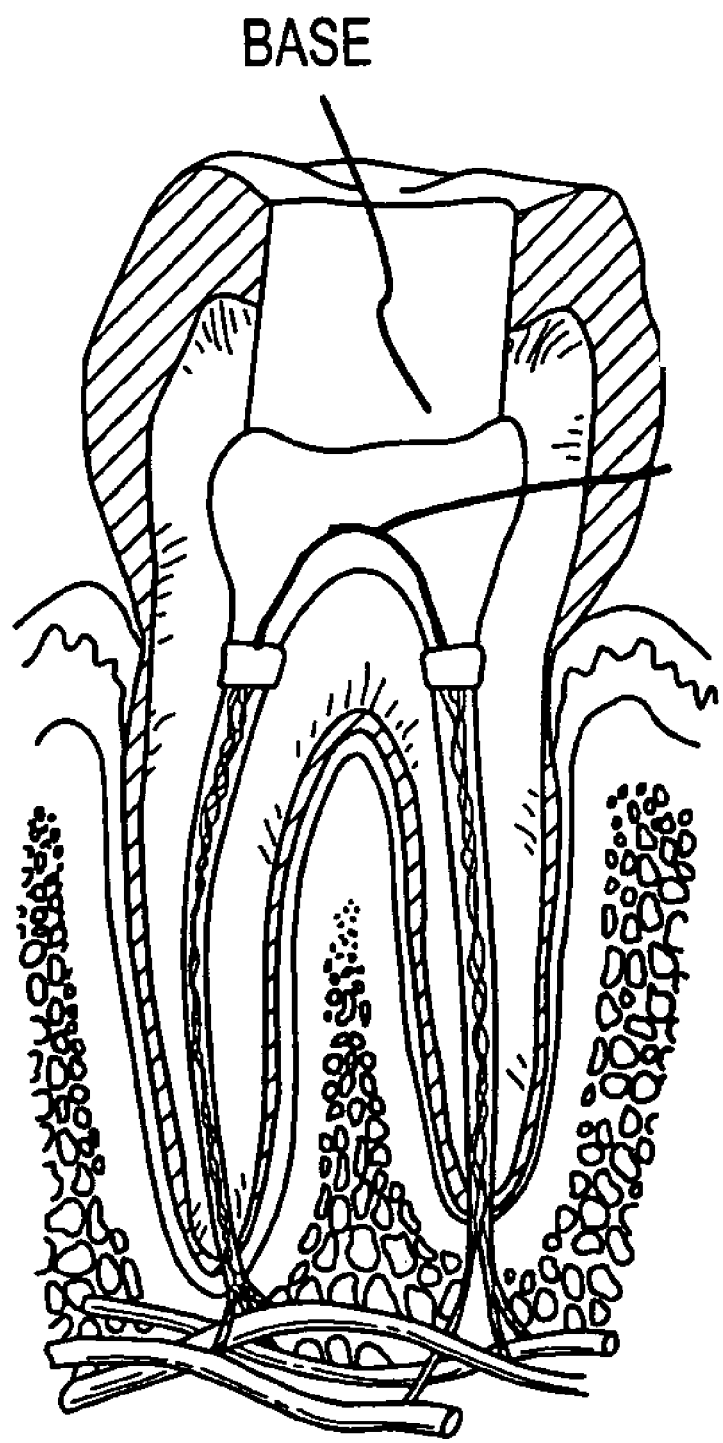
FIG. 12 illustrates a replacement for a root canal according to another aspect of the invention.

FIG. 12 illustrates a procedure that replaces root canal therapy according to the present invention. A pulpotomy is performed whereby the coronal pulp is removed to the level of the root canals. One or more tissue scaffold shaped into a cylindrical wafer having a corresponding diameter of about 0.5 mm to 1 mm to correspond with the diameter of the orifice of the root canal is inserted to contact the pulp tissue remaining in the root canal.

In one practice, one or more of the wafers includes 1-100 μg of a morphogen such as a member of the TGF-β superfamily, for example, BMP-2, BMP-4, BMP-7 and/or GDF5. A cement base (FIG. 9), for example, one comprised of a mixture of 60 to 80% tetra-calcium phosphate as mentioned above, is applied to cover the wafer and the upper recesses of the fill hole. Alternatively, or in addition, a composition that promotes remineralization of the dentin that contains as mentioned above may be added in the region of the dentin The cement and/or remineralizing composition is then covered with a standard permanent dental restorative material such as a composite resin or dental amalgam. After a sufficient period of time, typically about one week, cells from the exposed pulp tissue infiltrate the tissue scaffold wafers and produce the components that regenerate the dentin.

Referring back to FIG. 13, In another practice of the foregoing methods, the morphogens are embedded in the hydrogel plug 108 that is applied over the top of the tissue scaffold wafer prior to sealing the hole with the cement and/or remineralization composition. In this practice, the morphogen gradually diffuses from the hydrogel into the tissue scaffold matrix over time.

In another practice, where very little or no healthy pulp tissue 70 remains in the tooth, the tissue scaffold wafer inserted into any of the root canal or coronal pulp chamber may be pre-seeded with dental pulp stem cells. Dental pulp stem cells may be obtained and identified, for example, according to the methods described in PCT publication WO 02/07679. These dental pulp stem cells are cultured in vitro and seeded into the tissue scaffold wafer according to the methods described, for example, in U.S. Pat. Nos. 5,885, 829, 6,281,256, in U.S. Pat. Publication No. 2002/0119180 A1 or by Young et al., (2002) *J. Dent. Res.* 81 [10] p 695-700. A culture of about $5 \times 10^6$ dental pulp stem cells will be sufficient to regenerate the damaged pulp tissue and other structures.

C. Anti-Inflammatories and Antibiotics.

In certain practices of the forgoing methods, an anti-inflammatory agent and/or and antibiotic agent is included in the tissue scaffold wafer. The anti-inflammatory agent not only provides and analgesic effect in the vicinity of the tooth, but also promotes reduction of pulpitis. As mentioned in the Background herein before, the morphogenic agent BMP-7, when directly applied as a moistened powder to the tooth was not effective in promoting pulp growth in ferrets having pulpitis, but was effective in promoting pulp growth in non-inflamed tissue. BMP-7 was effective in stimulating pulp growth in ferrets having pulpits when delivered from cells transduced with a gene encoding BMP-7.

While not being bound by theory, it is believed that the difference between the effectiveness of directly applied BMP-7 versus ex-vivo cellularly produced BMP-7 is due to the presence of inflammation and the timing of delivery. Directly delivered BMP-7 remains active for only a short period of time during which inflammation of the pulp persists. It is believed that inflamed pulp tissue is not responsive to the activity of morphogens such as BMP-7. However, cellularly delivered BMP-7 is continuously produced over the time period required for the inflammation to recede, after which time the non-inflamed tissue become responsive to the morphogen. The present invention eliminates the need to use ex-vivo transgenic cells to deliver the morphogen over time because the morphogen is embedded in the tissue scaffold wafer (or in a hydrogel) which gradually releases the morphogen over time as the wafer degrades. In addition, the presence of the anti-inflammatory agent in the wafer promotes more rapid recovery of the inflamed tissue, making it responsive to the morphogen. Further, when an antibiotic is included, its presence of not only reduces the risk of infection, but also reduces the likelihood of an inflammatory response associated therewith.

As an alternative to embedding the anti-inflammatory agent and/or the anti-biotic in the tissue scaffold or hydrogel, the subject's tooth may be treated by topical application of the agent or anti-biotic at one or more sessions after the wafer has been implanted. This direct treatment has the benefit of permitting the therapist to precisely control the amount of anti-inflammatory agent or anti-biotic being applied to the tooth over time.

To aid the practitioner in making and using the tissue scaffold wafers 89 that may be used in the practice of this invention, the following Examples are provided as a guide to exemplify the manufacture, testing and modifications of the wafers used in the invention.

EXAMPLE I

Fabricating Hollow Tube Tissue Scaffold Wafers of PLA, and PDLLA and PLGA

A. Materials

PLA, PDLLA, and the 85/15 and 50/50 PLGA were purchased from Medisorb (Cincinnati, Ohio), chloroform from Mallinckrodt (Paris, Ky.), polystyrene standards from Polysciences (Warrington, Pa.), aluminum backed tape from Cole-Parmer (Chicago, Ill.), phosphate buffered saline and DMEM medium from Gibco (Grand Island, N.Y.), Tmax film from Kodak, Lewis rats, 250 to 300 g, from Charles River (Wilmington, Mass.), and methoxyflurane from Pitman-Moore Inc. (Mundelein, Ill.).

Molecular weights of the various polymers were determined by gel permeation chromatography (Perkin-Elmer, Series 10, Newton Centre, Mass.), using polystyrene standards to generate a calibration curve. PLA had a molecular weight ($M_w$) of 74,000 ($M_w/M_n$=1.6); poly-(D,L lactic) acid had $M_w$=77,000 ($M_w/M_n$=1.8); 85/15 copolymer had $M_w$=69,000 ($M_w/M_n$=1.9); 50/50 copolymer $M_w$=43,400 ($M_w/M_n$=1.43). Differential scanning calorimetry was utilized to confirm the amorphous nature of all of the polymers except PLLA, which exhibited the expected crystallinity.

B. Device Fabrication

Hollow tubes were formed by a two-step process; porous films of the polymers were first fabricated, and these films were then formed into hollow tubes. To fabricate porous films, the polymer was dissolved in chloroform to form a 1.56% solution (w/v). Eight ml of this solution was cast into a 5 cm glass petri dish covered with a sheet of aluminum backed tape. Sieved sodium chloride crystals between 150 and 250 μm in diameter were dispersed evenly over the solution (0.375 g NaCl/dish), and the chloroform was allowed to evaporate at room temperature. A polymer film with entrapped NaCl particles resulted.

The salt particles were leached out of the film by immersion in 800 ml of deionized water for 48 hr at 37° C. with constant shaking. The water was changed every 8 hr during the leaching period. This procedure yielded a highly porous, thin membrane. In one practice sections were cut from the resulting films (1.3.times.1.5 cm), with a razor blade, and rolled around Teflon cylinders with an outer diameter of 0.32 cm. The surfaces of the films that were adjacent to the aluminum backed tape were always placed adjacent to the Teflon cylinder.

In another practice, Teflon cylinders having diameters that correspond to the diameter of holes to be drilled in the tooth of a subject are selected. The height of the cylinder is similarly selected to correspond to the depth of the portion of the hole drilled into the dentin layer. Typical selected diameters sizes are between about 2 to 5 mm. Typical heights are about 1 to 3 mm. Sections of the membrane are cut from the resulting films to correspond to the diameter of the Teflon cylinders and leaving about 10% to 30% of overlapping material over the ends.

The overlapping ends of the film were sealed together by briefly exposing one edge to chloroform, and manually pressing the overlapping ends together. The chloroform temporarily dissolved the polymer on the surface of each of the overlapping ends, and after the chloroform evaporated the overlapping ends were sealed together. The tubes were then slipped off of the teflon template. The ends were closed by placing a circular piece of the same porous films over the ends, and sealing as above with chloroform. Tubes 1.5 cm long, with an inner diameter of 0.32 cm resulted. Tubes were lyophilized to remove residual solvent, and sterilized by exposure to ethylene oxide for 24 hr at room temperature. Tubular tissue scaffolds formed by this method are illustrated in FIG. A.

In an alternative practice, tubular tissue scaffolds are formed with a concentric tubular lumen. To form tissue scaffolds with concentric lumens, a set of tubular scaffolds varying in diameter by a selected spacing distance are made according to the steps outlined above, except, that prior to sealing the ends, the set of tubular scaffolds are inserted into one another to share a common origin about a circle. This results in an interior lumen having concentric luminal spaces as illustrated in FIG. A1. After arranging the concentric tubes, the ends are sealed with a circular strip of the porous membrane as described above.

In another alternative practice tubular tissue scaffolds are formed with a spiral tubular lumen. Instead of wrapping the porous membrane around a Teflon cylinder, the membrane is positioned on top of Teflon tape having a thickness of about 0.1 to about 0.3 mm. The Teflon tape and membrane together are then rolled into a tubular shape of the desired diameter. Rolling in this fashion results in a spiral arrangement of the membrane strip with a separation distance across adjacent walls of the spiral equal to the thickness of the Teflon strip as depicted in FIG. A2. The bottom of the rolled strip is sealed with a circular membrane strip as before, the Teflon tape is removed and the top is sealed with another circular membrane, resulting in a closed tubular tissue scaffold with a spiral shaped lumen.

The pore structure of films formed with the particulate leaching technique can be controlled by varying the ratio of polymer to salt in the film fabrication process. Films fabricated with a polymer/salt ratio of 1/3 exhibited large pores on the air surface, approximately the size of the salt particles utilized to form the pores. These films had much smaller pores on the surface of the film exposed to the teflon tape-coated glass surface. These pores corresponded closely in structure to the salt particles utilized to create the device porosity.

Decreasing the ratio of polymer to salt from 1/3 to 1/24 resulted in the formation of larger pores on the air surface of the films, and these pores were not as uniform as the pores formed at lower salt loadings. Larger pores also formed on the film surface exposed to the glass dish as the polymer to salt ratio was decreased. At a very low ratio (1/12) both sides of the films exhibited a similar pore structure.

Films fabricated from all polymers (PLLA, PDLLA, 50/50 PLGA, and 85/15 PLGA) could be readily formed into hollow tubes. There was no significant differences in the pliability of films formed from the different polymers. However, films formed using a polymer/salt ratio lower than 1/12 were quite brittle, and the manipulation needed to form tubes from these films often resulted in their fracture.

Films fabricated using a polymer/salt ratio of 1/3 were utilized to fabricate the tubular devices used in all subsequent studies. These films had a thickness of 320±50 μm (mean.±. sd, n=36), a porosity of 87±0.4% (n=12), and a volume average pore diameter of 150±50 μm (n=12).

Devices fabricated from all four polymers resisted compression by moderate forces (50 mN), but the ability of devices to withstand a larger compressional force (150 mN) was dependent on the polymer used in fabrication. PLLA tubes exhibiting the least compression under this force, and 50/50 PLGA devices exhibiting the greatest. The compression was viscoelastic in all cases, as the devices only partially decompressed after the force was removed. While devices fabricated from PLLA and PDLLA consistently resisted this load, PLGA devices did not exhibit a consistent response. The 50/50 PLGA tubes showed the greatest variability, as testing of multiple tubes gave widely varying results. Devices which compressed greater than 50% after force application typically showed little elastic recoil after the force was removed. Thus, devices which compressed more than this were considered to fail at this loading, and the failure rates of devices fabricated from the various polymers is given in Table 7.

TABLE 7

In vitro and In vivo Compression Test Failure of Devices

| | In vitro | | In vivo | |
| --- | --- | --- | --- | --- |
| Polymer | Number of Polymer Samples | Sample Failure Rates | Number of Polymer Samples | Samples Failure Rates |
| PLLA | 6 | 0% | 2 | 0% |
| PDLLA | 5 | 20% | 6 | 0% |
| 85/15 PLGA | 5 | 40% | 9 | 44% |
| 50/50 PLGA | 16 | 58% | 6 | 50% |

A. Compression testing was performed with a force of 150 mN. A device was considered to fail if it compressed to less than 50% of the original diameter.
B. Devices were implanted into the mesentery or omentum of Lewis rats for 7-28 days. Histological sections were examined, and devices were considered to fail if they compressed and did not maintain their original, tubular shape.

Different erosion times may be required of devices utilized to engineer various tissues. The erosion kinetics of devices fabricated in this example was governed by the polymer utilized to fabricate the devices. The time for complete erosion could be varied between 10 weeks and over a year by varying which polymer was utilized to fabricate the device.

The compression resistance of the tubular devices fabricated in this manner were dependent on the polymer utilized to fabricate the devices. Devices fabricated from both PLLA and PDLLA resisted compressional forces and maintained their structure both in vitro and in vivo. Devices fabricated from PLGA did not resist compressional forces as well either in vitro or in vivo. The compression resistance of tubes fabricated from 50/50 PLGA was inconsistent at high compression forces (150 mN).

The tubular devices and tissues are only exemplary of how a polymer matrix can be used to provide a 3-D structure required to match a native tissue structure. Particular devices optimized for oral tissues can thus be generated.

EXAMPLE II

Making PGA Tubular Tissue Scaffolds Stabilized by Spray Casting With PLLA and PLGA Another method to stabilize PGA meshes, described in this example, is to atomize solutions of poly (L-lactic acid) (PLLA) and a 50/50 copolymer of poly (D,L-lactic-co-glycolic acid) (PLGA) dissolved in chloroform and to spray over meshes formed into hollow tubes. The PLLA and PLGA coated the PGA fibers and physically bonded adjacent fibers. The pattern and extent of bonding was controlled by the concentration of polymer in the atomized solution, and the total mass of polymer sprayed on the device. The compression resistance of devices increased with the extent of bonding, and PLLA bonded tubes resisted larger compressive forces than PLGA bonded tubes. Tubes bonded with PLLA degraded more slowly than devices bonded with PLGA.

PGA fiber meshes are stabilized by physically bonding adjacent fibres using a spray casting method. Poly L-lactic acid (PLLA) or a 50/50 copolymer of lactic and glycolic acid (PLGA) was dissolved in chloroform, atomized, and sprayed over a PGA mesh formed into a tubular structure. Following solvent evaporation, a physically bonded structure resulted, and the pattern and extent of PGA fiber bonding was controlled by the processing conditions.

These tubular devices were capable of withstanding large compressive forces in vitro (50-200 mN), and maintained their structure in vivo. The specific mechanical stability was dictated by the extent of physical bonding and the polymer utilized to bond the PGA fibers.

A. Tube Fabrication and Characterization

Rectangles (1.3.times.3.0 cm) of the non-woven mesh of PGA fibers were wrapped around a teflon cylinder (o.d.=3.0 mm) to form a tube, and the two overlapping ends were manually interlocked to form a seam. The teflon cylinders were then rotated at 20 rpm using a stirrer (Caframo; Wiarton, Ontario, Canada). Solutions of PLLA and PLGA dissolved in chloroform (1-15% w:v) were placed in a dental atomizer (Devilbus Corp.), and sprayed over the rotating PGA mesh from a distance of 6 inches using a nitrogen stream (18 psi) to atomize the polymer solution.

The PLGA and PLLA had molecular weights (Mw) of 43,400 (Mw/Mn=1.43) and 74,100 (Mw/Mn=1.64), respectively. Molecular weights were determined by gel permeation chromatography, as described above.

While PLLA and copolymers of lactic and glycolic acid are soluble in chloroform, PGA is very weakly soluble in this solvent. Thus, the PGA fibers are largely unchanged by this process. After spraying was completed, the tubes were lyophilized to remove residual solvent, removed from the teflon cylinder, and cut into specific lengths. The tubes were sterilized by exposure to ethylene oxide for 24 hr, followed by degassing for 24 hr.

The mass of PLLA and PLGA that bonded to the PGA scaffolds was determined by weighing PGA devices before and after spraying. Electron microscopy, mechanical analysis and erosion characteristics were as described above.

1. Bonding Tubes With PLLA

To determine whether PGA scaffolds could be stabilized by physically bonding adjacent fibers, chloroform containing dissolved PLLA (1-15% w:v) was sprayed over the exterior surface after the PGA mesh was wrapped around a teflon cylinder to form a tube. The PLLA formed a coating over the exterior PGA fibres after the solvent evaporated, and physically bonded adjacent fibres. The tubes formed in this manner could be easily removed from the teflon cylinder for characterization and use.

The pattern of bonding was controlled by the concentration of the PLLA in the atomized solution, even though the time of spraying was adjusted to maintain an approximately constant mass of PLLA on the devices under the various conditions. Spraying with a solution containing 1 or 5% PLLA resulted in extensive bonding of PGA fibres without significantly blocking the pores of the PGA mesh. Spraying with a 10% solution of PLLA also bonded fibers, but resulted in the formation of a PLLA film on the exterior surface of the PGA mesh that contained only small pores. Spraying with a solution containing 15% PLLA had a similar effect, although the polymer film that formed was less organized. In all cases, the PLLA coated and bonded fibers only on the exterior surface of the PGA mesh, as no coating or bonding of fibers was observed on the interior surface of the PGA mesh.

The compression resistance of bonded tubes was assessed in vitro to determine which patterns of bonding resulted in the most stable devices. Unbonded tubes were completely crushed by a force of 5 mN, but bonded tubes were capable of resisting forces in excess of 200 mN. However, the ability of bonded tubes to resist a given compressional force was dependent on the pattern of bonding. For example, tubes bonded with 1 or 15% PLLA were significantly compressed by a force of 200 mN, while tubes bonded with a solution of 5 or 10% PLLA were only slightly compressed by this force. The compression was viscoelastic in all cases, as the devices only partially decompressed after the force was removed. Uniform properties were observed with respect to the position along and around a tube.

To determine if the extent, as well as the pattern, of bonding could vary the compression resistance of tubes, an atomized dispersion of 5% PLLA was then sprayed over the devices for different times. Lengthening the spraying time from 10 to 60 seconds increased the mass of PLLA on the devices. Infrequent bonds between adjacent fibers resulted from spraying for 10 seconds. Spraying for more extended periods increased the PLLA coating over the PGA fibers, and the extent of bonding.

The ability of these tubes to resist compressional forces and maintain their shape was quantitated again using thermal mechanical analysis. The compression resistance strongly depended on the extent of bonding, as tubes that were more extensively bonded had a greater resistance to deformation. The compression that did occur under these conditions was again a combination of a reversible, elastic strain, and an irreversible deformation. Some tubes were also exposed to an aqueous environment before testing to determine whether this environment for 24 hr would destabilize the tubes. The aqueous environment had a slight, detrimental effect on the stability of bonded tubes, but they were still capable of resisting large compressive forces.

2. Bonding Tubes With PLGA

To determine whether this technique of stabilizing PGA devices could be utilized with a variety of polymers, the previous study was repeated using a 50/50 copolymer of lactic and glycolic acid. The mass of polymer bonded to the devices and the extent of physical bonding was again regulated by the time an atomized dispersion of the bonding polymer was sprayed over the PGA fibers. Once again, bonding increased the compression resistance of devices formed into a tubular structure. However, these devices were not able to resist the same compressional forces as PLLA bonded devices.

Tubes bonded with PLLA were capable of resisting forces up to 200 mN, while tubes bonded with PLGA were only capable of resisting forces slightly greater than 50 mN. The difference between devices stabilized with PLLA and PLGA was even more striking when the devices were tested after immersion in phosphate buffered saline for 24 hr. PLGA bonded tubes, in contrast to PLLA bonded tubes, were significantly weakened by this treatment.

The bonding approaches described herein permit a variety of bonding polymers to be utilized, and allows the fabrication of various three-dimensional scaffolds. It also results in bonding only of the outermost fibres of the device in contrast to other methods. This preserves the desirable features of the PGA mesh (high porosity, high surface area/polymer mass ratio) throughout the interior sections.

This approach also allows both the extent and pattern of bonding to be easily controlled. Extensive coating and bonding of fibers resulted when the polymer concentration in the atomized solution was low (1-5%). Increasing the concentration of polymer in the atomized solution to 10% resulted in the formation of a relatively smooth film over the external surface of PGA meshes, and utilizing a 15% solution resulted in the formation of a fibrous, nonhomogeneous film over the PGA meshes. Increasing the polymer concentration raises the viscosity of this solution, and this likely increases the droplet size which is formed during the atomization process. This will effect how these droplets penetrate the PGA mesh, how they aggregate on the PGA mesh, and the rate of solvent evaporation. All of these factors will effect the pattern of bonding.

For delivery into a hole in a subject's tooth, the tissue delivery device should preferably maintain a pre-configured geometry in the face of external forces during the process of tissue development. The magnitude of the compressive forces that are exerted on implanted devices by the surrounding tissue are unclear and will vary depending on the implant site. The magnitude of forces utilized in the present example to quantitate the compression resistance of devices in vitro was 50-200 mN. This results in pressures ranging from approximately 50-200 mm Hg (assuming complete and continuous contact between the TMA compression tip and the tube). These pressures are in the same range observed in blood vessels.

EXAMPLE III

Making a PLGA Sponge Matrix Tissue Scaffold Wafer

Pellets of an 85:15 copolymer of D,L-lactide and glycolide (PLGA) was purchased from Boehringer Ingelheim (Henley, Montvale, N.J., USA), and utilized to fabricate polymer matrices in all experiments. The intrinsic viscosity of the polymer was about 1.3-1.7. Polymer pellets were ground using a Tekmar grinder (Bel-Art Products, Pequannock, N.J., USA), and sieved to obtain particles ranging from 106 to 250 μm. In certain experiments the polymer particles were mixed with sodium chloride particles (Mallinckrodt, Paris, Ky., USA). The salt particles were sieved to yield a range of sizes, and the weight ratio of NaCl:PLGA masses ranged from 0 to 50. In all cases, the total mass of PLGA and NaCl was held constant at 0.8 g. The mixtures of PLGA and NaCl were loaded into a KBr die (1.35 cm in diameter; Aldrich Chemical Co., Milwaukee, Wis., USA), and compressed at 1500 psi for 1 minute using a Carver Laboratory Press (Fred S. Carver, Inc., Menominee Falls, Wis., USA) to yield solid discs (thickness=3.4 mm). The samples were then exposed to high pressure $CO_2$ gas (800 psi) for 48 hours to saturate the polymer with gas. A thermodynamic instability was then created by decreasing the gas pressure to ambient pressure. This led to the nucleation and growth of $CO_2$ pores within the polymer matrices. The NaCl particles were subsequently removed from the matrices by leaching the matrices in $ddH_2O$ for 48 hours. All processing steps were performed at ambient temperature.

Porous sponges were also fabricated using a previously described solvent casting-particulate leaching technique. (A. G. Mikos, A. J. Thorsen, L. A. Czerwonka, Y. Bao, and R. Langer, "Preparation and characterization of poly(L-lactic acid) foams," Polymer, 35, 1068-1077 (1994).) In this process, PLGA was dissolved in chloroform (Mallinckrodt; Paris, Ky., USA) to yield a solution of 10% (w:v), and 0.12 ml of this solution was loaded into Teflon cylinders (diameter 0.5 cm; Cole Parmer) packed with 0.4 g of sodium chloride particles sieved to a size between 250 and 500 mm. Following solvent evaporation, polymer films with entrapped salt particles (3 mm thick) were carefully removed from the molds. The salt was removed by immersing films in distilled water for 48 hrs.

The porosity of samples was initially determined by gross measurements and weights after processing using the following equation:

$$\text{porosity}(\%) = 1 - [(\text{weight/volume})/(\text{density of polymer})] \times 100 \quad \text{Eqn. 1}$$

Thermogravimetric analysis was utilized to determine the amount of salt residue that remained in the sponge after leaching. Matrices were heated from 150° C. to 300° C. at a constant rate of 10° C./min, and the residual mass was monitored.

Photomicrographs showed that gas foaming, alone, of solid polymer discs led to the formation of highly porous matrices. However, these matrices had a nonporous skin on the external surfaces and the pores were largely closed, as expected from previous studies. (D. J. Mooney, D. F. Baldwin, N. P. Suh, J. P. Vacanti, and R. Langer, "Novel approach to fabricate porous sponges of poly(D,L-lactic-coglycolic acid) without the use of organic solvents," Biomaterials, 17, 1417-1422 (1996).) In contrast, gas-foaming and subsequent leaching of discs containing a high percentage (95%) of large (250<d<425 μm) NaCl particles, according to the invention, led to the formation of highly porous, open pore matrices with no evidence of an external, non-porous skin. The pore structure observed in cross-sections of these matrices was similar to that observed in cross-sections of matrices formed with a SC/PL technique. However, the pore structure of matrices formed from the SC/PL process is often not uniform throughout the matrix due to evaporation of the organic solvent and subsequent increase in the polymer concentration of the remaining solution entrapped within the salt bed. For example, the surface of these matrices that is adjacent to the glass coverslip during processing is shown in photomicrographs to be typically less porous than the remainder of the matrix. In contrast, the pore structure of gas foamed-particulate leached (GF/PL) matrices was uniform throughout the matrix and on the exterior surfaces. TGA analysis of matrices indicated that negligible amounts of NaCl remained after leaching. There was a trace of a white residue left in the dish. To confirm that the gas foaming was responsible for the formation of stable matrices, control samples were compression molded, but not foamed. Leaching of the NaCl from these matrices led to complete breakdown of the matrices.

The ratio of NaCl:PLGA and the size of NaCl particles in GF/PL matrices were varied to determine the range of porosity and pore structure that could be obtained with this process. The gross porosity of these matrices increased from 85.1%.±.2.3 to 96.5%.±.0.5 as the ratio of NaCl:PLGA was similarly increased. At constant NaCl (95%), the increase in salt particle diameter had very little effect on the overall porosity. However, photomicrographs showed that as the salt diameter was increased, the pore size increased in parallel.

The stability of the matrices was assessed using compressive and tensile mechanical tests. In general, the GF/PL matrices exhibited improved mechanical properties as compared to the SC/PL matrices. The average compression moduli were 159.±.130 kpa and 289.±.25 kPa for the SC/PL and GF/PL matrices, respectively. The average tensile moduli were 334.±.52 kPa for the SC/PL matrices and 1100.±.236 kPa for the GF/PL matrices (Table 8). This data represents a 80% increase in compression strength and a 300% increase in tensile strength.

TABLE 8

Gross porosity of sponges.

| NaCl Concentration (%) | Diameter (µm) | | |
|---|---|---|---|
| | 106-250 | 250-425 | >425 |
| 80 | — | 85.1 ± 2.3 | — |
| 90 | 87.3 ± 1.9 | 91.5 ± 1.4 | — |
| 95 | 93.9 ± 0.9 | 94.6 ± 0.9 | 95.0 ± 0.8 |
| 97 | — | 96.5 ± 0.5 | — |

EXAMPLE IV

Making Tissue Scaffold Matrix Sponges by Foaming Casted Polymer Disks

Pellets of poly L-lactic acid [PLLA], a 50:50 copolymer of D,L-lactide and glycolide (50:50 PLGA) with intrinsic viscosity (i.v. of 0.2 dL/g), a 75:25 PLGA copolymer (i.v.=1.3), and an 85:15 PLGA copolymer (i.v.=1.4) were obtained from Boehringer Ingetheim (Henley, Montvale, N.J., USA). PGA, 50:50 PLGA (i.v.=0.8) and 85:15 PLGA (iv=0.63) were purchased from Medisorb (Cincinnati, Ohio, USA). 85:15 PLGA (i.v.=3.63) was obtained from Purasorb (Lincolnshire, Ill., USA).

The solid polymer (PLLA, PLGA, PGA) was ground (after freezing with liquid nitrogen) using a Scienceware Micro-Mill (Bel-Art Products, Pequannock, N.J., USA) and sieved to a diameter of 106-250 5 µm. NaCl, obtained from Fisher Scientific (Pittsburgh, Pa., USA), was sieved to a diameter of 250-425 5 µm for use in certain experiments. Solid polymer disks were formed by placing 150 mg polymer (PGA, 50:50 PLGA, 75:25 PLGA, 85:15 PLGA, and PLLA) into a round stainless steel KBr die with diameter 1.35 cm (Aldrich Chemical Co., Milwaukee, Wis., USA) and compressing for 60 seconds at 1500 psi in a Carver Laboratory Press (Fred S. Carver, Inc., Menominee Falls, Wis., USA). This method yields solid disks to be foamed. All samples were fabricated in triplicate.

The disks were foamed in a high pressure vessel using $CO_2$, $N_2$, or He at 850 psi. After the disks were equilibrated (148 hours) with the gas, the pressure was reduced to ambient. The resulting thermodynamic instability caused nucleation and growth of gas pores within the polymer matrix. 85:15 solid polymer disks (i.v.=1.4) were foamed for 1 hour in $CO_2$ and the pressure was released at different rates (1, 2.5, 5, 10 minutes) to determine if the rate of pressure release affects the final structure of the sponges. All processing steps were performed at ambient temperature.

Polymer/NaCl disks were fabricated in a similar way using 40 mg polymer and 760 mg NaCl, compressed into disks. Following foaming, the disks were placed in distilled water in order to remove the NaCl. This leaching solution was changed several times over the course of about 18 hours. The disks were considered to be completely leeched when the leeching solution did not give a precipitate with AgNO3. If Cl− is present in solution, it precipitates with Ag+ to form a white precipitate. The failure of this precipitate to form indicated that the NaCl is completely removed from the scaffolds. The disks were then air dried overnight, measured and weighed, and stored in a desiccator under vacuum. The polymer disks were measured and weighed immediately following foaming, then stored in a desiccator under vacuum.

In order to calculate the porosity of the foamed disks, a boley gauge was used to measure the diameter and thickness of each disk. The disks were weighed on a Mettler balance and the following equation was used: (d=polymer density, g=disk wt, cm3=calculated disk volume).

porosity=100 [1−(g/cm3)/d]

a Foaming Solid Polymer Disks

In the first series of experiments, solid polymer disks were foamed to investigate the role of the gas type, pressure release rate, and polymer composition and molecular weight on the porosity of polymer matrices. 85:15 PLGA matrices were foamed for 1 hour with several different gases ($CO_2$, $N_2$, He). Significant porosity resulted from foaming with $CO_2$ as compared to $N_2$ and He. The "prefoam" porosity refers to the calculated porosity following disk preparation, but prior to high pressure equilibration. Visualization of matrices foamed with $CO_2$ revealed a highly porous matrix consisting largely of closed pores.

In the next study, the rate of release of pressure was varied from 1 to 10 minutes total time. The porosity of the matrices was relatively constant regardless of pressure release rate, except in the case of a very rapid release, when the gas froze within the chamber. This led to a small decrease in the matrix porosity.

The effect of the polymer composition was investigated by using different copolymer ratios of PLGA (pure PGA, 50:50, 75:25, 85:15 PLGA and pure PLLA). Neither PGA nor PLLA foamed appreciably. The copolymers all foamed to a porosity greater than 90%. In fact, the 75:25 copolymer foamed so extensively that it did not maintain its integrity in the pressure release/gas expansion phase and literally fell apart. Hence, no porosity value could be calculated for that sample.

In order to study the effect of polymer molecular weight on pore formation, disks of 85:15 PLGA with intrinsic viscosity (i.v.) ranging from 0.63 to 3.59 dL/g were foamed in 850 psi CO2 for 24 hours with a pressure release of 2.5 minutes. The high i.v. PLGA led to matrices with relatively low porosity, whereas the lower i.v. PLGA resulted in much higher porosity.

b Foaming Polymer/NaCl Disks

In the second series of experiments, NaCl was incorporated into the polymer disk for the purpose of creating an open pore structure. Different variables (equilibration time and polymer composition) were studied in order to determine their effects on the structure and stability of the scaffolds. The results of the first series of experiments led us to use $CO_2$ as the foaming gas, and a pressure release time of 2.5 minutes in this series of experiments. Examination of a typical matrix formed by foaming 85:15 PLGA with NaCl in $CO_2$ shows a highly porous structure with largely open, interconnected pores.

In the first study, the equilibration time was varied from 1 to 48 hours. The porosity of the matrices was relatively constant for equilibration times greater than 6 hours, but decreased for equilibration times under 6 hours. Matrices fabricated with various equilibration times were subsequently tested to determine if the equilibration time affected their mechanical properties. Even though maximal porosity was achieved with 6 hours of gas equilibration, a stronger scaffold was produced with longer equilibration times.

The polymer Composition was next varied to determine if results similar to those in the first series of experiments would be obtained. Copolymers of PLGA led to a much greater porosity than did the homopolymers PGA and PLLA. Both the PLLA and PGA disks disintegrated in the leaching process, indicating that little, if any, foaming had occurred. Even though all PLGA copolymers led to matrices with similar porosities, the matrices fabricated from PLGA with higher lactic acid content were more rigid.

EXAMPLE V

Tissue Scaffold Sponge Matrix Wafers Made of PLA or PLGA—With PVA

The present example concerns sponges fabricated from poly-L-lactic acid (PLA) infiltrated with polyvinyl alcohol (PVA). Highly porous sponges (porosity=90-95%) were fabricated from PLA using a particulate leaching technique. To enable even and efficient cell infiltration, the devices were infiltrated with the hydrophilic polymer polyvinyl alcohol (PVA).

A. Sponge Fabrication and Characterization

Porous sponges were formed from PLA and an 85/15 copolymer of D,L lactic acid and glycolic acid (85/15 PLGA) (Medisorb; Cincinnati, Ohio) using a variation of a previously described particulate leaching technique (Mikos et al., 1994). The PLA and 85/15 PLGA had molecular weights ($M_w$) of 74,000 ($M_w/M_n$=1.6), and 69,000 ($M_w/M_n$=1.9), respectively. Molecular weight determination was performed using gel permeation chromatography with polystyrene molecular weight standards.

The polymers were dissolved in chloroform (Mallinkrodt; Paris, Ky.) to yield a solution ranging from 10-20% (w:v), and 0.12 ml of this solution was loaded into Teflon cylinders (diameter=21.5 cm, height=25 mm; Cole Parmer) packed with 0.4 g of sodium chloride particles sieved to a size between 250 and 500 µm. Following solvent evaporation, polymer films with entrapped salt particles (1 mm thick) were carefully removed from the molds. The salt was removed by immersing films in distilled water for 48 hr. The water bath was changed 3 times daily. The volume of polymer solution and salt mass loading were linearly increased to fabricate thicker sponges.

To infiltrate sponges with PVA (Aldrich Chem. Co.; Milwaukee, Wis.; MW 3000, 75% hydrolyzed) or the Pluronic F 108 surfactant (BASF; Parsippany, N.J.), sponges were immersed for 16 hr in an aqueous solution containing 1-100 mg/mL of PVA or Pluronic in phosphate buffered saline (PBS). The sponges were subsequently removed from the solution, dried, and lyophilized. The mass of devices before and after coating was quantitated to determine the mass of incorporated PVA or surfactant. To determine whether the incorporated PVA was permanently associated with the sponges, some sponges were subsequently soaked in a solution of PBS overnight, air dried at room temperature, lyophilized, and reweighed. All sponges were sterilized before use by exposure to ethylene oxide.

The ability of aqueous solutions to wet the sponges was determined by placing a volume of distilled water equivalent to the void volume of the sponge (as determined using mercury porosimetry) onto one surface of the sponge, and allowing 10 minutes for the solution to soak into the sponge. The sponges were held at a 90° angle, and lightly shaken to remove water not absorbed into the sponge. Sponges were weighed to determine the volume of water which did absorb.

Solid discs were formed from various polymers in the PLGA family using compression molding. These discs were used to measure the contact angle of the polymers with water, and to test the ability of hepatocytes to adhere to the polymer films. Solid polymer discs were utilized in these studies instead of porous three-dimensional sponges as it simplified the analysis (e.g., it is simpler to measure the advancing water contact angle on a two-dimensional film than in a three dimensional sponge).

Discs (0.5 mm thick) were formed from 0.75 g of PLA, polyglycolic acid, poly-D,L-lactic acid, or a 85/15 or 50/50 copolymer of lactic and glycolic acid (all purchased from Medisorb) using a Carver Laboratory Press (Fred S. Carver, Inc.; Menominee Falls, Wis.). The polymer was heated to 185° C., and compressed at 1500 psi. Discs were coated with PVA or Pluronic F108 as described above. Contact angle measurements were made from an advancing water droplet using a goniometer (Rame-Hart, Inc.; Mountain Lakes, N.J.). Reported values represent the mean and standard error of the mean (SEM) calculated from the mean advancing contact angle of a minimum of three films at each condition. The mean advancing contact angle for each film was calculated from a minimum of three measurements.

B Results

Highly porous sponges were formed from PLA and 85/15 PLGA using a previously described technique (Mikos et al., 1993b). The size and shape of devices formed in this manner can be controlled by the geometry of the Teflon mold and the mass of salt particles and polymer loaded into the mold. The porosity and pore size of devices formed with this type of particulate leaching technique can be controlled by varying the ratio of polymer/salt particles and the size of the salt particles (Mikos et al., 1993b). In this study, the ratio of polymer/salt was varied from 0.06 to 0.03 to increase the device porosity from 90.±.1 to 95.±.1.5%, and cylindrical devices 1-5 mm thick (d=2 cm) were fabricated by increasing the mass of polymer and salt from 0.412 to 2.06 grams.

Polymers of the lactic/glycolic acid family are all relatively hydrophobic, as indicated by high contact angles with water. The contact angle of films fabricated from poly-L, lactic acid, polyglycolic acid, poly-D,L lactic acid, and 85/15 and 50/50 copolymers of lactic and glycolic acid were 79.degree±2°, 73.degree±2°, 72.degree±1.degree, 73.degree±2°, and 69. degree±3°, respectively. To determine whether the hydrophobicity of these polymers could be decreased, solid films of PLA were coated with the hydrophilic polymer PVA or a surfactant, Pluronic F 108.

The advancing water contact angle decreased from 79.degree±2° to 23.degree±2° when devices were exposed to PBS containing 10 mg/mL solution of PVA. When PVA solutions ranging from 1 to 100 mg/mL were used for coating, a similar decrease in the contact angle of polymer films was noted. The contact angle of PLA films also decreased from 79.degree±2° to 22.degree±.3° when a 1 mg/mL solution of the Pluronic surfactant was utilized in place of the PVA.

Contact angle decreases in the same range were found when devices fabricated from PGA, or copolymers of lactic and glycolic acid were similarly treated with PVA (e.g., the contact angle of films of a 50/50 copolymer decreased to 21.degree±7°). The decrease in the hydrophobicity of the polymer films was not permanent, however, as immersion of coated polymer discs into a PBS solution led to a rebound in the contact angle over a 24 hr period. For example, the contact angle of Pluronic-coated devices returned to 76.degree±2° after 24 hr in PBS. These results suggest that the coating molecule re-dissolved over time in an aqueous environment.

Porous sponges fabricated from PLA were subsequently treated with aqueous solutions of PVA to determine whether PVA infiltration would improve the ability of aqueous solutions to adsorb into three-dimensional sponges. The sponge weight increased from 8 to 98% as the PVA concentration was raised from 1 to 100 mg/mL. Infiltrating sponges with solutions of 1-10 mg/mL had a minimal effect on the device pore size and porosity, but infiltrating with a 100 mg/mL solution significantly decreased both. Devices infiltrated with a solution containing 10 mg/mL of PVA rapidly and reproducibly absorbed aqueous solutions equivalent to 98.±.1% of their pore volume, while untreated devices only absorbed a volume of water equivalent to 6.±.2% of their pore volume. Importantly, the porosity and pore size of devices returned to their original values following exposure to an aqueous environment for 24 hr. Re-dissolution of the PVA infiltrating the sponge occurred during this time, as the device weight returned to within 5.±.3% of the original value under these conditions (similar results were obtained when sponges fabricated from 85/15 PLGA were tested).

This method for fabricating devices has wide applicability. A variety of other types of water soluble molecules, such as the Pluronic surfactants, can also be utilized as the coating molecule. This type of treatment will be useful for improving cell seeding into a variety of hydrophobic polymer devices, both biodegradable and non-biodegradable.

EXAMPLE VI

Mineral Patterning of Tissue Scaffolds With $CaPO_4$ With and Without Fluoride

A Homogeneous Surface Mineralization

Pre-treatment to produce homogeneous surface hydrolysis may be achieved by either soaking in a NaOH solution or by treating with electromagnetic (EM) radiation as previously described. The treated biomaterial is incubated in a mineral-rich, preferably a calcium-rich, fluid, such as a body fluid or synthetic media that mimics body fluid, to spur nucleation and growth of a homogeneous mineral film on the surface. The fluid contains about 10 mM $CaF_2$ where Fluoride is to be added to the tissue scaffold.

Functionalization and concomitant mineralization can also be achieved by simply soaking in mineral-containing aqueous solutions, preferably in body fluids or synthetic media that mimic body fluids. Preparation of the polymer biomaterials using a gas-foaming/particulate leaching process is generally preferred for such one step mineralization.

B. NaOH Pre-Treatment for Surface Mineralized Films

PLGA films (about 25 μm thickness) were prepared by a pressure casting technique. Raw polymer pellets were loaded into a mold and placed in a convection oven at 200 degrees C. The molds were heated under pressure (about 22 N) for 30 sec and then cooled to room temperature.

For the creation of surface functional groups by NaOH treatment, the films were cleansed and immersed in 1.0 N NaOH solution for varying times, up to 10 minutes to create surface functional groups. Following immersion, samples were rinsed 3.times in distilled water.

C. UV Pre-Treatment for Surface Mineralized Films

PLGA films (about 25 μm thickness) were prepared by a pressure casting technique. Raw polymer pellets were loaded into a mold and placed in a convection oven at 200 degrees C. The molds were heated under pressure (about.22 N) for 30 sec and then cooled to room temperature.

For the creation of surface functional groups by UV (ultra violet) treatment, membranes were exposed to up to 8 hrs of surface irradiation.

D. Surface Mineralization After Pre-Treatment

Membranes treated by either NaOH treatment or UV treatment were subsequently incubated at 37 degrees C. in 50 ml of a simulated physiological fluid (SPF, Na: 142 mM, K: 5 mM, Ca: 2.5 mM, Mg: 1.5 mM, Cl: 148 mM, HCO3: 4.2 mM, HPO4: 1 mM, SO4: 0.5 mm) buffered to pH 7.4. When fluoride was included, the solution contains 1.25 mM $CaF_2$. Solutions were replaced every 48 hours to ensure that there were sufficient ions in solution to induce mineral nucleation and growth. Following immersion for periods of 120 to 240 hours, samples were dried.

Fourier transform infrared (FTIR) analysis indicates the presence of a surface amorphous apatite. FTIR spectra of scaffolds treated for 0, 2, 6, 10, and 16 days indicate the growth of a carbonated apatite mineral within the scaffold. Equivalent spectra were also produced with the UV-treated films. The broad band at 3570 $cm^{-1}$ is indicative of the stretching vibration of hydroxyl ions in absorbed water. The peak at 1454 $cm^{-1}$ is indicative of $CO_3^{2}$, .η3, while the 867 $cm^{-1}$ represents $CO_3^{2-}$—.η2. The peaks at 1097 $cm^{-1}$ and 555 $cm^{-1}$ are indicative of anti-symmetric stretch (η3) and anti-symmetric bending (η4) of $PO_4^{3-}$, respectively. The peak at 1382 $cm^{-1}$ represent a $NO_3$ band.

The presence of $OH^-$, $CO_3^{2-}$ and $PO_4^{3-}$ all indicate that an apatitic layer has been formed. Other bands representative of apatites are masked because of the strong absorption of the PLGA.

The major peaks at 1755 $cm^{-1}$ and 1423 $cm^{-1}$ represent PLGA, and the peak at 1134 $cm^{-1}$ indicative of C—O stretch in the ester. The peaks at 756 $cm^{-1}$ and 956 $cm^{-1}$ are indicative of the amorphous domains of the polymer.

The scaffolds demonstrated an increase in mass over time, culminating in a 11.±.2% mass gain at the end of the 16 day incubation. ANOVA of percent mass changes of experimental scaffolds reveal a significant difference in scaffold mass over time ($p<0.05$), while ANOVA of percent mass changes of control scaffolds does not show a significant difference over time ($p>0.05$). Percent mass changes of experimental samples and control samples were significantly different for each time point beyond 8 days ($p<0.05$).

To confirm that the increase in mass was caused by deposition of an apatitic mineral, the mass of phosphate in the scaffolds was next analyzed. Phosphate content within the treated scaffolds also increased significantly with the treatment time. Comparison of phosphate masses via ANOVA show a statistically significant increase over time ($p<0.05$), and the differences in phosphate mass between day 8 and 12 ($p<0.05$) and between day 12 and 14 ($p=0.05$) were also statistically significant. After a 14 day incubation, estimation of the mass of mineral on the scaffold using phosphate mass data gives 0.76 mg of hydroxyapatite, while the measured mass increase of the scaffold is $1.02.\pm.0.40$ mg. The fact that the measured value is larger than the estimated value suggests significant carbonate substitution in the mineral crystal.

Growth of the BLM layer significantly increased the compressive modulus of 85:15 PLG scaffolds without a significant decrease in scaffold porosity. The compressive modulus increased from $60.\pm.20$ KPa before treatment to $320.\pm.60$ KPa after a 16 day treatment, a 5-fold increase in modulus. ANOVA of modulus changes of experimental scaffolds reveal a significant difference in scaffold modulus over time ($p<0.05$), while ANOVA of control modulus data does not show a significant difference over time ($p>0.05$). The differences between moduli of experimental scaffolds and moduli of control scaffolds were statistically significant for treatment times of 10 days or longer ($p<0.05$). The porosity of the scaffolds did not decrease appreciably after incubation in SBF. Untreated scaffolds were $95.6.\pm.0.2\%$ porous, while scaffolds incubated in SBF for 16 days were $94.0.\pm.0.30\%$ porous (n=3). This agrees with the electron micrographs, which displayed only a thin (1-10 μm) mineral coating, and thus no significant change in pore size due to mineral growth.

E One Step Mineralization

One step, room temperature incubation processes can also be used to cause nucleation and growth of mineral layers on polymer surfaces. This is achieved by incubating polymer scaffolds in mineral-containing aqueous solutions, such as body fluids and synthetic media that mimic body fluids. These processes are able to grow bone-like minerals within polymer scaffolds in surprisingly simple and inexpensive methods. The effectiveness of these methods under room temperature conditions renders them conducive to the inclusion of bioactive proteins and other materials into the processing mineralization.

A first example of one step mineralization concerns the mineral deposition on porous poly(lactide-co-glycolide) sponges via incubation in a simulated body fluid. The simple incubation technique was used to obtain nucleation and growth of a continuous carbonated apatite mineral on the interior pore surfaces of a porous, degradable polymer scaffold. Fluoride was also incorporated into the scaffold. The incorporation of calcium phosphate and fluoride into the scaffolds renders them suitable hydrogels to facilitate regeneration of enamel. In cases where no tissue in growth is needed, a hydrogel having a porosity of less than 50% or less than 40% or less than 30%, or less than 20%, or less than 10%, or between about 2% and about 10% may be used as a hydrogel plug in contact with the enamel of a tooth.

A 3-dimensional, porous scaffold of 85:15 PLG was fabricated by a solvent casting/particulate leaching process and incubated in simulated body fluid (SBF; NaCl-141 mM, KCl-4.0 mM, $MgSO_4$-0.5 mM, $MgCl_2$-1.0 mM, $NaHCO_3$-4.2 mM, $CaCl_2$-2.5 mM, and $KH_2PO_4$-1,0 mM, with or without 1.25 mM $CaF_2$ in deionized $H_2O$, buffered to pH=7.4 with Trisma-HCl). Fourier transform IR spectroscopy and SEM analyses after different incubation times demonstrated the growth of a continuous bone-like apatite layer within pores of the polymer scaffold.

The majority of the mineral growth occurred between days 8 and 12. Mineral growth into a continuous layer likely occurs from day 12, and is complete at or before day 16. The mineral grown, being continuous, is thus similar to that in bones and teeth.

The scaffolds demonstrated an increase in mass over time, with an $11.\pm.2\%$ gain after 16 days. The increase in mass is due to deposition of an apatitic material. Quantification of phosphate on the scaffold revealed the growth and development of the mineral film over time with an incorporation of 0.43 mg of phosphate (equivalent to 0.76 mg of hydroxyapatite) per scaffold after 14 days in SBF. The measured overall mass increase of the scaffold was $1.02.\pm.0.4$ mg at 14 days. This suggests carbonate substitution in the mineral crystal.

The compressive moduli of polymer scaffolds also increased fivefold with formation of a mineral film after a 16 day incubation time, as opposed to control scaffolds. This was achieved without a significant decrease in scaffold porosity. The thin mineral coating is thus functionally important, yet mineralization does not change the pore size.

85:15 PLGA scaffolds prepared by gas foaming/particulate leaching exhibit even more rapid nucleation and growth of apatitic mineral. The 85:15 PLG scaffolds prepared via solvent casting/particulate leaching showed a $3.\pm.1\%$ increase in mass after a 6 day incubation in SBF. In comparison, 85:15 PLGA scaffolds prepared by gas foaming/particulate leaching showed a mass increase of $6.\pm.1\%$ after a 4 day incubation in SBF.

The even more rapid nucleation and growth of apatitic mineral on 85:15 PLG scaffolds prepared by gas foaming/particulate leaching is believed to be due to the increase in carboxylic acid groups caused by the gas foaming/particulate leaching process, i.e., the greater surface functionalization. Leaching with 0.1 M $CaCl_2$ also likely facilitates chelation of $Ca^{2+}$ ions, producing more rapid bone-like mineral nucleation.

F. Diffraction Lithography

Previous studies on the control of locations of cell adhesion to a biomaterial surface have utilized conventional UV lithography to pattern a two dimensional polymer surface (Pierschbacher & Ruoslahti, 1984); Ruoslahti & Pierschbacher, 1987); Matsuda et al., 1990); Britland et al., 1992); Dulcey et al., 1991); Lom et al., 1993); Lopez et al., 1993); Healy et al., 1996).

In the prior techniques, the two-dimensional biomaterial surface is coated with a thin layer of photoresist (PR), the PR is exposed through a metal mask, and the exposed PR is removed in solvent, leaving a PR mask on the surface of the biomaterial sample. The surface of the polymer biomaterial is then chemically or physically treated through the PR mask, and the mask is removed by a solvent after treatment.

The former processes requires a flat, two dimensional biomaterial, which suffices for studying the effects of surface treatment on cell activity, but is not sufficient for the treatment of typical biomaterials, which have three dimensional surface contours.

In the present methods, suitable for use with three dimensional polymers, the grating produces a pattern of constructive and destructive interference on the polymer surface. As the grating is not required to be in near contact with the biomaterial during treatment, this diffraction lithography process can be used to treat materials with complex three-dimensional surface contours. However, the process is equally useful in connection with two dimensional biomaterials.

G. Infiltration With Bioactive Molecules

Polymer biomaterial is treated to form a patterned biosurface, preferably using either patterned EM radiation or electron beam irradiation. Treated biomaterial is washed with distilled water to remove residual monomers from the surface photolysis or electrolysis.

The treated biomaterial is incubated in a solution containing bioactive molecules or proteins, such as growth factors, adhesion molecules, cytokines and such like, which promote adhesion of a specific cell type. Cells are seeded onto the biomaterial in vitro in a cell culture medium. In vivo, cells attach to the biomaterial when implanted. In either case, cells adhere preferentially to the treated portions of the substrate.

The use of specific agents or proteins, such as growth factors, that promote attachment of certain cell types, gives the potential to pattern any cell type on the three dimensional surface of the polymer, both in vitro and in vivo.

EXAMPLE VII

Making Tissue Scaffold Sponge Wafers Using Salt Frames

In this example, NaCl frames and biodegradable polymer scaffolds are produced. The salt particles (Mallinkrodt, Paris, Ky.) were sieved to yield a range of sizes. NaCl crystals of a diameter of about 250-425 µm were used.

Porous scaffolds were prepared either by solvent casting/particulate leaching, or gas foaming/particulate leaching processes using NaCl as the particulate porogen. The solvent cast scaffolds were prepared essentially as described by Mikos, A. G., et al. ("Preparation and characterization of poly(L-lactic acid) foams" Polymer 35:1068, 1994; which is incorporated herein by reference). NaCl molds were made by subjecting NaCl crystals (diameter of about 250☐425 µm) to 95% humidity for periods from 0☐24 hr to achieve fusion of NaCl crystals prior to solvent casting. A closed, water-jacketed cell culture incubator (Form a Scientific, Inc.) held at 37 0 C was used to create a 95% humidity environment for fusion of NaCl crystals.

Poly(lactide-co-glycolide) (PLG) pellets with a lactide:glycolide ratio of 85:15 were obtained from Medisorb, Inc. (intrinsic viscosity (I.V.)=0.78 dl/g) and Boehringer-Ingelheim Inc. (I.V. =1.5 dl/g). High inherent viscosity PLG was used in the solvent casting process to ensure that the scaffolds would retain adequate mechanical integrity despite their relatively high porosity (~97%). PLG pellets were dissolved in chloroform (Mallinkrodt, Paris, Ky.) to yield a solution of 10% weight/volume (w/v). The polymer solution was then poured into an NaCl containing mold wherein the salt crystals had been fused, as described above. Following solvent evaporation, the salt was removed by immersion in distilled water for about 48 hours.

The gas foamed scaffolds were essentially prepared as described by Harris, L. D., et al. ("Open pore biodegradable matrices formed with gas foaming" J Biomed Mater Res 42:396, 1998; which is incorporated herein by reference). NaCl molds were made by subjecting NaCl crystals (diameter of about 250☐425 µm) to 95% humidity for periods from 0☐24 hr to achieve fusion of NaCl crystals prior to solvent casting. Following treatment in 95% humidity samples were dried in a vacuum desiccator for 48 hr before further processing. A closed, water—jacketed cell culture incubator (Form a Scientific, Inc.) held at 370 C was used to create a 95% humidity environment for fusion of NaCl crystals. PLG pellets (prepared as above) were dissolved in chloroform. Frames of fused NaCl were mixed with PLG were loaded into an aluminum die (1.35 cm diameter; Aldrich Chemical Co., Milwaukee, Wis.) and was compressed at 1500 Psi for 1 minute using a Carver Laboratory Press (Fred S. Carver, Inc., Menominee Falls, Wis.) to yield solid disks (thickness of about 3.4 mm). The samples were then exposed to high pressure $CO_2$ gas (800 psi) for 24 hours to saturate the polymer with gas. A thermodynamic instability then was created by decreasing the gas pressure to ambient pressure. This lead to the nucleation and growth of $CO_2$ pores within the polymer matrices. The NaCl particles subsequently were removed from the matrices by leaching the matrices in distilled water for 48 hours. All processing steps were performed at ambient temperature.

Scaffolds were circular disks with a diameter of about 12 mm and a thickness of about 3 mm. The pore size range was controlled by using NaCl particles with a diameter of about 250☐425 µm in the processing. The total porosity of scaffolds was calculated using the known density of the solid polymer, the measured polymer mass of the scaffold, and the measured external volume of the scaffold.

Incubation of NaCl crystals in 95% humidity resulted in fusion of the crystals, creating a highly interconnected NaCl matrix. Fused salt molds were bisected and imaged prior to solvent casting to observe the extent of NaCl crystal fusion. In addition, polymer scaffolds were bisected after preparation via freeze fracture. A carbon coating was evaporated onto the surface of each bisected salt mold and polymer scaffold, and samples were imaged under high vacuum using a Hitachi S☐3200N SEM operating at 20☐30 kV. Fusion of salt crystals prior to addition of PLG in chloroform (solvent casting) resulted in enhanced pore interconnectivity within the scaffold. The pore structure within the scaffolds appears similar to the structure of the fused salt matrix, as expected. Pores within the cross section of 1 hr salt fusion (SF) samples display a defined pore structure with intermittent holes in pore walls, while the cross section of scaffolds created from 24 hr SF samples display a much less organized pore structure and a very large density of holes in pore walls. The hole size increased significantly with fusion time, from an average diameter of 31+10 µm after 1 hour of fusion to 78+21 µm after 24 hours of fusion (p<0.05). In addition, the pore walls in the 24 hr SF scaffolds display thickness contours such that the walls appear thicker in the area adjacent to the holes in pore walls and along the outer diameter of the walls. A higher magnification view of a pore wall within a 24 hr SF scaffold further displays the contoured structure of the pore walls. The salt fusion process had no effect on the porosity of the scaffolds, and the calculated total porosities of the solvent cast scaffolds for each salt fusion time period were 97+1%.

A close examination of the electron micrographs of the solvent cast scaffolds formed after 1 and 24 hours of NaCl fusion indicate that the exposure to 95% humidity has caused several important changes in the structure of the salt particles. In addition to the formation of bridges between particles at the points of contact, the radius of curvature of edges and corners in individual particles of salt has increased. These changes are shown schematically. The radius of curvature of salt crystals was calculated from electron micrographs. The pixel size for each image was calibrated, and the pencil tool was used to mark tangent points on crystal edges. The calibration values and pixel coordinates were then used to calculate the cord length between tangent points, which was multiplied by (2/2 to obtain the crystal radius of curvature. The diameter of holes in pore walls was determined by measuring the major and minor diametral axes of each hole using microsoft paint and taking the average. The increased radius of curvature at the edges and corners of each particle of salt results in an increased sphericity of each particle, and thus in each resulting pore in the scaffold. The mean radius of curvature of the crystal edges increased from 19+10 µm, to 32+15 µm after 12 hours of exposure to 95% humidity, then to 62+18 µm after a full 24 hours of exposure. As a result, many of the smaller crystals became nearly spherical in shape after 24 hours of fusion. One additional consequence is that thicker polymeric struts may be formed in the space vacated by the corners and edges of each salt crystal, which may result in the thickness contours in pore walls described above and in varied mechanical properties.

Fusion of salt crystals in PLG/NaCl pellets prior to gas foaming also resulted in a pronounced variation in pore structure. The cross section of 1 hr SF samples shows small holes in pore walls similar to those in the solvent cast 1 hr SF samples. The 24 hr salt fusion samples lack a defined pore structure and pores appear to simply feed into each other. The gas foamed SF scaffolds do not display any of the contours in pore walls observed in the solvent cast SF samples. Again, the salt fusion process had no effect on the total scaffold porosity. The total porosities of the gas foamed scaffolds for each salt fusion time period were 94+1%.

Fusion of salt crystals for 24 hr resulted in a 2 fold increase in the compressive modulus of the solvent cast scaffolds. Compressive moduli of scaffolds were determined using an MTS Bionix 100 mechanical testing system. Samples were compressed between platens with a constant deformation rate of 1 mm/min. Compression plates had a diameter of 45 mm, and thus covered the entire 12 mm diameter surface of the scaffold. A small pre-load was applied to each sample to ensure that the entire scaffold surface was in contact with the compression plates prior to testing, and the distance between plates prior to each test was equal to the measured thickness of the scaffold being tested. Compressive moduli were determined for scaffolds without salt fusion and for each of four samples for each salt fusion time. Values on graphs represent means and standard deviations. Statistical analysis was performed using InStat software, version 2.01. At each time point, experimental moduli were compared to control moduli via a Student's t-test to reveal significant differences in compressive modulus. No significant modulus change is observed after 1 hr, or 12 hr of salt fusion. Alternatively, there was a statistically significant decrease in the compressive modulus of gas foamed scaffolds processed using salt fusion when compared with control scaffolds.

EXAMPLE VIII

Incorporation of Morphogenic Agents Into a Tissue Scaffold Wafer (HYDROGEL?)

A. Wafer Preparation and Characterization

Wafers containing BMP-7 are prepared by a modification of a previously described double-emulsion technique (Cohen et al., 1991). In brief, a 75/25 copolymer of poly-(D,L-lactic-co-glycolic) acid (Resomer RG 75R, intrinsic viscosity 0.2; Henley Chem. Inc., Montvale, N.J.) is dissolved in ethyl acetate (Fisher Scientific) to yield a 5% solution (w:v). Recombinant human BMP-7 is dissolved in water to yield a solution of 2 mg/ml, and 50 ml of the BMP-7 solution is added to 1 ml of the polymer solution. The polymer/BMP-7 solution is sonicated continuously at 10 watts (Vibracell; Sonics and Materials, Danbury, Conn.) for 15 sec to yield a single emulsion.

An equal volume of an aqueous solution containing 1% polyvinyl alcohol (MW 25,000, 88% hydrolyzed; Polysciences Inc., Warrington, Pa.) and 7% ethyl acetate is added to the single emulsion, and the resulting solution is vortexed (Vortex Mixer; VWR) for 15 sec at the high setting to yield the double emulsion. This double emulsion is transferred to a rapidly stirring 250 ml beaker containing 150 ml of an aqueous solution of 0.3% polyvinyl alcohol/7% ethyl acetate. The double emulsion is distributed into casting molds of selected dimensions for the wafer, and the ethyl acetate is allowed to evaporate over the ensuing 3 hr to yield polymer wafers with entrapped BMP-7. The wafers are then filtered and washed with water. The wafers are lyophilized (Labconco Freeze Dryer, Kansas City, Mo.), and stored at −20° C. until use. Control wafers are prepared with the same procedure, but the aqueous solution used to form the first, single emulsion (water in organic) contained no BMP-7.

To determine the efficiency of BMP-7 incorporation and the kinetics of BMP-7 release from the wafers, the BMP-7 is labelled with $^{125}$I using standard labelling techniques to obtain a specific activity of about 10 to 1000 mCi/mg. Approximately 1 µCi of labelled BMP-7 is added to the aqueous BMP-7 solution before formation of the single emulsion, and the wafers are prepared as described above. After wafer fabrication, a known mass of wafers is counted in a scintillation counter and the incorporated cpm is compared to that of the initial aqueous BMP-7 solution to calculate the percentage of the total BMP-7 that is incorporated into the wafers.

To determine the release of BMP-7 from wafers, a known mass of wafers (approximately 10 mg) prepared with the labelled EGF is placed in a known volume (2 ml) of phosphate buffered saline (PBS) solution containing 0.1% Tween 20 (Sigma Chem. Co.) and placed in an incubator maintained at 37° C. At set times, the solution is centrifuged to concentrate the beads at the bottom of the vial, and samples (0.1 ml) of the PBS/Tween 20 solution is removed. The sample volume is replaced with fresh PBS/Tween 20 solution. The amount of $^{125}$I-BMP-7 released from the wafers is determined (n=4) at each time point by counting the removed sample in a gamma counter, and compared to the $^{125}$I-BMP-7 loaded into the wafers. The maximum theoretical BMP-7 concentration in the release medium (approximately 5 mg/ml) should be well below the maximum solubility of BMP-7, thus establishing sink conditions for the release study.

B. Results

The yield of wafers with this process should be about 92+5%.

To determine the efficiency of BMP-7 incorporation into wafers, and the release profile from the same the $^{125}$I-labelled BMP-7 is utilized as a tracer. Approximately ½ of the initial BMP-7 (53+11%) will be incorporated into wafers. When BMP-7-containing wafers are placed in an aqueous medium, an initial burst of BMP-7 release will be noted. After this time BMP-7 will be released in a steady manner over the remainder of a 30 day time course.

The time over which a drug is released from a polymer matrix can typically be regulated by the drug loading, the type of polymer utilized, and the exact processing conditions (Mooney et al., 1992). The release of protein from copolymers of lactic and glycolic acid, such as utilized in this Example, is generally controlled by the erosion of the polymer when the protein/polymer ratio is low (Cohen et al., 1991). The released protein must retain its biological activity for this approach to be useful. The biological activity of the BMP-7 incorporated into and released from wafers in this Example will not be adversely affected. This approach to delivering BMP-7 can also be readily expanded to deliver other molecules such as BMP-2, BMP-4. VEGF or any morphogenic protein, alone or in combination with such proteins.

EXAMPLE IX

Alginate Hydrogel Growth Factor Incorporation and Release From a Foamed Matrix Tissue Scaffold About 1 to 100 mg of $^{125}$I-labelled protein growth factor is first added to a solution of 1% sodium alginate, and then beads of this solution are gelled by injecting droplets into a aqueous solution containing calcium chloride. The alginate beads (approximately 3 mm in diameter) are collected, rinsed, and lyophilized. The lyophilized beads are mixed with 85:15 PLGA and NaCl particles and the mixture is compression moulded and processed with the gas foaming/particulate leaching process as previously described.

To test for release, after salt leaching and drying, the matrices are placed in serum free tissue culture medium and maintained at 37° C. Medium samples are taken periodically, and analyzed for the content of 125I-VEGF (released from PLGA matrices). The released growth factor may be normalized to the total incorporated growth factor.

Results will show that an initial burst of approximately 20% of the incorporated growth factor occurs in the first day, and a sustained release of growth factor will be noted for at 20 days.

EXAMPLE X

Growth Factor Incorporation and Release from Mineralized Matrices

A. Materials and Methods
1. Gas Foaming-Particulate Leaching
Poly(lactide-co-glycolide) pellets with a lactide:glycolide ratio of 85:15 obtained from Medisorb, Inc. (I.V.=0.78 dl/g) and ground to a particle size between 106 and 250 µm. Ground PLGA particles are then combined with 250 µl of a 1% alginate (MVM, ProNova; Oslo, Norway) solution in ddH$_2$O, with about 1 to about 1000 µg of a morphogenic protein such as BMP-2, BMP-4, BMP-7 or VEGF and the like, or combinations of such morphogenic proteins. These solutions are lyophilized, mixed with 100 mg of NaCl particles (250 µm<d<425 µm), and compression moulded at 1500 psi for 1 min in a die of suitable size. A typical 4.2 mm diameter die yields 2.8 mm thick disks with a diameter of 4.2 mm.

Disks are then exposed to 850 psi CO$_2$ gas in an isolated pressure vessel and allowed to equilibrate for 20 h. The pressure is decreased to ambient in 2 min, causing thermodynamic instability, and subsequent formation of gas pores in the polymer particles. The polymer particles expand and conglomerate to form a continuous scaffold with entrapped alginate, morphogenic protein, and NaCl particles. After gas foaming, the disks are incubated in 0.1 M CaCl$_2$ for 24 h to leach out the salt particles and induce gelation of the alginate within the polymer matrix. Alginate is included in the scaffolds because it has been shown to abate the release of VEGF from PLGA scaffolds (Wheeler et al., 1998).

2. Mineralization
Certain scaffolds are mineralized via a 5 day incubation in a simulated body fluid (SBF). Simulated body fluid (SBF) was prepared by dissolving the following reagents in deionized H$_2$O: NaCl-141 mM, KCl-4.0 mM, MgSO$_4$-0.5 mM, MgCl$_2$-1.0 mM, NaHCO$_3$-4.2 mM, CaCl$_2$-2.5 mM, and KH$_2$PO$_4$-1.0 mM. The resulting SBF is buffered to pH 7.4 with Trisma-HCl and held at 37.degree C. during the incubation periods. The SBF solutions are refreshed daily to ensure adequate ionic concentrations for mineral growth.

The porosity of scaffolds is calculated before and after mineralization treatment using the known density of the solid polymer, the known density of carbonated apatite, the measured mass of mineral and polymer in the scaffolds, and the volume of the scaffold.

3. Characterization of Mineral Growth
To analyze mineral growth on gas foamed PLG scaffolds, sets of three scaffolds were incubated in SBF for periods ranging from 0-10 days. Samples were removed from solution and analyzed after 0, 2, 4, 8, and 10 day incubation periods. The dry mass of each scaffold is measured before and after incubation in SBF, and percent increases in mass is calculated and compared using ANOVA and a Student's t-test to reveal significant differences in mass for different SBF incubation times.

The amount of phosphate present in the scaffolds after the aforementioned incubation times is determined using a previously described calorimetric assay (Murphy et al., J. Biomed. Mat. Res., In Press; incorporated herein by reference). The phosphate mass data were also compared using ANOVA and a Student's t-test to reveal significant differences in mass for different SBF incubation times.

To estimate the amount of apatite on the scaffold after a 6 day incubation, the measured mass of phosphate is multiplied by the known ratio of mass of hydroxyapatite [Ca$_{10}$(PO$_4$)$_6$(OH)$_2$, f.w.=1004.36 g] to mass of phosphate in hydroxyapatite (569.58 g). This is a conservative estimate, since it assumes that all phosphate is being incorporated into stoichiometric hydroxyapatite. This mineral mass estimate increases if one assumes increasing substitution of carbonate into the mineral crystal.

4. Growth Factor Release Measurements
In order to assess the incorporation efficiency of the morphogenic growth factors into the PLG scaffolds and to track the growth factor release kinetics from the scaffolds, the growth factor is labelled with $^{125}$I to a specific activity of about 1 to 1000.µCi/.µg in place of the unlabelled growth factor in the normal sample preparation To assess growth factor incorporation efficiency, the total incorporated activity is compared to the activity of the initial $^{125}$I growth factor sample prior to incorporation into the scaffolds.

To determine the effects of mineral growth on factor release, release kinetics are measured both in SBF during mineral formation and in phosphate buffered saline (PBS). Scaffolds prepared with radiolabeled growth factor are placed in 4 ml of SBF or PBS and held at 37 degrees C. At various set times, the scaffolds are removed from solution and their radioactivity is assessed using a gamma counter. After each analysis, solutions are refreshed and scaffolds are placed back into solution.

The amount of radiolabeled growth factor released from the scaffolds is determined at each time point by comparing the remaining $^{125}$I growth factor to the total originally loaded into each scaffold. The percent release of VEGF from scaffolds incubated in SBF is compared to that of scaffolds incubated in PBS at each time point via a Student's t-test to reveal significant differences in cumulative release.

B. Results

1. Mineralization

Incubation of gas foamed 85:15 poly(lactide-co-glycolide) scaffolds containing growth factors results in the growth of bone-like mineral on the inner pore surfaces. Analysis of variance will show that differences in percent mass gain with SBF incubation time is significant ($p<0.05$). The scaffolds show an increase in mass with incubation time, with a 6±1% mass gain after a 4 day incubation in SBF. The scaffold mass will subsequently remained relatively constant. The increase in mass between two day and four day incubation times will be significant $p<0.05$), while there will be no significant difference in percent mass gain between the four day incubation time and the longer incubation times ($p>0.05$).

To verify that the increase in mass is caused by the deposition of an apatitic mineral, the mass of phosphate in the scaffolds can be analyzed. Phosphate content within scaffolds increased with SBF incubation time. Analysis of variance will show that differences in phosphate content with SBF incubation time is significant ($p<0.05$). The difference in phosphate content between the two day and six day incubation times will be significant ($p<0.05$), while there will be no significant difference between the phosphate mass of the six day incubation time and longer incubation times ($p>0.05$).

It has previously been shown that the increase in mass and phosphate content in these scaffolds indicates growth of a continuous bone-like mineral film on the inner pore surfaces (Murphy et al., J. Biomed. Mat. Res., In Press).

The total porosity of the scaffolds after a 10 day incubation in SBF is about 92±1%, which is similar to the initial scaffold porosity (93±1%).

After a 6 day incubation, estimation of the mass of mineral on the scaffold using phosphate mass data gives 0.10 mg of hydroxyapatite, while the measured mass increase of the scaffold is 0.39.±.0.03 mg. The fact that the measured value is larger than the estimated value indicates significant carbonate substitution in the mineral crystal.

2. Growth Factor Release and Activity

Growth factors are incorporated into PLGA scaffolds with an efficiency of 44±9% and is released over a 15 day period in SBF and PBS solutions. An initial burst release of the incorporated growth factor will be observed over the first 12-36 h followed by a sustained release for 20 days or more.

The cumulative release from scaffolds incubated in SBF becomes significantly smaller than release from scaffolds incubated in PBS after 3 days, and this difference will remain significant through 10 days of release ($p<0.05$). At time points beyond 10 days there is no significant difference in cumulative release from scaffolds incubated in SBF versus those incubated in PBS.

The foregoing examples are included to demonstrate preparation or execution of preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

The invention claimed is:

1. A method for treating a subject's tooth that needs regeneration of dentin, comprising,
    forming a hole in the tooth of the subject in vivo, the hole being of a depth sufficient to expose at least a portion of pulp;
    inserting a tissue scaffold into the hole so that a portion of the tissue scaffold contacts at least a portion of the exposed pulp; and
    regenerating dentin by allowing sufficient time for tissue to grow in vivo, from the pulp into the tissue scaffold, wherein that the tissue scaffold inserted into the hole does not include ex vivo cultured tissue.

2. The method of claim 1 wherein the tissue scaffold is formed into a shape dimensioned to fit snuggly into the hole that is formed so that the tissue scaffold does not move more than 0.1 mm in a lateral direction in the hole.

3. The method of claim 1 wherein the tissue scaffold is formed into a cylindrical wafer having a diameter of about 2 to about 5 mm and a height of about 0.1 to about 0.5 mm.

4. The method of claim 1 further comprising inserting dental stem cells into the hole between the exposed portion of the pulp and the tissue scaffold.

5. The method of claim 1 wherein the tissue scaffold is seeded with dental pulp stem cells prior to insertion into the hole.

6. The method of claim 1 wherein the tissue scaffold is comprised of calcium phosphate associated therewith.

7. The method of claim 6 wherein the tissue scaffold is comprised of fluoride associated therewith.

8. The method of claim 1 wherein the tissue scaffold is comprised of scaffolding material selected from the group consisting of PLLA, PDLLA, PGA and PLGA.

9. The method of claim 1 wherein the tissue scaffold comprised of scaffolding material is PLGA.

10. The method of claim 1 wherein the tissue scaffold is farther comprised of a physiologically effective amount of a morphogenic agent that promotes growth of dentin tissue.

11. The method of claim 10 wherein the morphogenic agent is encoded by a member of the TGF-$\beta$ supergene family.

12. The method of claim 10 wherein the morphogenic agent is selected from the group consisting of BMP-2, BMP 4, BMP-7, VEGF, FGF-1, FGF-2, IGF-1, IGF-2, PDGF, GDF-1, GDF-2, GDF-3, GDF-4, and GDF-5.

13. The method of claim 10 wherein the morphogenic agent is selected from the group consisting of BMP-2, BMP 4, BMP-7, and GDF-5.

14. The method of claim 1 wherein the tissue scaffold is further comprised of an active agent selected from the group consisting of an anti-bacterial agent and an anti-inflammatory agent.

15. The method of claim 1 wherein the tissue scaffold has the shape of a cylindrical wafer having an upper surface, a downwardly extending cylindrical side, and a lower surface.

16. The method of claim 1 further including applying a barrier layer in contact with an exposed surface of the scaffold material to seal the scaffold material in the hole.

17. The method of claim 16 wherein the barrier layer is comprised of a hydrogel.

18. The method of claim 17 wherein the hydrogel comprises a physiologically effective amount of a morphogenic agent that promotes growth of dentin tissue.

19. The method of claim 17 wherein the barrier hydrogel comprises an active agent selected from the group consisting of an anti-bacterial agent and an anti-inflammatory agent.

20. The method of claim 17 wherein the morphogenic agent is encoded by a member of the TGF-β supergene family.

21. The method of claim 17 wherein the morphogenic agent is selected from the group consisting of BMP-2, BMP 4, BMP-7, VEGF, FGF-1, FGF-2, IGF-1, IGF-2, PDGF, GDF-1, GDF-2, GDF-3, GDF-4, and GDF-5.

22. The method of claim 17 wherein the morphogenic agent is selected from the group consisting of BMP-2, BMP 4, BMP-7, and GDF-5.

23. The method of claim 1 further including covering the hole with a cement or amalgam that contacts at least a portion of tooth enamel.

24. The method of claim 23 wherein the cement is comprised of di-calcium phosphate and tetra calcium phosphate.

25. The method of claim 23 wherein the cement is comprised of calcium phosphate and fluoride.

26. The method of claim 1 wherein the subject has asymptomatic caries and the act of forming the hole exposes a portion of the pulp located in the coronal pulp chamber.

27. The method of claim 1 wherein the subject has need of a root canal and the act forming the holes exposes a portion of the pulp between at least one of the coronal pulp chamber and the root canal.

28. A device for treating a tooth comprising,
a tissue scaffold comprised of a scaffolding polymer configured as a wafer that fits snuggly into a corresponding hole that is formed in a tooth of the subject so that the tissue scaffold does not move more than 0.1 mm in a lateral direction in the hole, wherein the tissue scaffold does not include ex vivo cultured tissue.

29. The device of claim 28 wherein the hole of corresponding size is formed by an act of drilling the tooth.

30. The device of claim 28 wherein the wafer is cylindrical and has a diameter of about 2 to about 5 mm and a has height of about 2 to about 4 mm.

31. The device of claim 28 wherein the scaffolding polymer is made of a material selected from the group consisting of PLLA, PDLLA, PGA and PLGA.

32. The device of claim 28 wherein the scaffolding material is associated with calcium phosphate.

33. The device of claim 32 wherein the wafer is further associated with fluoride.

34. The device of claim 28 further comprising a pharmaceutically acceptable hydrating liquid.

35. The device of claim 28 wherein the wafer has a top surface, a bottom surface and a side perimeter surface between the top and bottom surfaces, and wherein at least one of the top and bottom surfaces are marked with a pattern that alters appearance when the wafer is crushed.

36. The device of claim 35 wherein the pattern is comprised of set of concentric circles.

37. The device of claim 35 wherein the pattern is comprised of a dye that alters color when the wafer is compressed.

38. A kit containing a plurality of wafers according to claim 28 and wherein the plurality of wafers are of a plurality of sizes selected to correspond with a plurality of hole sizes.

39. The kit of claim 38 wherein the plurality of hole sizes correspond to a plurality of holes made by drilling a tooth with any one of a plurality of dental drill bit sizes.

40. A kit for providing a method of treating dental conditions, comprising:
a dry tissue scaffold wafer dimensioned to be received into a hole of corresponding size formed in a tooth of a subject;
a well configured to hold the tissue scaffold wafer in a dry state,
a second well adjacent to the first well, the second well holding a hydrating liquid comprising a pharmaceutically acceptable liquid; and
a breakable partition separating the first and second wells, the breakable partition being structured to break by a force applied by a human hand causing the tissue scaffold wafer to contact hydrating liquid when the breakable partition is broken.

41. The kit of claim 40 wherein a plurality of the first wells are configured with a plurality of second wells, each member of the plurality of first and second wells having the breakable partition between the wells.

42. The kit of claim 41 wherein the plurality of first wells is dimensioned to hold a plurality of dry wafers of different sizes.

43. The kit of claim 40, further comprising a hydrogel material.

44. The kit of claim 43 wherein the hydrogel is hydrated, contained in a well in the kit, and has a size that corresponds to a size of the tissue scaffold wafer.

45. The kit of claim 44 including a plurality of hydrogels.

46. The kit of claim 43 wherein the hydrogel material is provided in a dry state in the kit.

47. The kit of claim 46 further comprising a hydrating liquid for hydrating the dry hydrogel material.

48. The kit of claim 46 wherein at least one of the dry tissue scaffold or the hydrating agent or a hydrogel optionally included with the kit, contains a morphogenic agent.

49. The kit of claim 48 wherein the morphogenic agent is encoded by a member of the TGF-β supergene family.

50. The kit of claim 48 wherein the morphogenic agent is selected from the group consisting of BMP-2, BMP 4, BMP-7, VEGF, FGF-1, FGF-2, IGF-1, IGF-2, PDGF, GDF-1, GDF-2, GDF-3, GDF-4, and GDF-5.

51. The kit of claim 48 wherein the morphogenic agent is selected from the group consisting of BMP-2, BMP 4, BMP-7, and GDF-5.

52. The kit of claim 48 wherein the morphogenic agent is supplied with the hydrating liquid.

53. The kit of claim 48 wherein the morphogenic agent is supplied with the hydrogel.

54. The kit of claim 48 wherein the morphogenic agent is supplied with the dry tissue scaffold water.

55. A device for supporting a tissue scaffold wafer comprising,
a support casing at least partially surrounding the tissue scaffold wafer, the tissue scaffold wafer being made of a porous scaffolding material having a first crushing resistance and the support casing being made of a material having a second crushing resistance greater than the first crushing resistance.

56. The device of claim 55 wherein the support casing includes at least one horizontally disposed member that contacts at least one of an upper and lower surface of the tissue scaffold wafer and wherein the support casing includes at least one columnar extension extending from the horizontally disposed member along a side perimeter of the tissue scaffold wafer.

57. The device of claim 56 wherein the horizontally disposed member of the support casing includes at least one ring that contacts an outer perimeter of at least one of an upper and lower surface of the tissue scaffold wafer.

58. The device of claim 56 wherein the horizontally disposed member includes a bracket member.

59. The device of claim 56 wherein the horizontally disposed member includes a pad member.

60. The device of claim 56 wherein the horizontally disposed member includes a brace member.

61. The device of claim 55 wherein the support casing includes a plurality of the columnar extensions of the support material.

62. The device of claim 55 wherein the support casing is biodegradable in a mouth of an animal.

* * * * *